United States Patent
Li et al.

(10) Patent No.: US 10,053,498 B2
(45) Date of Patent: Aug. 21, 2018

(54) COMPOSITIONS COMPRISING SERUM ALBUMIN AND P53 PEPTIDES FUSION PROTEINS

(71) Applicant: University of the Sciences of Philadelphia, Philadelphia, PA (US)

(72) Inventors: Zhiyu Li, Woodstock, MD (US); Michelle Parker, Leander, TX (US)

(73) Assignee: University of the Sciences of Philadelphia, Philadelphia, PA (US)

(*) Notice: Subject to any disclaimer, the term of this patent is extended or adjusted under 35 U.S.C. 154(b) by 0 days.

(21) Appl. No.: 14/948,010

(22) Filed: Nov. 20, 2015

(65) Prior Publication Data
US 2016/0145314 A1    May 26, 2016

Related U.S. Application Data

(60) Provisional application No. 62/083,010, filed on Nov. 21, 2014.

(51) Int. Cl.
| | |
|---|---|
| *C07K 14/47* | (2006.01) |
| *A61K 45/06* | (2006.01) |
| *A61K 38/00* | (2006.01) |
| *C07K 14/765* | (2006.01) |

(52) U.S. Cl.
CPC .......... *C07K 14/4746* (2013.01); *A61K 45/06* (2013.01); *C07K 14/765* (2013.01); *A61K 38/00* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 6,630,584 B1* | 10/2003 | Solomon | C07K 16/18 424/130.1 |
| 2004/0014652 A1 | 1/2004 | Trouet | |
| 2008/0280769 A1 | 11/2008 | Doemling | |
| 2010/0210529 A1* | 8/2010 | van der Burg | C07K 14/4746 514/19.3 |
| 2011/0183917 A1* | 7/2011 | Lu | C07K 14/43522 514/19.3 |
| 2012/0328692 A1 | 12/2012 | Lu | |

OTHER PUBLICATIONS

Pollaro et al., Strategies to prolong the plasma residence time of peptide drugs, Med. Chem. Commun. 1, 319-324, 2010.*
International Search Report in International Application No. PCT/US2015/061980, dated Feb. 9, 2016, in 4 pages.
Joshi et al. "Human serum albumin and p53-activating peptide fusion protein is able to promote apoptosis and deliver fatty acid-modified molecules," PloS One. (Nov. 21, 2013) vol. 8, No. 11, p. 1-14.
Müer et al, "P14(ARF)-induced apoptosis in p53 protein-deficient cells is mediated by BH3-only protein-independent derepression of Bak protein through down-regulation of Mcl-1 and Bcl-xL proteins," J Biol Chem. (Feb. 21, 2012) vol. 287, No. 21, p. 17343-17352.

* cited by examiner

*Primary Examiner* — Elly-Gerald Stoica
(74) *Attorney, Agent, or Firm* — Vicki G. Norton

(57) ABSTRACT

The present invention relates to compositions useful in inhibiting Bcl-XL or MCL-1 and disrupting p53-MDM2 and p53-MDMX interactions, and methods of using those compositions for treating a subject for conditions responsive to increasing p53 mediated activity or promoting p53 independent apoptosis, such as treating cancer. In some aspects, the compositions of this invention relate to fusion polypeptides comprising a human serum polypeptide and a p53-peptide, which can be, in some aspects, a p53 derived peptide and/or a p53 activating peptide.

23 Claims, 17 Drawing Sheets

Design and purification of rHSA-P53i and rHSA-PMI.

rHSA-p53 and rHSA-PMI are efficiently taken up into SJSA-1 cells.
Fig. 2A
Fig. 2B
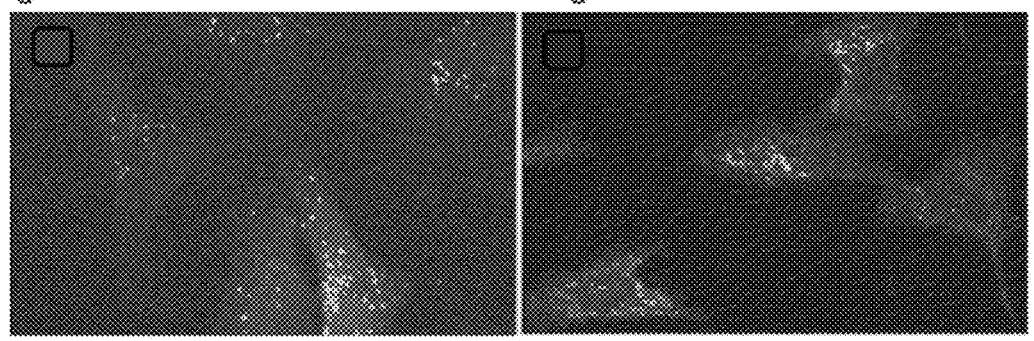
Fig. 2C
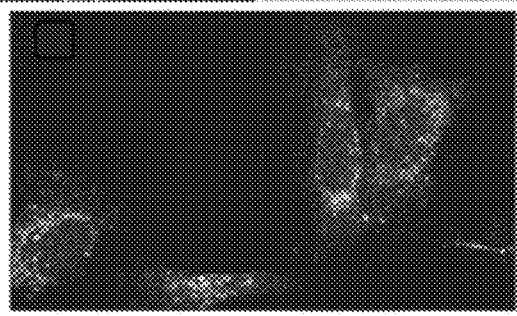

Figure 3. rHSA-P53i and rHSA-PMI bind to MDM2 and MDMX.
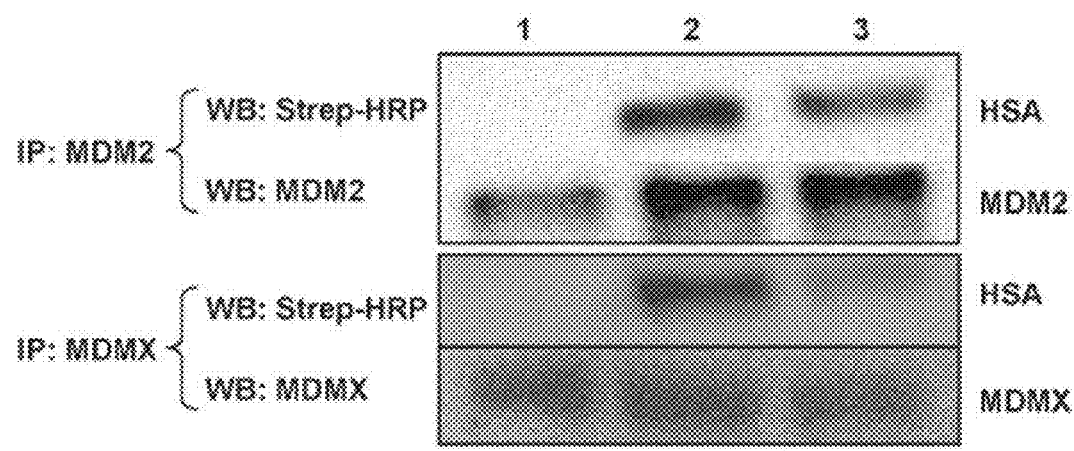

rHSA-P53i and rHSA-PMI promote cytotoxicity in SJSA-1 cells via caspase activation.

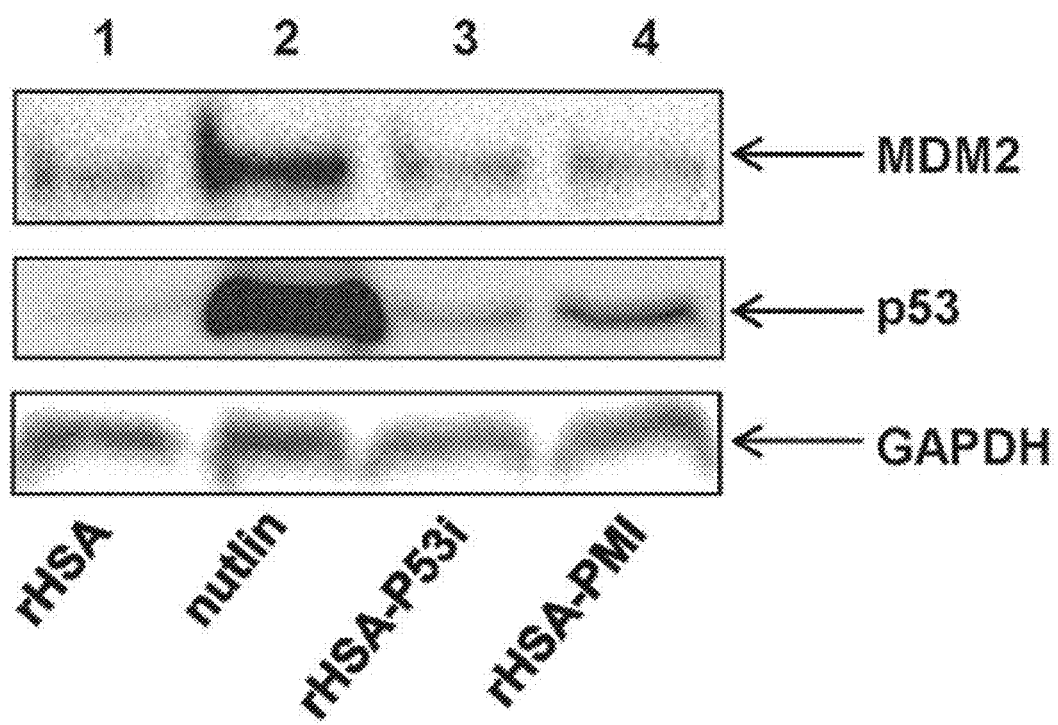
Figure 5. rHSA-P53i and rHSA-PMI induce p53 accumulation, but not MDM2.

rHSA fusion proteins are able to form stable complexes with FA-FITC.

rHSA/FA-FITC complexes retain internalization and cytotoxic activity.

Schematic diagram of rHSA-mediated co-delivery technology.

rHSA-P53i and rHSA-PMI bind to Bcl-xL and Mcl-1 rHSA-P53i reduces Bak-Bcl-xL interaction

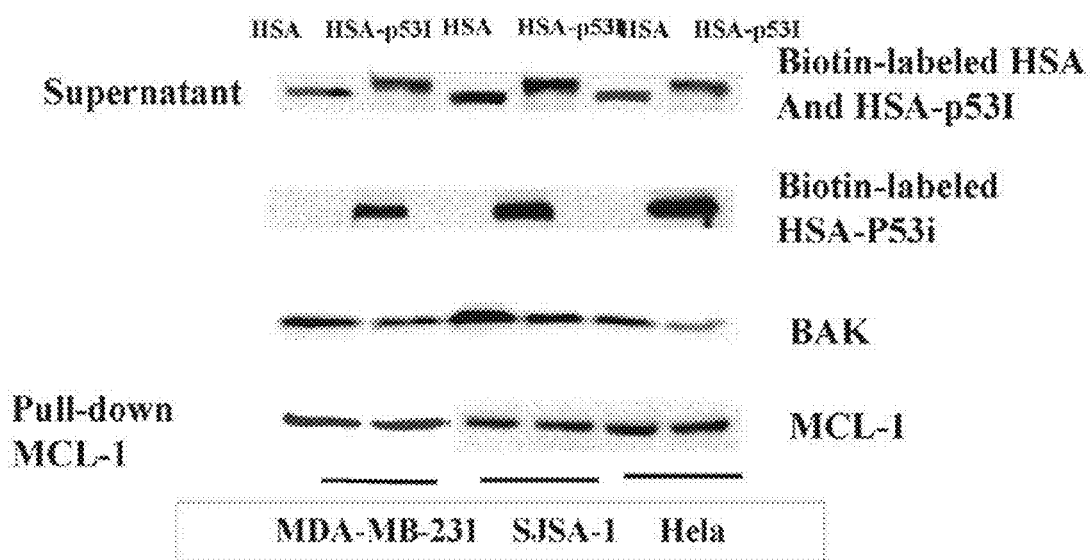
Figure 10D: rHSA-P53i reduces BAK-MCL-1 interaction

Figure 11. rHSA-P53i promotes release of cytochrome C.
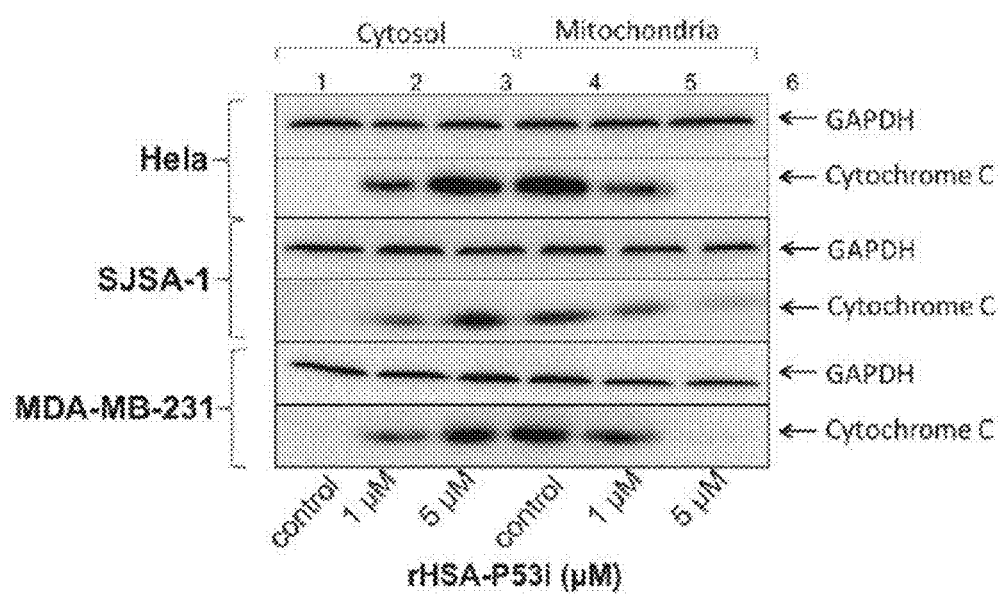

rHSA-P53i co-localizes with mitochondria in SJSA-1 and Hela cells

WT HSA

HSA-p53i

Co- localization of FITC-labeled WT HSA or HSA-p53i with mitochondria

SJSA-1

WT HSA

HSA-p53i

Co- localization of FITC-labeled WT HSA or HSA-p53i with mitochondria

HeLa

Cytotoxic activity of rHSA-P53i and rHSA-PMI is independent of p53 status

HSA-PMI has synergistic effect on SJSA-1 xenograft tumor model.

Co-Administration of Recombinant HSA-PMI and MTX Enhances Apoptosis Compared to Single Agent Administration in SJSA-1 Cells Synergistic efficacy of co-delivery rHSA-PMI and MTX Figure 15. Schematic representation of exemplary derivatives of p53-peptides or analogs

| | | |
|---|---|---|
| p53 peptide/ analog fused with | Transfer polypeptide<br><br>e.g.<br>Albumin,<br>Fc,<br>Transferrin<br>Or<br>Other proteins | |
| p53 peptide/ analog conjugated to | Transfer polypeptide<br><br>e.g.<br>Albumin,<br>Fc,<br>Transferrin<br>Or<br>Other proteins | and/ or | Polymers, Fatty acid Peptides,<br>Or<br>Other proteins<br><br>and /or<br>Nano/Microparticles, liposomes |

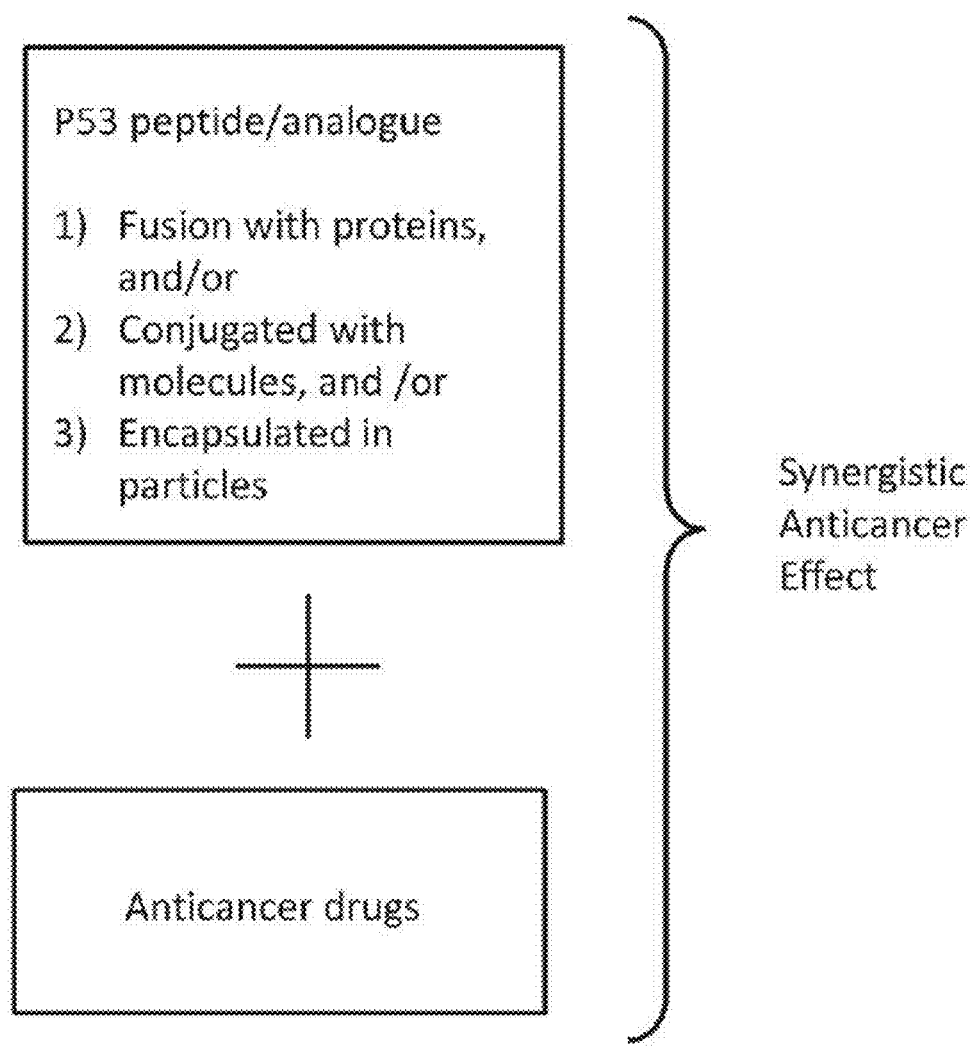
Figure 16. Exemplary Applications of p53-peptides or analogs

COMPOSITIONS COMPRISING SERUM ALBUMIN AND P53 PEPTIDES FUSION PROTEINS

RELATED APPLICATIONS

This application claims the benefit of priority to U.S. Provisional Application No. 62/083,010, filed on Nov. 21, 2014, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Nov. 19, 2015, is named B3497-00194_SL.txt and is 22,169 bytes in size.

FIELD OF THE INVENTION

The present invention relates to compositions useful in inhibiting Bcl-XL or MCL-1 and disrupting p53-MDM2 and p53-MDMX interactions, and methods of using those compositions for treating a subject for conditions, such as neoplastic disorders, including cancer, that are responsive to increasing p53-mediated cellular activities or promoting p53-independent apoptosis. In some aspects, the compositions of this invention relate to fusion polypeptides comprising a transporter polypeptide, such as human serum albumin, and a p53-agonist, which can be, in some aspects, a p53 peptide such as a p53 derived peptide and/or a p53 activating peptide, or a small molecule agonist.

BACKGROUND

Cancer is the general name for a group of more than 100 diseases, which are diagnosed in more than one million new patients in the United States each year. Although there are many kinds of cancer, they share a common feature: abnormal cancer cells either do not undergo efficient apoptosis, and/or are not effectively killed by the patient's immune system, leading to the uncontrolled growth of the abnormal cancer cells. Untreated cancers can cause serious illness and death. Although identification of risk factors, early detection, diagnosis, and treatment options have improved prognosis of many kinds of cancers, cancer remains a leading cause of death.

The p53 tumor suppressor protein plays a critical role in generating cellular responses to a number of stress signals, including DNA damage, aberrant proliferative signals due to oncogene activation, and hypoxia. Upon activation, p53 is stabilized and moves to the nucleus, where it binds to DNA in a sequence specific manner and promotes transcriptional regulation of genes involved in DNA repair, cell-cycle arrest, senescence, and apoptosis. While it is estimated that the p53 gene is mutated in 50% of tumors, increasing evidence reveals that a large percentage of tumors retain wild type p53, but possess other alterations in the p53 pathway, which prevents its critical tumor-suppressive function.

SUMMARY

In one aspect, the current invention relates to fusion polypeptides comprising a polypeptide, and a p53 agonist, e.g., a p53 peptide or small molecule agonist, for example, comprising a human serum albumin (HSA) polypeptide and a p53 peptide. In some aspects, p53 peptides of this invention are p53 derived peptides or p53 activating peptides, including analogs thereof. The p53 agonists of this invention are small molecule analogs of the p53 peptides, capable of inhibiting two or more targets from two essential cellular pathways involved in modulating apoptosis. In some aspects, the transporter polypeptide may be any natural or artificial polypeptide, including but not limited to, for example, animal serum albumin, including but not limited to a human serum albumin (HSA), or a fragment thereof, animal serum globulin, including but not limited to, an immunoglobulin, (an antibody) or antibody fragment polypeptide, such as an Ig-FC polypeptide, a transferrin polypeptide, an antennapedia peptide, cationic cell penetrating peptide (TAT), transportan and polyarginine. The fusion polypeptides of this invention have been shown to be transported into cells, and to surprisingly bind and interact with more than two target proteins involved in mediating apoptosis, including BCL-XL, MCL, MDM2, and MDMX. In some aspects, the fusion polypeptides inhibit BCL-XL and MCL and MDM2 and/or MDMX, for example, the fusion polypeptides may inhibit one or more of BCL-XL, MCL, MDM2 and MDMX. The BCL-XL and MCL proteins are mitochondrial transmembrane proteins that prevent caspase activation by inhibiting the release of mitochondrial contents such as cytochrome c, leading to inhibition of apoptosis. MDM2 and/or MDMX, which are overexpressed in many cancer cells, are E3 ubiquitin-protein ligases, that bind to and promote degradation of p53. In some aspects, the fusion polypeptides of this invention mediate apoptosis by binding to and disrupting and/or inhibiting the anti-apoptotic activity of BCL-XL and MCL. In one aspect, the fusion polypeptides of this invention also mediate tumor-suppressive functions, including apoptosis, by disrupting p53-interaction with MDM2 and/or MDMX, resulting in accumulation of p53 in the cell.

The fusion polypeptides undergo HSA mediated transport into cells, and, in some aspects of this invention, inhibit the apoptosis inhibitors BCL-XL and MCL, resulting in apoptosis regardless of p53 activity in the cell, e.g., p53-independent apoptosis activity. It has also surprisingly been found that the fusion polypeptides can mediate apoptosis and cytotixity in cells independent of the p53 genotype of the cell. Accordingly, in some aspects, the fusion polypeptides of this invention can mediate apoptosis and cytotixity in cells that are wild type for p53, as well as p53 mutant cells. p53 mutant cells include p53 negative cells, cells underexpressing p53. The fusion polypeptides of this invention also disrupt p53-MDM2 and/or p53-MDMX interactions, resulting in accumulation of cellular p53, which can then mediate apoptosis and induce cytotoxicity. In some aspects, cells underexpressing p53 may either express low levels of p53, or express a p53 with partial or complete loss of function, i.e., lower or apoptosis activity compared to wild-type p53, or may express low levels of p53. In some aspects, cells may overexpress p53, which may either express high levels of p53, or express a p53 with higher apoptosis activity than wild-type p53, or both.

In one aspect, this invention relates to fusion polypeptides which are first in a class of compounds surprisingly demonstrated herein to inhibit two or more targets from two essential cellular pathways involved in modulating the tumor-suppressive functions, including apoptosis. To the inventors' knowledge, no small molecule compounds have yet been shown to efficiently inhibit two or more targets involved in apoptosis.

In one aspect the current invention provides a method of inhibiting BCL-XL and MCL-1 in a cell, the method comprising (a) providing a fusion polypeptide or conjugate comprising a human serum albumin and a p53-peptide; and (b) contacting the cell with the fusion polypeptide, thereby inhibiting BCL-XL and MCL-1 inhibition of apoptosis. In some aspects inhibiting BCL-XL and MCL-1 disrupts BCL-XL and MCL-1 inhibition of apoptosis. In some aspects of this invention, the cell contacted with the fusion polypeptide is a cancer cell. It has been surprisingly demonstrated that the fusion polypeptides of this invention can inhibit and/or disrupt, the inhibition of apoptosis mediated by BCL-XL and MCL-1, regardless of the p53 genotype of the cell, which can be a cancer cell. In some aspects, the cell is a p53-wild type cancer cell. In some embodiments, the cell contacted with the fusion polypeptide or conjugate is a p53 mutant or a p53-negative cancer cell. In some aspects of this invention, the p53 mutant cancer cell contacted with the conjugate is a cancer cell expressing low levels of p53, or a cell expressing a p53 protein with lower BCL-XL/MCL-1 binding and/or lower apoptosis mediating activity than a wild-type p53 protein.

In some aspects of this invention, the fusion polypeptide used in the method of inhibiting BCL-XL and MCL-1 in a cell and disrupting BCL-XL and MCL-1 inhibition of apoptosis is a recombinant fusion protein comprising (a) a p53-derived peptide and a human serum albumin (HSA) polypeptide, or a fragment or variant of HSA; or (b) a p53-activating peptide and a human serum albumin. In some embodiments, the fusion polypeptide used in the method of inhibiting BCL-XL and MCL-1 in a cell, is a chemically cross-linked fusion polypeptide comprising (a) a p53-derived peptide and a human serum albumin; or (b) a p53-activating peptide and a human serum albumin. The HSA polypeptide may comprise HSA, or a fragment or variant of HSA which retains its cell transport and/or ligand binding properties, such as fatty acid binding. In some aspects, the HSA polypeptide may also comprise non peptide modifications. The antibody polypeptide, e.g., antibody fragment polypeptide such as IG-Fc may comprise an antibody, or a fragment or variant such as IG-Fc which retains cell transport and/or ligand binding properties. In some aspects, the antibody polypeptide may also comprise non peptide modifications. The transferrin polypeptide, e.g., may comprise transferrin, or a fragment or variant which retains cell transport and/or ligand binding properties. In some aspects, the transferrin polypeptide may also comprise non peptide modifications. In some aspects of this invention, p53 agonists, including p53-peptides, for example, p53-derived peptides and p53-activating peptides, or their peptidomimetic or small molecule analogs may be useful for the methods of this invention.

In some embodiments, the fusion polypeptide used in the method of inhibiting BCL-XL and MCL-1 in a cell comprises one or more anticancer agents, in addition to the p53-derived peptide and a human serum albumin polypeptide. In some embodiments, the anticancer agent is chemically conjugated to a natural ligand of human serum albumin. In some embodiments, the additional anticancer agent is covalently bound to the a human serum albumin. In some embodiments, the additional anticancer agent is bound to a human serum albumin polypeptide through non-covalent interactions. In some embodiments, the anticancer agent is bound to a fatty acid which is a natural ligand of human serum albumin. In some embodiments, the additional anticancer agent is selected from the group consisting of 2,3,4,5,6-pentafluoro-N-(3-fluoro-4-methoxyphenyl)benzene sulfonamide, abiraterone acetate, afatinib, aldesleukin, alemtuzumab, alitretinoin, altretamine, amifostine, aminoglutethimide, anagrelide, anastrozole, anhydrovinblastine, arsenic trioxide, asparaginase, auristatin, azacitidine, azathioprine, bendamustine, bevacizumab, bexarotine, bicalutamide, bleomycin, BMS 184476, bortezomib, busulfan, cachectin, capecitabine, carboplatin, carmustine, cemadotin, cetuximab, chlorambucil, cisplatin, cladribine, crizotinib, cyclophosphamide, cytarabine, dacarbazine, dactinomycin, dasatinib, daunorubicin, denileukin diftitox, decitabine, 3',4'-didehydro-4'-deoxy-8'-norvin-caleukoblastine, N,N-dimethyl-L-valyl-L-valyl-N-methyl-L-valyl-L-proly-1-Lproline-t-butylamide (SEQ ID NO: 5), docetaxel, dexamethasone, doxifluridine, doxorubicin, epirubicin, epoetin alpha, epothilone, erlotinib, estramustine, etinostat, etoposide, everolimus, exemestane, filgrastim, floxuridine, fludarabine, fluorouracil, fluoxymesterone, flutamide, folate linked alkaloids, gefitinib, gemcitabine, gemtuzumab ozogamicin, GM-CT-01, goserelin, hexamethylmelamine, hydroxyureas, ibritumomab, idarubicin, ifosfamide, imatinib, interferon alpha, interferon beta, irinotecan, ixabepilone, lapatinib, leucovorin, leuprolide, lenalidomide, letrozole, lomustine, mechlorethamine, megestrol, melphalan, mercaptopurine, methotrexate, mitomycin, mitoxantrone, nelarabine, nilotinib, nilutamide, octreotide, ofatumumab, oprelvekin, oxaliplatin, paclitaxel, panitumumab, pemetrexed, pentostatin, polysaccharide galectin inhibitors, procarbazine, raloxifene, retinoic acids, rituximab, romiplostim, sargramostim, sorafenib, streptozocin, sunitinib, tamoxifen, temsirolimus, temozolamide, teniposide, thalidomide, thioguanine, thiotepa, tioguanine, topotecan, toremifene, tositumomab, trametinib, trastuzumab, tretinoin, valrubicin, vegf inhibitors and traps, vinblastine, vincristine, vindesine, vinorelbine, vintafolide, vorinostat, and a combination thereof.

In some aspects of this invention, inhibiting BCL-XL and MCL-1 in a cell using the methods of this invention leads to death of the contacted cell. In some aspects of this invention, death of the cell contacted with the fusion polypeptide occurs by apoptosis. It has been surprisingly demonstrated that the fusion polypeptides of this invention can mediate apoptosis of the contacted cell, occurs independent of p53 the genotype of the cell. For example, the cancer cell may be selected from the group consisting of (a) a p53-positive cancer cell, (b) a p53 mutant cancer cell, (c) p53-negative cancer cell, and (d) a cancer cell expressing low levels of p53, or low activity p53. In some aspects, the methods further comprise disrupting p53-MDM2 and/or p53-MDMX interactions. In some aspects, where the cells have a functional p53 genotype/phenotype, disrupting p53-MDM2 and/or p53-MDMX leads to accumulation of p53 in cells, which mediates apoptosis. In addition, the p53 peptide portion of the fusion polypeptide is also surprisingly shown to be capable of mediating apoptosis by inhibiting BCL-XL and MCL-1. In some embodiments, cell death of the contacted cell occurs by apoptosis.

In another aspect the current invention provides a method of inducing cell death by disrupting BCL-XL or MCL-1 interactions with BAK and/or by disrupting p53-MDM2 and/or p53-MDMX interaction, the method comprising (a) providing a fusion polypeptide comprising a human serum albumin polypeptide, and a p53-peptide; and (b) contacting the cell with the fusion polypeptide. In some embodiments, the cell may be selected from the group consisting of (a) a p53-positive cancer cell, (b) a p53 mutant cancer cell, (c) p53-negative cancer cell, and (d) a cancer cell expressing low levels of p53, or low activity p53. In some embodiments, the fusion polypeptide is (a) a recombinant fusion protein comprising a p53-derived peptide and a human serum albumin polypeptide, (b) a recombinant fusion protein comprising a p53-activating peptide and a human serum albumin polypeptide, (c) a chemically cross-linked fusion polypeptide comprising a p53-derived peptide and human serum albumin, or (d) a chemically cross-linked fusion polypeptide comprising a p53-activating peptide and a human serum albumin polypeptide.

In another aspect, the current invention provides a method of treating a subject afflicted with a condition responsive to inhibiting BCL-XL, and MCL-1 and disrupting p53-MDM2 and/or p53-MDMX interaction, the method comprises (a) administration of therapeutically effective amount of a fusion polypeptide comprising (i) a human serum albumin and a p53-peptide. The p53-peptide is a p53 derived peptide and/or a p53-activating peptide. In some embodiments, the subject is a human. In some embodiments, the condition responsive to inhibiting BCL-XL, and MCL-1 and disrupting p53-MDM2 and/or p53-MDMX interaction is a neoplastic condition. In some embodiments, the condition responsive to inhibiting BCL-XL, and MCL-1 and disrupting p53-MDM2 and/or p53-MDMX interaction is a cancer.

In some embodiments, the fusion polypeptide, used in the methods of treating a condition responsive to inhibiting BCL-XL, and MCL-1 and disrupting p53-MDM2 and/or p53-MDMX interaction, further comprises one or more anticancer agents.

Thus, in some aspects, this invention also relates to: 1) making, screening and using p53-peptides optimized to inhibit BCL and MCL-1, and to disrupt p53-MDM2 and/or p53-MDMX interactions, in cancer therapy, regardless of the p53 genotype of the cancer cells; 2) developing small molecule compounds to mimic the function of p53-derived peptides and target p53 transcription dependent and independent pathways simultaneously; 3) combining p53-derived peptides or their analogues with anticancer chemotherapeutics for synergistic efficacy. In vivo mouse tumor model study showed that albumin-p53 activating peptide fusion protein can significantly boost the efficacy of MTX.

In some aspects, this invention relates to a pharmaceutical composition comprising a transporter protein and a p53 peptide such as a p53 derived peptide and/or a p53 activating peptide, optionally further comprising a small molecule drug. In some embodiments, the transporter polypeptide may be any natural or artificial polypeptide, including but not limited to, for example, animal serum albumin, including but not limited to a human serum albumin (HSA) polypeptide, e.g., human serum albumin or a fragment or variant thereof, animal serum globulin, including but not limited to, an immunoglobulin, (an antibody) or antibody fragment polypeptide, such as an Ig-FC polypeptide, a transferrin polypeptide, an antennapedia peptide, cationic cell penetrating peptide (TAT), transportan and polyarginine. In some embodiments, this invention relates to a pharmaceutical composition for treating a neoplastic disorder in an animal. In some embodiments, the neoplastic disorder is a cancer. In some embodiments, the animal is a human. In some embodiments, the composition optionally includes one or more of pharmaceutically acceptable excipients, including but not limited to solvents, buffers, binders, disintegrants, fillers, glidants and lubricants. In some embodiments, the pharmaceutical composition is formulated as a capsule, tablet, pellet, dragee, semi-solid, powder, granule, suppositorie, ointment, cream, lotion, inhalant, injection, cataplasm, gel, tape, eye drop, solution, syrup, aerosol, suspension, emulsion, or lyophilisate.

In some aspects, this invention relates to use of a fusion polypeptide comprising a transporter protein and a p53 peptide such as a p53 derived peptide and/or a p53 activating peptide, and optionally a small molecule drug, for the manufacture of a medicament for treating, alleviating or preventing symptoms associated with a neoplastic disorder in an animal. In some embodiments, the transporter polypeptide may be any natural or artificial polypeptide, including but not limited to, for example, animal serum albumin, including but not limited to human serum albumin (HSA), or a fragment thereof, animal serum globulin, including but not limited to, an immunoglobulin, (an antibody) or antibody fragment polypeptide, such as an Ig-FC polypeptide, a transferrin polypeptide, an antennapedia peptide, cationic cell penetrating peptide (TAT), transportan and polyarginine. In some embodiments, the neoplastic disorder is a cancer. In some embodiments, the animal is a human. In some embodiments, the medicament optionally includes one or more of pharmaceutically acceptable excipients, including but not limited to solvents, buffers, binders, disintegrants, fillers, glidants and lubricants. In some embodiments, the medicament is formulated as a capsule, tablet, pellet, dragee, semi-solid, powder, granule, suppositorie, ointment, cream, lotion, inhalant, injection, cataplasm, gel, tape, eye drop, solution, syrup, aerosol, suspension, emulsion, or lyophilisate.

BRIEF DESCRIPTION OF THE DRAWINGS

FIG. 1A: rHSA/peptide fusion protein was constructed by fusing either P53i (SEQ ID NO: 1) or PMI (SEQ ID NO: 2) peptide sequence to the C-terminal of HSA. A caspase cleavage site (DEVDG (SEQ ID NO: 6)) was included as a linker between HSA and peptide. FIG. 1B: Fusion proteins were expressed using Pichia pastoris yeast expression system and purified by cibacron blue dye agarose as described in Methods. Lane 1 contains 10 µl of pre-stained Rec protein ladder (Fischer). Lanes 2 and 3 contain 10 µg of purified rHSA-p53i and rHSA-PMI, respectively. Proteins were visualized by Coomassie blue staining, revealing >95% purity and MW of approximately 70 kD.

FIG. 2A, FIG. 2B, and FIG. 2C shows that rHSA-p53 and rHSA-PMI are efficiently taken up into SJSA-1 cells. FITC-labeled rHSA (5 µM), FITC-rHSA-P53i (5 µM), and FITC-rHSA-PMI (5 µM) were added to SJSA-1 cells as described in Methods. Visualization at 60× magnification revealed efficient uptake of FITC-rHSA (FIG. 2A), FITC-rHSA-P53i (FIG. 2B) and FITC-rHSA-PMI (FIG. 2C) occurred following 24-hour incubation. FITC staining of vesicular cargo suggests significantly greater uptake of rHSA-P53i and rHSA-PMI, compared to rHSA.

FIG. 3 shows that rHSA-P53i and rHSA-PMI bind to MDM2 and MDMX. To detect the interaction between MDM2/MDMX and rHSA fusion proteins, 4 µg each of biotinylated rHSA (lane 1), rHSA-P53i (lane 2), or rHSA-PMI (lane 3) were added to 200 µg of SJSA-1 whole cell lysate. MDM2 or MDMX antibody was added to the lysate followed by pulling down MDM2/MDMX and rHSA complexes using Protein A/G (1:1) resins. Samples were then analyzed by SDS-PAGE and Western blotting using MDM2, MDMX, and Streptavidin-HRP (Strep-HRP) antibodies.

FIG. 4A). Cytotoxicities were measured by CyQuant Assay and normalized according to 10 µM rHSA-treated cells. FIG. 4B). Caspase activation was quantitated using the Homogeneous Caspase Assay as described in Methods and normalized according to untreated cells. Results are displayed as percent cell death (FIG. 4A) or fold change (FIG. 4B) relative to 10 µM rHSA-treated wells. Data are representative of 3 independent experiments performed in triplicate. Error bars indicate ± SD.

FIG. 5 shows that rHSA-P53i and rHSA-PMI induce p53 accumulation, but not MDM2. SJSA-1 cells were plated and allowed to attach overnight. On day 2, culture media with 10 µM rHSA (lane 1), 10 µM nutlin (lane 2), 10 µM rHSA-P53i (lane 3), or 10 µM rHSA-PMI (lane 4) were added to respective wells and allowed to incubate for 24 hrs. Cells were then washed, lysed and immunoblotted for p53 and MDM2. Western blot analysis to detect p53 protein (middle panel) reveals treatment with rHSA-P53i or rHSA-PMI resulted in modest accumulation of p53. Densitometry analysis reveals p53 accumulation following rHSA-P53i and rHSA-PMI treatment is on average, 1.5 and 2.9 orders of magnitude above control wells, respectively. As expected, nutlin-treatment promotes robust p53 accumulation (11.5-fold average increase). However, unlike nutlin, which promotes a 5-fold increase in MDM2 expression, MDM2 protein remained at basal levels following treatment with rHSA-P53i or rHSA-PMI (1.1- and 1.0-fold change, respectively).

FIG. 6A). rHSA-PMI (lane 1-3), rHSA-P53i (lane 4-6) and rHSA (lane 7-9) were incubated at the indicated molar ratios (rHSA:FA-FITC) with FA-FITC (lane 1, 4, and 7 (1:1); lane 2, 5, and 8 (1:2); lane 3, 6, and 9 (1:4); lane 10, FA-FITC only). The upper band in the gel corresponds to the HSA/FA-FITC complex, while the lower band indicates unbound FA-FITC. Incorporation of FA-FITC into rHSA was achieved up to a 1:4 rHSA:FA-FITC molar ratio. FIG. 6B). rHSA/FA-FITC complexes were pre-formed at a 1:4 molar ratio (HSA:FA-FITC; 30 pmol:120 pmol) as described in Methods. Unlabeled FA was then added at the indicated concentrations to mimic the competition of free FA present under physiological conditions. The minimal dissociation of FA-FITC from pre-formed rHSA/FA-FITC complexes at the 8 times excess concentration of unlabeled FA (lane 8) indicates FA-FITC and rHSA complex was highly stable in the presence of free FA.

FIG. 7A). FITC-labeled rHSA (5 µM), FIG. 7B). rHSA/FA-FITC (5 µM/10 µM), and FIG. 7C). FA-FITC (10 µM) were added to SJSA-1 cells as described in Methods. Visualization at 60× magnification revealed efficient uptake of FITC-rHSA, rHSA/FA-FITC and FA-FITC occurred following 24-hour incubation. The extent of FITC staining observed in rHSA/FA-FITC-treated cells is similar to that of FA-FITC treatment alone indicating FA-FITC modification does not impair internalization of rHSA.

FIG. 11 shows that rHSA-P53i attenuates Bak-Bcl-XL or MCL-1 interaction and promotes release of cytochrome c. HSA-p53i triggers apoptosis by releasing cytochrome C from mitochondria to cytoplasm in cell lines. Cytosol cytochrome C is able to induce apoptosis.

FIG. 14A and FIG. 14B show that co-administration of recombinant HSA-PMI and MTX enhances apoptosis compared to single agent administration in SISA-1 cells. FIG. 14C shows the synergistic efficacy of co-delivery rHSA-PMI and MTX.

FIG. 15 shows a schematic of exemplary p53 agonist-transporter polypeptide compositions of this invention.

FIG. 16 shows a schematic of exemplary uses of the p53 agonists of this invention for the treatment of cancer and synergistic anti-cancer effects.

DETAILED DESCRIPTION

Figure 1A:
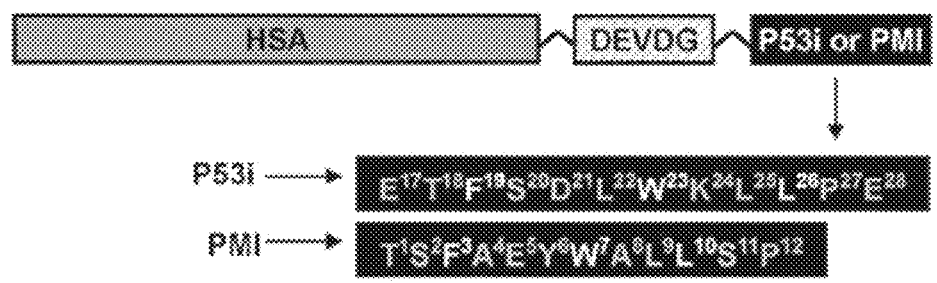
FIG. 1A and FIG. 1B shows design and purification of rHSA-P53i and rHSA-PMI.

The current invention is based, in part, on our discovery that the p53 agonists of this invention, for example, p53 peptides (not active p53), can bind and interact with several targets including, but not limited to, MDM2, MDMX, BCL-XL, MCL p53 itself and MDM2, and induce cytotoxicity independent on p53 genotype (wild type, mutation, or deletion).

In one aspect the current invention provides a method of inhibiting BAK-XL and MCL-1 in a cell, for example, by disrupting the BAK-BCL-XL or BAK-MCL-1 interaction in a cell, the method comprising (a) providing a fusion polypeptide comprising a transporter polypeptide and a p53-agonist; and (b) contacting the cell with the fusion polypeptide. In one aspect, the p53 agonist component of the fusion polypeptide is, in some aspects, a p53 peptide or small molecule agonist, for example, a p53 peptide, such as a p53 derived peptide or a p53 activating peptide, including peptide or peptidomimetic analogs thereof, or small molecule analogs thereof. The p53 agonists of this invention are capable of inhibiting two or more targets from two essential cellular pathways involved in modulating apoptosis. In some aspects, the transporter polypeptide is, for example, an HSA polypeptide, an antibody or antibody fragment polypeptide, such as an Ig-FC polypeptide, a transferrin polypeptide, an antennapedia peptide, cationic cell penetrating peptide (TAT), transportan and polyarginine. In one aspect the current invention provides a method of inhibiting BAK-XL and MCL-1 in a cell, for example, by disrupting the BAK-BCL-XL or BAK-MCL-1 interaction in a cell, the method comprising (a) providing a fusion polypeptide comprising a human serum albumin, and a p53-peptide; and (b) contacting the cell with the fusion polypeptide.

In one aspect, the instant disclosure provides a method of inhibiting BAK-XL and MCL-1 in a cell and inducing cell death in a cell, the method comprising (a) providing a fusion polypeptide comprising a transporter polypeptide and a p53-agonist; and (b) contacting the cell with the fusion polypeptide. In one aspect, the p53 agonist component of the fusion polypeptide is, in some aspects, a p53 peptide or small molecule agonist, for example, a p53 peptide, such as a p53 derived peptide or a p53 activating peptide, including peptide or peptidomimetic analogs thereof, or small molecule analogs thereof.

In one aspect, the instant disclosure provides a method of interaction between p53-MDM2 or p53-MDMX, the method comprising (a) providing a fusion polypeptide comprising a transporter polypeptide and a p53-agonist; and (b) contacting the cell with the fusion polypeptide. In one aspect, the p53 agonist component of the fusion polypeptide is, in some aspects, a p53 peptide or small molecule agonist, for example, a p53 peptide, such as a p53 derived peptide or a p53 activating peptide, including peptide or peptidomimetic analogs thereof, or small molecule analogs thereof.

In one aspect, the instant disclosure provides a method of interaction between p53-MDM2 or p53-MDMX and inducing cell death in a cell, the method comprising (a) providing a fusion polypeptide comprising a transporter polypeptide and a p53-agonist; and (b) contacting the cell with the fusion polypeptide. In one aspect, the p53 agonist component of the fusion polypeptide is, in some aspects, a p53 peptide or small molecule agonist, for example, a p53 peptide, such as a p53 derived peptide or a p53 activating peptide, including peptide or peptidomimetic analogs thereof, or small molecule analogs thereof.

In one aspect, the instant disclosure provides a method of inhibiting BAK-XL and MCL-1 in a cell, and inhibiting the interaction between p53-MDM2 or p53-MDMX, the method comprising (a) providing a fusion polypeptide comprising a transporter polypeptide and a p53-agonist; and (b) contacting the cell with the fusion polypeptide. In one aspect, the p53 agonist component of the fusion polypeptide is, in some aspects, a p53 peptide or small molecule agonist, for example, a p53 peptide, such as a p53 derived peptide or a p53 activating peptide, including peptide or peptidomimetic analogs thereof, or small molecule analogs thereof.

In one aspect, the instant disclosure provides a method of inhibiting BAK-XL and MCL-1 in a cell, and inhibiting the interaction between p53-MDM2 or p53-MDMX and inducing cell death in a cell, the method comprising (a) providing a fusion polypeptide comprising a transporter polypeptide and a p53-agonist; and (b) contacting the cell with the fusion polypeptide. In one aspect, the p53 agonist component of the fusion polypeptide is, in some aspects, a p53 peptide or small molecule agonist, for example, a p53 peptide, such as a p53 derived peptide or a p53 activating peptide, including peptide or peptidomimetic analogs thereof, or small molecule analogs thereof.

In one aspect, the instant disclosure provides a method of inducing cell death in a cell, the method comprising (a)

providing a fusion polypeptide comprising a transporter polypeptide and a p53-agonist; and (b) contacting the cell with the fusion polypeptide. In one aspect, the p53 agonist component of the fusion polypeptide is, in some aspects, a p53 peptide or small molecule agonist, for example, a p53 peptide, such as a p53 derived peptide or a p53 activating peptide, including peptide or peptidomimetic analogs thereof, or small molecule analogs thereof.

In one aspect, the instant disclosure provides a method of treating a subject with cancer responsive to p53 inhibition of BCL-XL and MCL-1, and disrupting p-53 MDM2 interactions, the method comprising (a) providing a fusion polypeptide comprising a transporter polypeptide and a p53-agonist; and (b) contacting the cell with the fusion polypeptide. In one aspect, the p53 agonist component of the fusion polypeptide is, in some aspects, a p53 peptide or small molecule agonist, for example, a p53 peptide, such as a p53 derived peptide or a p53 activating peptide, including peptide or peptidomimetic analogs thereof, or small molecule analogs thereof.

In some embodiments, the instant disclosure provides a method of treating a subject with cancer is selected from the group consisting of Acute Lymphoblastic Leukemia (ALL), acute myeloid leukemia, adrenocortical carcinoma, AIDS-related cancers, AIDS-related lymphoma, anal cancer, appendix cancer, astrocytoma, childhood cerebellar or cerebral cancer, basal-cell carcinoma, bile duct cancer, bladder cancer, bone tumor, osteosarcoma/malignant fibrous histiocytoma, brainstem glioma, brain cancer, brain tumor, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, Burkitt's lymphoma, carcinoid tumor, childhood tumor, carcinoid tumor, gastrointestinal, carcinoma of unknown primary, central nervous system lymphoma, primary, childhood cerebellar astrocytoma, childhood cerebral astrocytoma/malignant glioma, cervical cancer, cholangiocarcinoma, chondrosarcoma, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, ewing's sarcoma in the ewing family of tumors, childhood extracranial germ cell tumor, extragonadal germ cell tumor, extrahepatic bile duct cancer, intraocular melanoma, eye cancer, retinoblastoma, gallbladder cancer, gastric (stomach) cancer, gastrointestinal carcinoid tumor, gastrointestinal stromal tumor (GIST), germ cell tumor, extracranial germ cell tumor, extragonadal germ cell tumor, ovarian germ cell tumor, gestational trophoblastic tumor, glioma of the brain stem, glioma, childhood cerebral astrocytoma, glioma, visual pathway and hypothalamic cancer, gastric carcinoid cancer, hairy cell leukemia, head and neck cancer, heart cancer, hepatocellular (liver) cancer, Hodgkin lymphoma, non-Hodgkin lymphoma, hypopharyngeal cancer, hypothalamic and visual pathway glioma, intraocular melanoma, islet cell carcinoma (e.g. endocrine, pancreatic), Kaposi sarcoma, kidney cancer (renal cell cancer), laryngeal cancer, leukaemia, acute lymphoblastic leukaemia (also called acute lymphocytic leukaemia), acute myeloid leukaemia (also called acute myelogenous leukemia), chronic lymphocytic leukaemia (also called chronic lymphocytic leukemia), chronic myelogenous leukemia (also called chronic myeloid leukemia), hairy cell leukemia, lip and oral cavity cancer, liposarcoma, liver cancer (primary), lung cancer, non-small cell lung cancer, small cell lung cancer, AIDS-related lymphoma, Burkitt lymphoma, cutaneous T-cell lymphoma, Hodgkin lymphoma, non-Hodgkin lymphoma (an old classification of all lymphomas except Hodgkin's), primary central nervous system cancer, macroglobulinemia, Waldenström, male breast cancer, malignant fibrous histiocytoma of bone/osteosarcoma, medulloblastoma, melanoma, melanoma, intraocular (eye) cancer, merkel cell cancer, mesothelioma, adult malignant mesothelioma, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia, chronic, myeloid leukemia, adult acute, myeloid leukemia, childhood acute myeloma, multiple myeloma, chronic myeloproliferative disorder, myxoma, nasal cavity and paranasal sinus cancer, nasopharyngeal carcinoma, neuroblastoma, non-small cell lung cancer, oligodendroglioma, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic islet cell cancer, paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter, transitional cell cancer, retinoblastoma, rhabdomyosarcoma, salivary gland cancer, sarcoma, ewing family of tumors, sarcoma, kaposi, sarcoma, soft tissue, sarcoma, uterine, sézary syndrome, skin cancer (non-melanoma), skin cancer (melanoma), skin carcinoma, merkel cell, small cell lung cancer, small intestine cancer, soft tissue sarcoma, squamous cell carcinoma, squamous neck cancer with occult primary, metastatic, stomach cancer, supratentorial primitive neuroectodermal tumor, T-cell lymphoma, cutaneous fungoides and sézary syndrome, testicular cancer, throat cancer, thymoma, thymoma and thymic carcinoma, thyroid cancer, thyroid cancer, transitional cell cancer of the renal pelvis and ureter, trophoblastic tumor, gestational, carcinoma of unknown primary site, cancer of unknown primary site, transitional cell cancer, urethral cancer, uterine cancer, endometrial, uterine sarcoma, vaginal cancer, visual pathway and hypothalamic glioma, childhood cancer, vulvar cancer, waldenström macroglobulinemia, and Wilms tumor (kidney cancer).

In some aspects, this disclosure relates to use of a fusion polypeptide described herein, and optionally further small molecule drug, for the manufacture of a medicament for treating, alleviating or preventing symptoms associated with a neoplastic disorder in an animal. In some embodiments, the transporter polypeptide may be any natural or artificial polypeptide, described above, including but not limited to, for example, animal serum albumin, polypeptide, including but not limited to a human serum albumin (HSA) polypeptide, or a fragment or variant thereof, animal serum globulin, including but not limited to, an immunoglobulin, (an antibody) or antibody fragment polypeptide, such as an Ig-FC polypeptide, a transferrin polypeptide, an antennapedia peptide, cationic cell penetrating peptide (TAT), transportan and polyarginine. In some embodiments, the neoplastic disorder is a cancer. In some embodiments, the animal is a human. In some embodiments, the medicament optionally includes one or more of pharmaceutically acceptable excipients, including but not limited to solvents, buffers, binders, disintegrants, fillers, glidants and lubricants. In some embodiments, the medicament is formulated as a capsule, tablet, pellet, dragee, semi-solid, powder, granule, suppositorie, ointment, cream, lotion, inhalant, injection, cataplasm, gel, tape, eye drop, solution, syrup, aerosol, suspension, emulsion, or lyophilisate.

The fusion polypeptides of this invention have been shown to be transported into cells, and to surprisingly bind and interact with four proteins involved in mediating apoptosis, from two essential cellular pathways involved in modulating apoptosis, including BCL-XL, MCL-1, MDM2, and MDMX. In some embodiments, the fusion polypeptides are transported into the cell via HSA transport mechanisms.

In some embodiments, the fusion polypeptides of this invention surprisingly inhibit two or more targets from two essential cellular pathways involved in modulating apoptosis, for example, more than two targets from two essential cellular pathways involved in modulating apoptosis.

The p53 protein, a major cellular tumor suppressor, is situated at the crossroads of a network of signaling pathways that are essential for cell growth regulation and apoptosis induced by genotoxic and non-genotoxic stresses. In unstressed normal cells, the level of p53 protein is regulated by binding of proteins such as MDM2 and MDMX that promote p53 degradation. After genotoxic stress, p53 protein accumulates, in part, because the inhibition of interaction of p53 with proteins such as MDM2 and MDMX and resulting downregulation of degradation of p53. p53 also gets activated and promotes it DNA repair, cell-cycle arrest, senescence, and apoptosis.

MDM2 and/or MDMX, which are overexpressed in many cancer cells. MDM2 stands for mouse double minute 2 homolog, but the name "MDM2," or "Mdm2" also encompasses other mammalian homologs, including human homolog. MDM2 protein is an E3 ubiquitin-protein ligase that specifically binds the N-terminal trans-activation domain (TAD) of the p53 protein and thereby promotes ubiquitination and degradation of p53 protein. In addition, Mdm2 protein also functions as an inhibitor of p53 transcriptional activation. In some aspects, the fusion polypeptides of this invention mediate the tumor-suppressive functions, including apoptosis by disrupting p53-interaction with one or more of MDM2, MDMX and other proteins that mediate p53 degradation, resulting in accumulation of p53 in the cell. In some embodiments, the fusion polypeptides of this invention further inhibit the antiapoptotic activity of BAK-XL, MCL-1, or their homologs, orthologs or paralogs, for example, by disrupting the BAK-BCL-XL or BAK-MCL-1 interaction.

The BCL-XL, MCL and related proteins are mitochondrial transmembrane proteins that prevent caspase activation by inhibiting the release of mitochondrial contents such as cytochrome c, leading to inhibition apoptosis. BCL-2, BCL-XL and related proteins promote the survival of neoplastic cell, in disorders including cancer and polycythemia vera. BCL-2 and BCL-XL may become overactive due to mutations in them or other genes such as Jak2 mutations lead to over-activation of intracellular signaling molecules, such as Stat5, which lead to transcription of Bcl-xL gene. In some aspects, the fusion polypeptides of this invention mediate apoptosis by binding to and disrupting and/or inhibiting the anti-apoptotic activity of inhibiting BAK-XL, MCL-1, or their homologs, orthologs or paralogs in a cell, for example, by disrupting the BAK-BCL-XL or BAK-MCL-1 interaction.

In some aspects, p53 peptides of this invention are p53 derived peptides or p53 activating peptides, including analogs thereof. In some embodiments, the invention provides fusion peptides comprising a transporter polypeptide and one or more p53 peptide, p53 activating peptides or small molecule agonists or inhibitors described herein. In some embodiments, the p53 agonists of this invention are small molecule analogs of the p53 peptides, capable of inhibiting two or more targets from two essential cellular pathways involved in modulating apoptosis. In some aspects, the fusion polypeptides inhibit BCL-XL and MCL and MDM2 and/or MDMX, for example, the fusion polypeptides may inhibit one or more of BCL-XL, MCL, MDM2 and MDMX. In some embodiments, the p53 peptides or small molecule agonist of this invention are derived using in vitro evolution for optimized binding to one or more of p53, BCL-XL, MCL, MDM2, MDMX, their orthologs, paralogs, homologs, analogs and disrupting interaction between them, using or coupled with techniques like peptide display, phage display, mRNA display, ribosome display and the like. In some embodiments, the p53 peptides or small molecule agonists of this invention include peptides, peptide nucleic acids, nucleic acids and their analogs.

The p53 agonists, e.g., p53 peptides or p53 small molecule agonists, comprising the fusion polypeptides are capable of binding to two or more targets from two essential cellular pathways involved in modulating apoptosis. For example, in some embodiments, the p53 agonists, e.g., p53 peptides or p53 small molecule agonists, comprising the fusion polypeptides are capable of binding to BCL-XL, MCL, and/or to three or more of BCL-XL, MCL-1, MDM2, and MDMX. For example, the p53 peptides in some embodiments, bind to BCL-XL and MCL-1, as well as to MDM2 and/or MDMX. In some embodiments, the "p53 peptide" may comprise a p53 peptide, for example, a peptide corresponding to amino acids 17-28 of the p53 protein (ETFSDLWKLLPE, SEQ ID NO:1). In some embodiments, the "p53 peptide" may comprise a p53 activating peptide, for example, TSFAEYWALLSP, SEQ ID NO:2.

In some embodiments, the p53-derived peptide is homologous or identical to two or more contiguous amino acids of a region of p53 selected from the group consisting of activation domain 1 (amino acids 1-42), nuclear exclusion domain (amino acids 11-27), Highly Conserved Domain I (amino acids 13-23), activation domain 2 (amino acids 43-92), proline rich domain (amino acids 64-92), DNA binding domain (amino acids 101-300), transcriptional activation domains (amino acids 1-42 or 55-75), MDM2 binding domain, RPA binding domain, p62/TfB1 binding site (a subunit of TFIIH), nuclear localization signaling domain (amino acids 316-325), homo-oligomerisation domain (amino acids 307-355) or the negative regulatory domain (amino acids 356-393). In some embodiments, the p53-derived peptide may comprise one, two, three, four, five, six, seven, eight, nine or ten amino acid substitutions.

The p53 peptides of this invention are peptides are not full length active p53. In some embodiments, the p53 peptide comprises a peptide of length about 4 to about 100 amino acids homologous or identical to stretch of a vertebrate p53 peptide. For example, the p53-derived peptide may comprise, about 4-6, about 5-10, about 8-12, about 10-15, about 12-18, about 15-20, about 18-30, about 20-40, about 25-50, about 30-60, about 40-80, about 50-100 amino acids. In some embodiments, the peptides may comprise from 6 to 40 amino acids of p53, for example, from about 6 to about 35, from about 8 to about 35, from about 10 to about 35, from about 10 to about 25, from about 10 to 20, about 10, 11, 12, 13, 14, 15, 16, 17, 18, 19, 20, or any range of amino acids between any two of the recited numbers, from p53. In some embodiments, the p53-derived peptide is homologous or identical to one or more of human, mouse, rat, pig, cow, monkey, horse, cat, dog, or chicken p53, or p53 from other domesticated, zoo, or aquatic mammals.

Examples of p53-derived peptide include but are not limited to FSDLWKLL (amino acids 19-26 of the p53 protein, SEQ ID NO:3), ETFSDLWKLLPE (amino acids 17-28 of the p53 protein, SEQ ID NO:4).

The "p53 peptides" of this invention may also be peptidomimetic compounds, or variants or analogs of peptides from regions of p53, or be modified or derived from p53 peptides. In some embodiments, the p53-peptide may comprise non-naturally occurring amino acids. In some embodiments, the p53-peptide may comprise additional amino acids useful for one or more of spacer with another peptide, for altering stability, for altering solubility, for altering hydrophilicity/hydrophobicity, for altering membrane permeability, for altering folding characteristics.

In some embodiments, the p53-peptide may be "derived" by an in vitro screen for inhibition of a p53 function even if the p53 peptide is not designed based directly or entirely on a sequence from p53. The p53 peptides comprising the fusion polypeptides may be capable of binding to BCL-XL, MCL, to three or more of BCL-XL, MCL, MDM2, and MDMX, or to three or more proteins mediating apoptosis. In some embodiments, the p53-peptide may be derived from p53 itself. In some embodiments, the a p53-activating peptide may be derived from natural binding partners of p53, including but not limited to p300/CBP, IKK alpha, S100B, p33ING1, 14-3-3 zeta, p28ING4, 14-3-3 sigma, JNK1, JNK 2 JNK3, CDC2, MAPK, E4F1, PCAF, Cables, PKC alpha, ASPP2/53BP2, PKR, HSP90A, STE20 like kinase MST1, HMG1, VRK1, Vimentin, Nucleolin, Rad51, AMF1, RecQ protein like 3, CCAAT-binding factor, RPA, DNA topoisomerase I, BRCA1, DNA topoisomerase II alpha, BRCA2, HSF3, MDC1, Securin, Ref-1, PML, Pin1, RNA polymerase II EF, PTEN, Sin3A, ER alpha, Sp1, Mot-2, TAF9, Nucleostemin, WT1, HIF1 alpha, ZBP89, WOX1, TRAP220, Ribonucleotide reductase, p53BP1, Mdm2, YB-1, MdmX, SMN1, ABL, p63, p'73, ATM, SUMO1, CHK1, CHK 2, NEDD45, CK1 alpha, E2-25K, CDK2, CDK5, CDK7, E2A, DNAPK, UBE3A, ERK1, ERK 2, HAUSP, GSK3 beta or conjugated with peptides capable of penetrating cells (cell penetrating peptide). In some embodiments, the transporter peptides are conjugated with peptides capable of penetrating specific kind of cells, or a combination of a peptide capable of penetrating cell and another peptide capable of recognition of a target cell, e.g., the cells harboring one or more specific surface molecules or receptors.

In one aspect, this invention relates to fusion polypeptides which are first in a class of compounds surprisingly demonstrated herein to inhibit two or more targets from two essential cellular pathways involved in modulating the tumor-suppressive functions, including apoptosis. To the inventors' knowledge, no small molecule compounds have yet been shown to efficiently inhibit two or more targets involved in apoptosis.

In some embodiments, the p53 small molecule agonists of this invention are synthesized, for example, using combinatorial chemistry methods, and screened for binding to two or more targets from two essential cellular pathways involved in modulating apoptosis using high throughput screening.

In some embodiments, the p53-peptide may be derived from p53. In some embodiments, the p53-peptide may bind one or more of the following domains of p53: activation domain 1 (amino acids 1-42), nuclear exclusion domain (amino acids 11-27), Highly Conserved Domain I (amino acids 13-23), activation domain 2 (amino acids 43-92), proline rich domain (amino acids 64-92), DNA binding domain (amino acids 101-300), transcriptional activation domains (amino acids 1-42 or 55-75), MDM2 binding domain, RPA binding domain, p62/TfB1 binding site (a subunit of TFIIH), nuclear localization signaling domain (amino acids 316-325), homo-oligomerisation domain (amino acids 307-355) and the negative regulatory domain (amino acids 356-393). In some embodiments, the p53-activating peptide has the sequence TSFAEYWNLLSP (SEQ ID NO: 7). The amino acid sequence of human p53 is shown below:

Accession number/version number: AAD28535.1 GI:4731632

```
                                                              (SEQ ID NO: 8)
  1  meepqsdpsv epplsqetfs dlwkllpenn vlsplpsqam ddlmlspddi eqwftedpgp 61  deaprmpeaa prvapapaap tpaapapaps wplsssvpsq ktyqgsygfr lgflhsgtak 121  svtctyspal nkmfcqlakt cpvqlwvdst pppgtrvram aiykqsqhmt evvrrcphhe 181  rcsdsdglap pqhlirvegn lrveylddrn tfrhsvvvpy eppevgsdct tihynymcns 241  scmggmnrrp iltiitleds sgnllgrnsf evrvcacpgr drrtekenlr kkgephhelp 301  pgstkralpn ntssspqpkk kpldgeyftl qirgrerfem frelnealel kdaqagkepg 361  gsrahsshlk skkgqstsrh kklmfktegp dsd
```

Zinc-finger protein 363. In some embodiments, the p53-peptide may be derived from peptide library screening platform, including in vitro selection, using techniques but not limited to phage display, ribosomal display, mRNA display, yeast display, against BCL-XL, MCL, MDM2, and MDMX.

The fusion polypeptides of this invention have been shown to be transported into cells, and to surprisingly bind and interact with more than two target proteins involved in mediating apoptosis, including BCL-XL, MCL, MDM2, and MDMX. In some embodiments, the transporter peptides are In some embodiments, the p53-activating peptide may comprise non-naturally occurring amino acids. In some embodiments, the p53-activating peptide may comprise additional amino acids useful for one or more of spacer with another peptide, which can, for example, be useful for improving bioavailability, for example, for altering stability, for altering solubility, for altering hydrophilicity/hydrophobicity, for altering membrane permeability, for altering folding characteristics.

In some embodiments, the fusion polypeptides undergo transport into cells, for example, HSA-mediated transport, and promote the tumor-suppressive functions, including apoptosis by disrupting p53-interaction with one or more of MDM2, MDMX and other proteins that mediate p53 degradation, resulting in accumulation of p53 in the cell. In some aspects of this invention, apoptosis depends on having functional p53 activity in the cell, including renaturation of p53.

In some embodiments, the fusion polypeptides undergo transport into cells, for example, HSA-mediated transport, and, in some aspects of this invention, inhibit the apoptosis inhibitors BCL-XL, MCL, or homologs, orthologs or paralogs thereof, resulting in apoptosis regardless of p53 activity in the cell, e.g., p53-independent apoptosis activity. It has also surprisingly been found that the fusion polypeptides can mediate apoptosis and cytotoxicity in cells independent of the p53 genotype of the cell. Accordingly, in some aspects, the fusion polypeptides of this invention can mediate apoptosis and cytotoxicity in cells that are wild type for p53, as well as p53 mutant cells. p53 mutant cells include p53 negative cells, or cells underexpressing p53 or cells having lower lever or activity of p53. The fusion polypeptides of this invention also disrupt p53-MDM2 and/or p53-MDMX interactions, resulting in accumulation of cellular p53, which can then mediate apoptosis and induce cytotoxicity. In some aspects, cells underexpressing p53 may either express low levels of p53, or express a p53 with lower apoptosis activity than wild-type p53, or both.

Therefore, in some embodiments, the fusion polypeptides of this invention induce cell death in cells including but not limited to (a) a p53-wild-type cell, (b) a p53 mutant cell, (c) a p53-negative cell, wherein the cell is a neoplastic cell, a cancerous cell, or a precancerous cell.

In some embodiments, the cell contacted with the fusion polypeptide, is a cancer cell. In some embodiments, the cell is a p53-wild type cancer cell. In some embodiments, the cell is a p53 mutant. In some embodiments, the p53 mutant cell is a p53-negative cancer cell without detectable p53 activity, or a p53 mutant which expresses low levels of p53, or a p53 with lower BCL, MCL-1, MDM2 and/or lower MDMX binding activity than wild-type p53.

In some embodiments, the present invention relates generally to fusion polypeptides comprising a serum albumin polypeptide and a p53 peptide, and methods of treating, preventing, or ameliorating diseases or disorders, such as cancer or other proliferative disorders. In some embodiments, the fusion polypeptide, used in method of disrupting the Bak-Bcl-XL or BAK-MCL-1 interaction, is a recombinant fusion protein comprising (a) one or more p53-peptides and a serum albumin polypeptide. The fusion polypeptides described herein comprise a polypeptide formed by the fusion of at least one molecule of albumin (or a fragment or variant thereof) to at least one molecule of a p53-peptide. The p53 peptide is a p53 derived peptide or a p53-activating peptide. Preferably the serum albumin polypeptide is a human serum albumin polypeptide, or a serum albumin polypeptide derived from the species of the cells to be contacted or the subject to be treated. Reference to human serum albumin, human serum albumin polypeptide, or rHSA also refers to fragments or variants thereof which maintain its cell transport function and/or its ligand binding activity. Reference sequences for HSA and its mature form are shown below.

1. Human serum albumin preprotein
>gi|145020271|ref|NP_000468.1| serum albumin preproprotein [Homo sapiens]

(SEQ ID NO: 9)

```
MKWVTFISLL FLFSSAYSRG VFRRDAHKSE VAHRFKDLGE
ENFKALVLIA FAQYLQQCPF EDHVKLVNEV TEFAKTCVAD
ESAENCDKSL HTLFGDKLCT VATLRETYGE MADCCAKQEP
ERNECFLQHK DDNPNLPRLV RPEVDVMCTA FHDNEETFLK
KYLYEIARRH PYFYAPELLF FAKRYKAAFT ECCQAADKAA
CLLPKLDELR DEGKASSAKQ RLKCASLQKF GERAFKAWAV
ARLSQRFPKA EFAEVSKLVT DLTKVHTECC HGDLLECADD
RADLAKYICE NQDSISSKLK ECCEKPLLEK SHCIAEVEND
EMPADLPSLA ADFVESKDVC KNYAEAKDVF LGMFLYEYAR
RHPDYSVVLL LRLAKTYETT LEKCCAAADP HECYAKVFDE
FKPLVEEPQN LIKQNCELFE QLGEYKFQNA LLVRYTKKVP
QVSTPTLVEV SRNLGKVGSK CCKHPEAKRM PCAEDYLSVV
LNQLCVLHEK TPVSDRVTKC CTESLVNRRP CFSALEVDET
YVPKEFNAET FTFHADICTL SEKERQIKKQ TALVELVKHK
PKATKEQLKA VMDDFAAFVE KCCKADDKET CFAEEGKKLV
AASQAALGL
```

2. Example of mature human serum albumin (identical to aa 25-609 of the above)
>gi|332356380|gb|AEE60908.1| albumin, partial [Homo sapiens]

(SEQ ID NO: 10)

```
DAHKSEVAHR FKDLGEENFK ALVLIAFAQY LQQCPFEDHV
KLVNEVTEFA KTCVADESAE NCDKSLHTLF GDKLCTVATL
RETYGEMADC CAKQEPERNE CFLQHKDDNP NLPRLVRPEV
DVMCTAFHDN EETFLKKYLY EIARRHPYFY APELLFFAKR
YKAAFTECCQ AADKAACLLP KLDELRDEGK ASSAKQRLKC
ASLQKFGERA FKAWAVARLS QRFPKAEFAE VSKLVTDLTK
VHTECCHGDL LECADDRADL AKYICENQDS ISSKLKECCE
KPLLEKSHCI AEVENDEMRA DLPSLAADFV ESKDVCKNYA
EAKDVFLGMF LYEYARRHPD YSVVLLLRLA KTYETTLEKC
CAAADPHECY AKVFDEFKPL VEEPQNLIKQ NCELFEQLGE
YKFQNALLVR YTKKVPQVST PTLVEVSRNL GKVGSKCCKH
PEAKRMPCAE DYLSVVLNQL CVLHEKTPVS DRVTKCCTES
LVNRRPCFSA LEVDETYVPK EFNAETFTFH ADICTLSEKE
RQIKKQTALV ELVKHKPKAT KEQLKAVMDD FAAFVEKCCK
ADDKETCFAE EGKKLVAASQ AALGL
```

In one aspect, the current invention relates to fusion polypeptides comprising a transporter polypeptide, and a p53 agonist, e.g., a p53 peptide or small molecule agonist, for example, comprising a human serum albumin (HSA) polypeptide and a p53 peptide. In some aspects, the transporter polypeptide may be any natural or artificial polypeptide, including but not limited to, for example, animal serum albumin, polypeptide, including but not limited to a human serum albumin (HSA), or a fragment or variant thereof, animal serum globulin, including but not limited to, an immunoglobulin, (an antibody) or antibody fragment polypeptide, such as an Ig-FC polypeptide, a transferrin polypeptide, an antennapedia peptide, cationic cell penetrating peptide (TAT, having the sequence YGRKKRRQRRR (SEQ ID NO: 11)), SynB1 (RGGRLSYSRRRFSTSTGR (SEQ ID NO: 12)), SynB3 (RRLSYSRRRF (SEQ ID NO: 13)), PTD-4 (PIRRRKKLRRLK (SEQ ID NO: 14)), PTD-5 (RRQRRTSKLMKR (SEQ ID NO:15)), FHV Coat-(35-49) (RRRRNRTRRNRRRVR (SEQ ID NO: 16)), BMV Gag-(7-25) (KMTRAQRRAAARRNRWTAR (SEQ ID NO: 17)), HTLV-II Rex-(4-16) (TRRQRTRRARRNR (SEQ ID NO: 18)), D-Tat (GRKKRRQRRRPPQ) (SEQ ID NO: 19), R9-Tat (GRRRRRRRRRPPQ (SEQ ID NO: 20)), Transportan (GWTLNSAGYLLGKINLKALAALAKKIL (SEQ ID NO: 21)) chimera, MAP (KLALKLALKLALALKLA (SEQ ID NO: 22)), SBP (MGLGLHLLVLAAALQGAWSQPKK-KRKV (SEQ ID NO: 23)), FBP (GALFLGWLGAAGST-MGAWSQPKKKRKV (SEQ ID NO: 24)), MPG (ac-GAL-FLGFLGAAGSTMGAWSQPKKKRKV-cya (SEQ ID NO: 25)), MPG$^{(\Delta NLS)}$ (ac-GALFLGFLGAAGSTMGAWSQPK-SKRKV-cya (SEQ ID NO: 26)), Pep-1 (ac-KETWWETW-WTEWSQPKKKRKV-cya (SEQ ID NO: 27)), Pep-2 (ac-KETWFETWFTEWSQPKKKR KV-cya (SEQ ID NO: 28)), polyarginines (R×N, where 2<N<27 (SEQ ID NO: 29)) chimera, and polylysines K×N (2<N<27 (SEQ ID NO: 30)) chimera. In some embodiments, the transporter peptide is capable of binding to one or more ligands, wherein the ligand may be a fatty acid, an amino acid, a nutrient, a vitamin, a metabolite, a hormone, a drug or a constituent of any bodily fluid. In some embodiments, the transporter peptide is a recombinant peptide. In some embodiments, the transporter peptide is conjugated with a chemical entity, such as a peptide capable of traversing one or more of the placental barrier, the blood-testis barrier, the blood-brain barrier, or any other blood-organ barrier that inhibits entry of the of the transporter in any space within the body.

In some embodiments, the serum albumin polypeptide, for example the HSA polypeptide may also be truncated to modify the C-terminal region of human serum albumin that binds to Fc receptor, in order to increase retention of the fusion polypeptides and increase bioavailability. The fusion proteins described herein are associated with one another, in some embodiments, recombinantly fused (e.g., an albumin open reading frame, encoding a human serum polypeptide comprising, for example, all or a portion of human serum albumin or variant thereof, is fused, in-frame, with a polynucleotide encoding a p53-peptide such as a p53-derived peptide or a p53 activating peptide). In some embodiments, p53-derived peptide or a p53-activating peptide are fused N-terminally to a human serum albumin polypeptide. In some embodiments, p53-derived peptide or a p53-activating peptide are fused C-terminally to human serum albumin. In some embodiments, the p53-peptide may be fused N-terminally and C-terminally to human serum albumin. In some embodiments, the p53-peptide may be inserted or fused in form of tandem repeats of the p53-peptide. In some embodiments, other therapeutic peptide(s) or protein(s) may be fused to human serum albumin p53-peptide fusion protein. In some embodiments, when p53 peptide is not fused to albumin, it can be fused with other peptides including but not limited to IgG Fc fragment, transferrin. In some embodiments, the p53-peptide may be synthesized in tandem repeats and then conjugated to a serum albumin or other suitable protein described herein. In some embodiments, p53-derived peptide or a p53-activating peptide are fused internally to a human serum albumin polypeptide. In some embodiments, multiple copies of p53-derived peptide or a p53-activating peptide are fused to a human serum albumin polypeptide. In some embodiments, only p53-derived peptide is fused with a human serum albumin polypeptide. In some embodiments, only p53-activating peptide is fused with a human serum albumin polypeptide. In some embodiments, p53-derived peptide and p53-activating peptide is fused with a human serum albumin polypeptide. In some embodiments, a suitable linker of one to twenty-five amino acids are inserted at the junction of a human serum albumin polypeptide and p53-derived peptide or p53-activating peptide.

In some embodiments, the genetic fusion is cloned in a vector harboring of the invention may be expressed and purified from a suitable host such as bacteria, yeast, insect cell lines, avian cell lines or mammalian cell lines.

In some embodiments, the fusion polypeptide, used in method of disrupting the Bak-Bcl-XL or BAK-MCL-1 interaction, is a chemically cross-linked fusion polypeptide comprising a p53 peptide or agonist, fused to a human serum albumin polypeptide, for example, (a) a p53-derived peptide and human serum albumin, or (b) a p53-activating peptide and a human serum albumin polypeptide. In some embodiments, cross-linked fusion polypeptide comprising a human serum albumin polypeptide and a p53-derived peptide or p53-activating peptide may be prepared using any suitable method known in the art. In some embodiments, Carbodiimide (e.g., EDC) may be used to chemically crosslink carboxyl groups to amine reactive groups to prepare a cross-linked fusion polypeptide comprising a human serum albumin polypeptide and a p53-derived peptide or p53-activating peptide. In some embodiments, NHS ester, imidoester, pentafluorophenyl ester or hydroxymethyl phosphine may be used to chemically crosslink amine-reactive groups to prepare a cross-linked fusion polypeptide comprising a human serum albumin polypeptide and a p53-derived peptide or p53-activating peptide. In some embodiments, maleimide, haloacetyl (bromo- or iodo-), pyridyldisulfide, thiosulfonate, vinylsulfone may be used to chemically crosslink sulfhydryl-reactive groups to prepare a cross-linked fusion polypeptide comprising HSA or fragment or variant thereof and a p53-derived peptide or p53-activating peptide. In some embodiments, aldehyde-reactive groups like oxidized sugars (carbonyls) may be used to chemically crosslink hydrazide or alkoxyamine to prepare cross-linked a comprising a human serum albumin polypeptide and a p53-derived peptide or p53-activating peptide. In some embodiments, diazirine, aryl azide n may be used to chemically crosslink for random insertion to prepare a cross-linked fusion polypeptide comprising a human serum albumin polypeptide and a p53-derived peptide or p53-activating peptide. In some embodiments, isocyanate may be used to chemically crosslink hydroxyl (nonaqueous)-reactive groups to prepare cross-linked fusion polypeptide comprising a human serum albumin polypeptide and a p53-derived peptide or p53-activating peptide. In some embodiments, the p53 peptide, p53 agonist or fusion polypeptide may be conjugated to other chemicals, including but not limited to polyethylene glycol, which in some embodiments may be conjugated to a human serum albumin. In some embodiments, the p53-peptide or the fusion polypeptide or conjugate described herein may be formulated in a particle formulation, for example, encapsulated in liposomes, nanoparticles or microparticles. In some embodiments, the p53-derived peptide or p53-activating peptide or the fusion protein or conjugate may be bound to a nanoparticle or a microparticles. In some embodiments, the ratio of p53-derived peptide or a p53-activating peptide to a human serum albumin polypeptide may be anywhere in the range of about 100:1 to about 1:10. In some embodiments, only p53-derived peptide is fused with a human serum albumin polypeptide. In some embodiments, only p53-activating peptide is fused with a human serum albumin polypeptide. In some embodiments, p53-derived peptide and p53-activating peptide is fused with a human serum albumin polypeptide. In some embodiments, a suitable linker of one to twentyfive aminoacids are inserted at the junction of a human serum albumin polypeptide and p53-derived peptide or p53-activating peptide.

In some embodiments, the human serum albumin in the fusion polypeptides described herein may be substituted with serum albumin from other vertebrate species, including but to limited to, avian, bovine, canine, cervine, equine, ichthyic, feline, ovine, piscine and porcine albumin. In some embodiments the human serum albumin polypeptide in the fusion polypeptides described herein may be substituted with other proteins including but not limited to antibody polypeptides, such as IgG Fc fragment polypeptides, transferrin polypeptides, an antennapedia peptide, cationic cell penetrating peptide (TAT), transportan and polyarginine In some embodiments, the fusion polypeptide used in method of inhibiting or disrupting the Bcl-XL or MCL-1 inhibition of apoptosis comprises one or more anticancer agents, in addition to the a p53-peptide and a human serum albumin polypeptide. In some embodiments the anticancer agent is chemically conjugated to a natural ligand of human serum albumin. In some embodiments, the additional anticancer agent is covalently bound to the human serum albumin polypeptide. In some embodiments, the additional anticancer drug is a small molecule drug. In some embodiments the additional anticancer agent is bound to the human serum albumin polypeptide through non-covalent interactions. In some embodiments the additional anticancer agent is bound to a fatty acid which is a natural ligand of human serum albumin. In some embodiments, the additional anticancer agent is selected from the group consisting of 2,3,4,5,6-pentafluoro-N-(3-fluoro-4-methoxyphenyl)benzene sulfonamide, abiraterone acetate, afatinib, aldesleukin, alemtuzumab, alitretinoin, altretamine, amifostine, aminoglutethimide, anagrelide, anastrozole, anhydrovinblastine, arsenic trioxide, asparaginase, auristatin, azacitidine, azathioprine, bendamustine, bevacizumab, bexarotine, bicalutamide, bleomycin, BMS 184476, bortezomib, busulfan, cachectin, capecitabine, carboplatin, carmustine, cemadotin, cetuximab, chlorambucil, cisplatin, cladribine, crizotinib, cyclophosphamide, cytarabine, dacarbazine, dactinomycin, dasatinib, daunorubicin, denileukin diftitox, decitabine, 3',4'-didehydro-4'-deoxy-8'-norvin-caleukoblastine, N,N-dimethyl-L-valyl-L-valyl-N-methyl-L-valyl-L-proly-1-L-proline-t-butylamide (SEQ ID NO: 5), docetaxel, dexamethasone, doxifluridine, doxorubicin, epirubicin, epoetin alpha, epothilone, erlotinib, estramustine, etinostat, etoposide, everolimus, exemestane, filgrastim, floxuridine, fludarabine, fluorouracil, fluoxymesterone, flutamide, folate linked alkaloids, gefitinib, gemcitabine, gemtuzumab ozogamicin, GM-CT-01, goserelin, hexamethylmelamine, hydroxyureas, ibritumomab, idarubicin, ifosfamide, imatinib, interferon alpha, interferon beta, irinotecan, ixabepilone, lapatinib, leucovorin, leuprolide, lenalidomide, letrozole, lomustine, mechlorethamine, megestrol, melphalan, mercaptopurine, methotrexate, mitomycin, mitoxantrone, nelarabine, nilotinib, nilutamide, octreotide, ofatumumab, oprelvekin, oxaliplatin, paclitaxel, panitumumab, pemetrexed, pentostatin, polysaccharide galectin inhibitors, procarbazine, raloxifene, retinoic acids, rituximab, romiplostim, sargramostim, sorafenib, streptozocin, sunitinib, tamoxifen, temsirolimus, temozolamide, teniposide, thalidomide, thioguanine, thiotepa, tioguanine, topotecan, toremifene, tositumomab, trametinib, trastuzumab, tretinoin, valrubicin, vegf inhibitors and traps, vinblastine, vincristine, vindesine, vinorelbine, vintafolide, vorinostat, and a combination thereof. Combinations of the fusion polypeptide of this invention with any one or more of the anticancer agents recited above is featured in this invention.

In some embodiments, inhibiting Bcl-XL or MCL-1, leads to death of the cell by apoptosis. In some embodiments, the apoptosis in the cell occurs independent of p53 genotype (wild-type or mutant).

In another aspect the current invention provides a method of inducing cell death in a cell by disrupting or inhibiting BCL-XL, MCL-1 and disrupting p53-MDM2 and/or p53-MDMX interactions, the method comprises (a) providing a fusion polypeptide comprising a a human serum albumin polypeptide and a p53-peptide; and (b) contacting the cell with the fusion polypeptide, thereby inducing cell death. In some embodiments cell death occurs through apoptosis In some embodiments, the cell is a cancer cell selected from the group consisting of (a) a p53-wild-type cancer cell; or (b) a p53 mutant cancer cell, such as a p53-negative cancer cell or a cancer cell expressing low levels of p53 or a p53 having lower BCL-XL, MCL-1 or MDM2/MDMX binding activity than p53.

In some embodiments, the fusion polypeptide used in the method of inducing cell death by disrupting or inhibiting BCL-XL, MCL-1 and disrupting p53-MDM2 and/or p53-MDMX interactions is (a) a recombinant fusion polypeptide comprising a p53-derived peptide and a human serum albumin polypeptide; (b) a recombinant fusion polypeptide comprising a p53-activating peptide and a human serum albumin polypeptide; (c) a chemically cross-linked fusion polypeptide comprising a p53-derived peptide and a human serum albumin polypeptide; or (d) a chemically cross-linked fusion polypeptide comprising a p53-activating peptide and HSA or fragment or variant thereof.

In another aspect, the current invention provides a method of treating a subject with a condition responsive to disrupting or inhibiting BCL-XL, MCL-1 and disrupting p53-MDM2 and/or p53-MDMX interactions, the method comprising (a) administering a therapeutically effective amount of a fusion polypeptide comprising (i) a human serum albumin polypeptide and a p53-derived peptide, or (ii) a human serum albumin polypeptide and a p53-activating peptide. In some embodiments, the subject is a human. In some embodiments, the condition responsive to disrupting or inhibiting BCL-XL, MCL-1 and disrupting p53-MDM2 and/or p53-MDMX interactions, is a cancer. In some embodiments, the fusion polypeptide, used in the methods herein further comprises one or more therapeutic agent, such as an anti-cancer agent.

In some aspects, this invention relates to a pharmaceutical composition comprising a transporter protein and a p53 peptide such as a p53 derived peptide and/or a p53 activating peptide, optionally further comprising a small molecule drug. In some embodiments, the transporter polypeptide may be any natural or artificial polypeptide, including but not limited to, for example, animal serum albumin polypeptide, polypeptide, including but not limited to a human serum albumin (HSA), or a fragment or variant thereof, animal serum globulin, including but not limited to, an immunoglobulin (an antibody) or antibody fragment polypeptide, such as an Ig-FC polypeptide, a transferrin polypeptide, an antennapedia peptide, cationic cell penetrating peptide (TAT), transportan and polyarginine. In some embodiments, this invention relates to a pharmaceutical composition for treating a neoplastic disorder in an animal. In some embodiments, the neoplastic disorder is a cancer. In some embodiments, the animal is a human. In some embodiments, the composition optionally includes one or more of pharmaceutically acceptable excipients, including but not limited to solvents, buffers, binders, disintegrants, fillers, glidants and lubricants. In some embodiments, the pharmaceutical composition is formulated as a capsule, tablet, pellet, dragee, semi-solid, powder, granule, suppositorie, ointment, cream, lotion, inhalant, injection, cataplasm, gel, tape, eye drop, solution, syrup, aerosol, suspension, emulsion, or lyophilisate.

In some embodiments, the compositions of current invention comprise of fusion polypeptides described herein, wherein the fusion peptide is substantially purified. In some embodiments, the substantially fusion peptides of the invention are lyophilized and formulated with a buffer or a preservative.

Pharmaceutical Compositions, Doses, and Administration

In one embodiment the fusion polypeptide comprising a human serum albumin polypeptide and a p53 peptide (for example, a p53-derived peptide or p53-activating peptide) may be formulated in form of pharmaceutical composition for administering to a subject in need thereof. The compositions suitable for use in the method of current invention may be formulated in using one or more physiologically acceptable carriers or excipients. The compositions may be formulated as solutions in appropriate solvents suitable for use in the method of current inventions. In one embodiment the fusion polypeptides comprising a human serum albumin polypeptide and p53-derived peptide or p53-activating peptide may be formulated in form of an aqueous solution prepared using a carrier such as physiologically acceptable osmogen or buffer solution as including but not limited to saline, phosphate buffered saline and water. In one embodiment the non-saline osmogen may advantageously be an amino acid selected from a group comprising histidine, valine, proline and cysteine. The osmogen may also be: a polyalchohol phosphoric ester such as glycerophosphate, a polyol such as mannitol, sorbitol, glycerol or xylitol, a monosaccharide such as glucose, galactose, xylose, fructose, galactosamine, glucosamine, neuraminic acid, and glucuronic acid; or a disaccharide such as sucrose, maltose and lactose. In one embodiment the fusion polypeptides comprising a human serum albumin polypeptide and p53-derived peptide or p53-activating peptide may be formulated as a non-aqueous solvent solution for pharmacologic use. In some embodiments, the non-aqueous solvent solution can be prepared by dissolving the fusion polypeptide in a solvent comprising DMSO, or lipid carrier.

The formulations of this invention comprising the fusion polypeptide comprising a human serum albumin polypeptide and p53-derived peptide or p53-activating peptide may also comprise excipients and/or carriers selected from solubilizers, stabilizers, buffers, tonicity modifiers, bulking agents, viscosity enhancers/reducers, surfactants, chelating agents, and adjuvants.

The pharmaceutical compositions of this invention may comprise the fusion polypeptides present at a concentration in the range of about 0.000001 to about 10% (weight/volume), for example, from about 0.000001 to about 0.0001%, from about 0.0001% to about 0.01%, from about 0.01% to about 0.1%, from about 0.1% to about 1%, from about 1% to about 10% (weight/volume).

In one embodiment, the fusion polypeptide comprising a human serum albumin polypeptide and p53-derived peptide or p53-activating peptide may be formulated for parenteral delivery by a route such as intravenous, subcutaneous, intramuscular, and intra-articular administration. These formulations are either liquids or lyophilizates. In one embodiment, the formulation comprising the fusion polypeptide is prepared as a concentrate, which is diluted with a suitable carrier before administration. In one embodiment, the formulation comprising the fusion polypeptide is prepared as a lyophilised powder, which is diluted with a suitable carrier before administration. The liquid or lyophilized formulations may comprise from 1-50% of the fusion polypeptides comprising a human serum albumin polypeptide and p53-derived peptide or p53-activating peptide. The lyophilized formulations of this invention may also comprise excipients and/or carriers selected from solubilizers, stabilizers, buffers, tonicity modifiers, bulking agents, viscosity enhancers/reducers, surfactants, chelating agents, and adjuvants. Lyophilized formulations need to be reconstituted prior to administration. These ingredients are well known to one of ordinary skill in the art. Liquid formulations are optionally diluted with pharmaceutically acceptable diluents such as 5% Dextrose Injection, USP or 0.9% Sodium Chloride Injection, USP. These formulations are administered by infusion or bolus administration.

In one embodiment, the formulations of this invention comprising the fusion polypeptide comprising a human serum albumin polypeptide and a p53-peptide, such as a p53 derived peptide or p53-activating peptide can also be formulated for oral delivery as a solution, gelatin capsule, or tablet. The oral liquid formulations and capsule formulations are well known to one of ordinary skill in the art. The tablet formulation can include: 1-80% the fusion polypeptides comprising a human serum albumin polypeptide and a p53-derived peptide or p53-activating peptide; 10-90% binders, disintegrants, fillers, glidants, lubricants; and 1-20% additional compounds that ensure easy disintegration, disaggregation, and dissolution of the tablet in the stomach or the intestine.

The tablet may be formulated for immediate release, sustained release, or delayed or modified release. The tablet may be optionally coated can make the tablet resistant to the stomach acids and it disintegrates in the duodenum, jejunum and colon as a result of enzyme action or alkaline pH. These formulations are well known to one of ordinary skill in the art. The tablets may be further coated with sugar, varnish, or wax to mask the taste.

In certain embodiments, pharmaceutical compositions comprising formulation comprising the fusion polypeptides comprising a human serum albumin polypeptide and a p53-derived peptide or p53-activating peptide may be formulated for administration by other routes of administration, including but not limited to systemic peripheral, or topical administration. Illustrative routes of administration include, but are not limited to, oral, transdermal, transmucosal, intranasal, ocular, pulmonary, rectal, vaginal, parenteral, such as by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and by implant of a depot or reservoir, such as intramuscularly. Dosage of the pharmaceutical compositions may vary by route of administration. Certain administration methods may include the step of administering the composition one or more times a day to obtain the desired therapeutic effect.

In one embodiment, the formulation may comprise the fusion polypeptides comprising a human serum albumin polypeptide and p53-derived peptide or p53-activating peptide is prepared as an aerosol balm, cream, emulsion, foam, gel, liniment, lotion, ointment, suspension or spray.

In one embodiment, the fusion polypeptides comprising a human serum albumin polypeptide and a p53-derived peptide or p53-activating peptide are formulated as a topical composition, which may include pharmaceutically acceptable excipients. Exemplary excipients may be solvents (e.g. water, alcohol, propylene glycol, ethylene glycol, glycerol), hydrocarbon bases (e.g., hard paraffin, soft paraffin, microcrystalline wax and ceresine), absorption bases (e.g., wool fat, beeswax), water soluble bases (e.g., macrogols 200, 300, 400), emulsifying bases (e.g., emulsifying wax, cetrimide), emu oil, vegetable oils (e.g., olive oil, coconut oil, sesame oil, almond oil and peanut oil), polymers (e.g. dextran, polyacrylic acid, carbomer, polyethylene oxide, polyethylene glycol, a copolymer of ethylene oxide and propylene oxide, polyvinylpyrrolidone, arabinogalactan), cellulose (e.g. hydroxypropylmethyl cellulose, carboxypropylmethyl cellulose, methylcellulose, hydroxymethyl cellulose, hydroxyethyl cellulose, hydroxypropylmethyl cellulose), gums (e.g., guar or xanthan gum), salts, acids, bases etc., or penetrant (e.g., dimethyl sulfoxide, dimethyl acetamide, dimethylformamide and n-decyl-methyl sulfoxide propylene glycol, glycerin, lanolins, alcohols, anionic emulsifiers (e.g. sodium lauryl sulfate) and surfactants (nonionic emulsifiers such as polyoxyethylene fatty alcohol ethers and esters; polyoxyethylene fatty acid esters, e.g. polyoxyethylene stearate; polyoxyethylene sorbitan fatty acid esters and sorbitan fatty acid esters, e.g. sorbitan monostearate; polyoxyethylene glycol fatty acid esters; polyol fatty acid esters, e.g. glyceryl monostearate; and ethoxylated lanolin derivatives).

Methods of the Invention

In one aspect, the current invention provides method of treating a subject with a condition responsive to inhibiting or disrupting BCL-XL and MCL-1 mediated inhibition of apoptosis, and disrupting p53-MDM2 and/or p53-MDMX interaction, comprising administering a composition comprising a fusion polypeptide of this invention. The methods include administering, to a patient, a composition (e.g., a pharmaceutical composition) comprising a fusion polypeptide comprising a human serum albumin polypeptide and a p53-peptide, such as a p53-derived peptide or p53-activating peptide. Administration by one or more of the following routes: oral, epidural, intraarticular, intracardiac, intracavernous, intradermal, intramuscular, intraosseous, intraperitoneal, intrathecal, intravenous, intravitreal, nasal inhalation, oral, subcutaneous, topical, and is contemplated.

The invention also features the use of fusion polypeptides comprising a human serum albumin polypeptide and a p53-derived peptide or p53-activating peptide in the preparation of a medicament for use in any of the methods described herein. Also included are the uses of fusion polypeptides comprising a human serum albumin polypeptide and a p53-derived peptide or p53-activating peptide in the preparation of a medicament for the treatment of a condition responsive to inhibiting or disrupting BCL-XL and MCL-1 mediated inhibition of apoptosis, and disrupting p53-MDM2 and/or p53-MDMX interaction. Also included are the uses of fusion polypeptides comprising a human serum albumin polypeptide and a p53-derived peptide or p53-activating peptide in the preparation of a medicament for the treatment of cancer.

Use of proteins and peptides as therapeutic agents has investigated in recent years, with the average number of new peptide drug candidates growing from an average of 1.2 per year in the 1970's to 16.8 per year so far in the 2000's [1]. These biologically active molecules have advantages over small molecule drugs, including higher specificity and decreased potential to cause adverse effects. Among these promising candidates, however, few are known to bind intracellular proteins, thus ignoring potentially clinically relevant intracellular targets. An efficient cell penetrating technology remains one of the major obstacles to peptide drug administration. In some embodiments, this invention features a delivery technology using a human serum albumin polypeptide, for example, recombinant human serum albumin (rHSA), to promote cellular penetration of a therapeutic peptide, optionally together with a small molecule drug. In addition to prolonging serum stability, this novel strategy is capable of facilitating simultaneous intracellular delivery of two therapeutic agents, each with distinct but complimentary mechanisms, to promote a synergistic therapeutic response for the treatment of a variety of diseases. One model used to test this delivery technology employed a p53-derived peptide to target the anti-apoptotic interaction between two intracellular proteins, p53 and MDM2. The p53 tumor suppressor protein plays a critical role in generating cellular responses to a number of stress signals, including DNA damage, aberrant proliferative signals due to oncogene activation, and hypoxia. Upon activation, p53 is stabilized and moves to the nucleus, where it binds to DNA in a sequence specific manner and promotes transcriptional regulation of genes involved in DNA repair, cell-cycle arrest, senescence, and apoptosis [2,3]. Previous studies demonstrated that p53-mediated apoptosis plays a critical role to suppress tumor formation in mice [4].

While it is estimated that the p53 gene is mutated in 50% of tumors, increasing evidence reveals that a large percentage of tumors retain wild type p53, but possess other alterations in the p53 pathway, which prevents its critical tumor-suppressive function [5]. One key component altering p53 activity is the E3 ubiquitin ligase, MDM2. This negative regulator directly binds to p53 and promotes the ubiquitination and subsequent proteasomal degradation of p53. Under normal conditions, MDM2 functions as a harness for p53 activity, regulating its subcellular location, transcriptional activity, and stability. In tumors, however, MDM2 is frequently upregulated, thus preventing the p53 stress response even in cases where wild type p53 is present. As a result, patients often display accelerated tumor growth and a diminished response to treatment [6,7]. Disruption of the p53-MDM2 interaction has become a popular strategy to increase functional p53 levels and thus, reduce cancer cell viability.

The binding interface of p53-MDM2 is composed of a hydrophobic cleft on the N-terminal surface of MDM2 and the N-terminal transactivation domain of p53. Since the revealing of the interaction interface, a series of small molecules and peptides have been developed to target the p53-binding pocket of MDM2 [8]. One such class of small molecule antagonists termed nutlins, have demonstrated the ability to dock within the p53-binding pocket of MDM2, resulting in p53 accumulation, initiation of cell cycle arrest, and ultimately, apoptosis [9, 10]. Despite this, translation into an effective treatment modality has shown little promise. The limited effect of small molecule p53-MDM2 inhibitors is thought to be in part due to the lack of inhibition of MDMX, a homolog of MDM2 [11, 12]. In depth analyses of MDM2 and MDMX revealed both proteins work in concert to decimate the p53 pathway, thus necessitating the development of an inhibitor with dual specificity [13]. Rationally designed synthetic peptides offered an alternative to nutlins and other small molecule antagonists by binding and inhibiting both MDM2 and MDMX. PMI peptide was developed by Li and colleagues to compete with p53 for MDM2 and MDMX binding at an affinity approximately 2 orders of magnitude higher than that of a wild type p53-derived peptide (containing amino acids 17-28 of the p53 protein) [14, 15]. As recognized herein, although this work provided support for targeting the p53-MDM2/MDMX interaction as a cancer therapy, problems surrounding proteolytic stability and intracellular peptide delivery still remained.

Interest in using HSA as a drug carrier has grown in recent years due to a number of properties including: preferential uptake in tumor and inflamed tissue, stability, biodegradability, ready availability, and lack of toxicity and immunogenicity [16-18]. HSA is capable of improving the pharmacokinetic profile of peptide- or protein-based drugs by chemical conjugation, genetic fusion, and micro/nano particle encapsulation [19]. HSA is the most abundant plasma protein with an average half-life of 19 days. It functions as a natural transport vehicle for metal ions, a number of drugs, and long chain fatty acids in the blood [20]. In addition, tumor cells often have an increased rate of albumin uptake. For example, HSA makes up 19% of the soluble proteins within certain breast cancer cells [21]. A number of drugs have been designed to exploit these valuable characteristics of HSA. Acylated insulin and glucagon-like peptide-1, which rely on HSA-mediated binding to extend serum stability, have been approved for clinical use [22, 23]. The HSA/paclitaxel nanoparticle known as Abraxane was approved for the treatment of metastatic breast cancer and has shown promise as a delivery strategy to extend the half-life and therapeutic efficacy of small molecule drugs [19]. A major concern of albumin-based formulations such as Abraxane, however, is the uncertainty surrounding their aptitude for generating an immune response against endogenous HSA. Based on extensive in vivo studies and several clinical trials, no such immune response has been reported, even for HSA fused to immunostimulating cytokines, such as interferon α2b (Albuferon) [24]. Furthermore, Recombumin, a genetically engineered form of HSA used to replace endogenous albumin, is already in therapeutic use and has a proven lack of toxicity and immunogenicity [17].

The cell penetration technology described herein utilizes the long-chain fatty acid transport properties of HSA with the methods herein for genetically modifying HSA to deliver a highly specific peptide to an intracellular target. Acylation with long chain FA is a method that has previously been used to extend the serum half-life of small compounds by facilitating nonspecific association with serum albumin and lipoproteins [25]. In contrast to the acylated drugs currently approved for clinical uses that rely on random serum protein association in vivo, our HSA-mediated delivery technology is pre-formulated under optimized in vitro conditions to guarantee simultaneous intracellular delivery of two complimentary therapeutic agents. This strategy allows drug transport and release to mimic the robust fatty acid uptake as well as albumin transport.

Combination therapy is one approach for cancer treatment. Delivery of multiple therapeutics, simultaneously to one target, can improve efficacy and minimize toxicity. Encapsulated micro/nano particles and conjugated polymers have been developed to co-deliver different therapeutics. However, as discussed herein, those methods are plagued by a number of factors including immunogenicity, difficulty in penetrating solid tumors, lack of selectivity for target tumor tissue, inefficient dissociation from a covalently-bound carrier, and reliance on passive diffusion, a process that does not guarantee co-delivery of both anticancer agents to the same cell [26, 27]. The data described herein suggests HSA is a feasible choice to serve as a protein carrier for co-delivery of C-terminal fused p-53 peptides and FA-modified molecules. In the realm of cancer treatment, it is our hope that such a system can ultimately be used to facilitate intracellular delivery of two anticancer agents, each with distinct roles in regard to triggering or responding to cellular DNA damage, to promote a more robust apoptotic response for the treatment of solid tumors.

As discussed herein, the results demonstrate the feasibility of using genetically modified HSA to fuse a therapeutic p53-peptide, while retaining FA-binding ability for use as a carrier to co-deliver both a p53-peptide and FA-modified Drug (FA-Drug). Two exemplary fusion polypeptides, e.g., HSA proteins containing either a wild type p53-derived peptide (P53i) (SEQ ID NO:1) or the high affinity MDM2-binding peptide N8A-PMI (PMI) (SEQ ID NO:2) were cloned, expressed in Pichia pastoris yeast system, and purified [28]. Cellular and biochemical studies indicate that rHSA-P53i and rHSA-PMI were efficiently taken up by osteosarcoma SJSA-1 cells and retained MDM2- and MDMX-binding activity. In addition, both rHSA-P53i and rHSA-PMI promoted cytotoxicity in SJSA-1 cells via caspase activation. As the future application of this rHSA delivery technology aims to deliver one or more FA-Drugs in addition to a C-terminal-fused therapeutic peptide, FA-binding and stability studies were also performed using FA-FITC. As hypothesized by the inventors, exemplary fusion polypeptides (e.g., rHSA proteins (rHSA-P53i and rHSA-PMI)) were able to form highly stable complexes with FA-FITC via non-covalent interactions. In addition, FA-FITC complexed with HSA could be internalized by the target cells and rHSA fusion proteins still retained cytotoxicity.

EXAMPLES

Example 1: Methods for Design and Expression of Exemplary Fusion Polypeptides, rHSA-p53 and rHSA-PMI Recombinant HSA fusion proteins were cloned into pPICZαA vector (Invitrogen). The 5' primer contained a 21 base pair sequence overlapping with the N-terminal of HSA cDNA and the XhoI cloning site of the vector (5'-ATCGCTCGAGAAAAGAGAGGCTAAGCGACGCACA-CAAGAGTGAGGTTGCT-3' (SEQ ID NO: 31)). The 3' primer contained a portion of the C-terminal of HSA, wild type P53i (ETFSDLWKLLPE (SEQ ID NO: 1)) or PMI (TSFAEYWALLSP (SEQ ID NO: 2)) peptides, as well as the NheI restriction site. This sequence was subsequently amplified by PCR. Each peptide sequence was fused to the C-terminal of HSA by overlapping PCR with primers:

(HSA C-terminal)
(SEQ ID NO: 32)
5'-CCATAGGTCTGAAAACGTTTCACCTCAACTTCGTCGGCGCCTAA
GGCAGCTTGACTTGCAGC-3', -continued (rHSA-P53i, C-terminal)
(SEQ ID NO: 33)
5'-CGATGCTAGCACTAGTTTATTCAGGAAGTAGTTTCCATAGGTCT
GAAAACGTTTCACC-3', (rHSA-PMI, C-terminal)
(SEQ ID NO: 34)
5'-CGATGCTAGCCCGCGGTTATGGACTAAGAAGAGCCCAGTACTCA
GCAAAACTTGTACCGTCAACTTCGTCGGCGCC-3'.

The pPICZαA vector was digested with XhoI and XbaI to create the 5' and 3' cloning sites. The HSA fusion protein sequences were digested with XhoI and NheI and ligated into the linearized vector. Following ligation and transformation, the cloned genes were confirmed by DNA sequencing. Pichia pastoris yeast cells (Invitrogen, 18258-012) were then transformed using linearized pMM1 (for HSA-P53i) or pMM2 (for rHSA-PMI) plasmid DNA and rHSA-P53i and rHSA-PMI clones were selected for Zeocin resistance after 72 hours. Recombinant proteins were then expressed in Pichia pastoris according to the manufacturer's instructions (Invitrogen, K1740-01).

Purification of rHSA-P53i and rHSA-PMI

Culture media containing albumins secreted from P. pastoris were filtered (0.2 μm) and subsequently incubated for 4 hours at 4° C. with cibacron blue dye agarose (Sigma, C9534) [29]. Following 10× volume washes with ice-cold PBS, recombinant proteins were eluted stepwise using PBS containing sodium thiocyanate (NaSCN) (100 mM, 200 mM, 500 mM, 750 mM and 1 M). Fractions containing rHSA-P53i or rHSA-PMI (500 mM to 750 mM NaSCN) were pooled and dialyzed in PBS. Purified proteins were analyzed by SDS-PAGE with purity greater than 95%. Recombinant HSA proteins were then filtered (0.2 μm) for sterilization and stored at −20° C. Protein concentration was determined using the Bradford method (Bio-Rad, 23225).

FITC and Biotin-Labeling of rHSA

FITC and biotin-labeling of rHSA (biotin-rHSA) were performed using NHS-Fluorescein (Thermo Scientific, 46409) and NHS-Biotin (Thermo Scientific, 20217) according to the manufacturer's instructions. Both labeling procedures were performed using 20 times excess of NHS. Following the incubation, proteins were dialyzed in 1×PBS to remove unconjugated NHS reagents.

Cell Culture and Cytotoxicity Studies

Osteosarcoma SJSA-1 cells (ATCC) were grown in RPMI media containing 10% FBS. Cytotoxicity assays were performed using SJSA-1 cells plated in 24- or 96-well plates at 20,000 or 5,000 cells per well, respectively. Cells were allowed to attach overnight. All treatments were added on day 2 in RPMI media containing 1% FBS plus the equivalent amounts of 1×PBS buffer. Unless otherwise indicated, cells were exposed to treatment media for 24 hours, at which time cytotoxicity was measured using the fluorometric CyQuant assay (Invitrogen, C35006) or the fluorometric Homogeneous Caspase assay (Roche, 03005372001), according to the manufacturer's instructions, for detection of apoptosis. All results were plotted relative to rHSA- or where indicated, rHSA/FA-FITC-treated cells.

Confocal Microscopy

On day 1, SJSA-1 cells were seeded in 6-well plates, at a density of 80,000 cells per well, and allowed to attach overnight. Treatment media containing 1% FBS plus 5 μM FITC-labeled rHSA (FITC-rHSA), FITC-rHSA-P53i or FITC-rHSA-PMI was added to wells on day 2 and allowed to incubate for 24 hours. For experiments to examine the internalization activity of FA-FITC-modified rHSA, SJSA-1 cells were plated as described above. On day 2, rHSA fusion proteins (dissolved in 1×PBS) were incubated with FA-FITC at a 1:2 molar ratio (rHSA:FA-FITC; 5 μM:10 μM) to allow formation of rHSA/FA-FITC complexes. Reactions were conducted in PBS at room temperature for 30 minutes, prior to dilution in RPMI media (without FBS) and addition to wells. Following a 24 hour incubation period, cells were trypsinized, re-plated onto coverslips and allowed to re-attach for 2 hours. Upon re-attachment, cells were washed 3× with PBS and maintained in phenol red-free media. For visualization, imaging was performed using a Nikon TiE (Eclipse) confocal microscope with a CSU-X spinning disk confocal scan head (Yokogawa), a linear encoded x, y robotic stage (ASI Technologies, Inc.), equipped with a multi-bandpass dichromatic mirror and bandpass filters (Chroma Technology Corp.) in an electronic filter wheel for selection of FITC. 488 nm laser illumination was provided by a 50 mW monolithic laser combiner (MLC400, Agilent Technologies) and images were acquired using a 60×1.40 NA objective and the Clara interline CCD camera (Andor Technology).

Co-Immunoprecipitation and Protein Detection by Western Blotting

SJSA-1 cells were lysed in buffer containing 20 mM Tris-HCl, 50 mM NaCl, 0.05% Triton X-100, and protease inhibitor cocktail. For each condition, 200 μg SJSA-1 cell extract was heated to 42° C. prior to the addition of 4 μg biotinylated rHSA-P53i, rHSA-PMI or rHSA protein. Mixtures were then allowed to incubate for 1 hour at RT. Next, MDM2 (Santa Cruz, sc-965) or MDMX antibody (Santa Cruz, sc-74467) was added to each tube and allowed to incubate, while rotating, for 4 hours at 4° C. Proteins bound to MDM2/MDMX antibody were pulled down using Protein A/G (1:1) resins and samples were analyzed by SDS-PAGE and Western blotting using MDM2, MDMX, and Streptavidin-HRP antibodies (Pierce, 21130). Primary and secondary antibodies were added in 2% non-fat dry milk in TBST at the following dilution ratios: p53 (Santa Cruz, sc-126), MDM2, MDMX (1:200), streptavidin-HRP (1:2500), and GAPDH (1:5000) (Santa Cruz, sc-59541). Proteins were visualized by the chemiluminescent detection solution, SuperSignal West Dura Extended Duration Substrate (Thermoscientific, 34075) and densitometry was performed on replicate experiments using Image J software (NIH).

Gel Shift Assays to Determine Stability of FA/HSA Complexes

All recombinant albumins were defatted following a previous publication [30]. FA-FITC was synthesized by mixing 1× 1-Hexadecylamine and 2× N,N-Diisopropylethylamine (Sigma) followed by addition of 1×NHS-Fluorescein (Thermo Scientific). This reaction was carried out overnight, protected from light. Products were then purified by HPLC and identified by MS. For experiments designed to detect FA/HSA complex formation, rHSA (30 pmol, dissolved in 1×PBS) was incubated with or without FA-FITC at desired molar ratios and then separated by 0.5×TBS PAGE. Due to the incorporation of fluorescent molecules, HSA bound by FA-FITC in gel can be visualized under UV. Assays to determine the degree of displacement of FA-FITC were performed by adding an excess amount of unlabeled FA to pre-formed rHSA/FA-FITC complexes, at the indicated molar ratios. Reactions were conducted in PBS containing 10% glycerol at room temperature for 30 minutes. The products were separated using non-denaturing 0.5×TBS PAGE and then visualized under 305 nm UV. Experiments to determine the effect of the presence of serum on HSA/FA complexes were conducted using pre-formed biotin-rHSA/FA-FITC complexes. After initial complex formation, the biotin-rHSA/FA-FITC solution was divided equally among 4 tubes. Ten percent FBS or the same volume of PBS was subsequently added to respective samples and the mixtures were allowed to incubate for up to 24 hours at 37° C. followed by the addition of streptavidin-conjugated resins to pull-down biotinylated rHSA/FA-FITC complexes (GenScript, L00353). Streptavidin resins were pre-equilibrated with HSA to minimize nonspecific interactions. Samples performed in parallel to assess total FA-FITC incorporation did not receive streptavidin resins, but underwent an identical incubation time of either 1 or 24 hours at 37° C. Next, samples were centrifuged to pull down biotin-HSA/FA-FITC and a portion of each supernatant was analyzed using 0.5×TBS PAGE as above.

Example 2: HSA Fusion Protein Design, Expression, and Purification

The structural basis for MDM2/MDMX interaction with p53 is discussed below. To form a complex with MDM2 or MDMX, the amphipathic α-helix fragment of the N-terminal transactivation domain of p53 must bind within the concave binding pocket of MDM2/MDMX. Despite minor sequence differences and a slightly smaller hydrophobic binding cleft in MDMX compared to MDM2, structural studies reveal that the p53 binding domains of both proteins display a high degree of similarity. The minimally required MDM2/MDMX binding sequence includes residues 19-26 of the transactivation domain of wild type p53 (F19S20D21L22W23K24L25L26 (SEQ ID NO: 3)). Three critical residues, known as the hydrophobic triad (F19W23L26), bind to the three distinct sites of the MDM2/MDMX hydrophobic pocket [8, 31, 32].

In this study, two peptide sequences were chosen as exemplary sequences to test the initial HSA-mediated peptide delivery approach. The first construct fused to HSA contains the wild type p53 binding sequence (E17T18F19S20D21L22W23K24L25L26P27E28 (SEQ ID NO: 1)) and the second sequence is a potent MDM2/MDMX peptide inhibitor, PMI (TSFAEYWNLLSP (SEQ ID NO: 7)), adopted from the work of Li and colleagues [14, 15]. To avoid the effect of bulky HSA structure on peptide-MDM2/1MDMX interaction, a caspase cleavage site (DEVDG (SEQ ID NO: 6)) was inserted as a linker between HSA and peptide (FIG. 1A). The insertion of this linker may facilitate liberation of peptides from HSA following p53 accumulation and subsequent caspase activation.

Figure 1B:
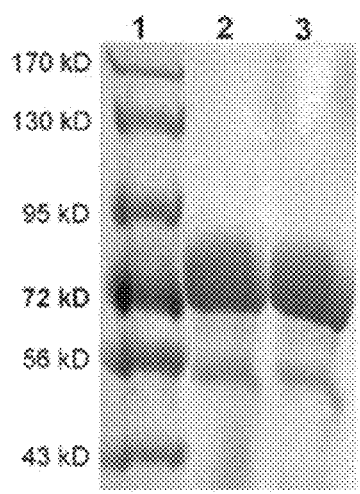

The wild type p53-derived peptide (P53i) or PMI peptide sequences were fused to the C-terminal of HSA (FIG. 1A) using a protocol as described in Methods. The fusion proteins were then cloned into pPICZαA Pichia pastoris protein expression vectors and transformed into yeast cells. Recombinant HSA-P53i and rHSA-PMI were overexpressed and purified using cibacron blue dye agarose to achieve >95% purity confirmed by SDS-PAGE (FIG. 1B).

Example 3: Both rHSA-P53i and rHSA-PMI are Efficiently Internalized by SJSA-1 Cells Therapeutic activity hinges upon successful delivery of a peptide or small molecule drug into the cell. While new strategies are consistently being evaluated to deliver functional proteins or peptides into cells, they are still lacking in overall efficiency and safety for translation into a clinical model [1]. Current HSA drug formulations such as Abraxane, the HSA-paclitaxel nanoparticle, demonstrate efficient intracellular HSA uptake. Multiple modes of internalization have been shown to play a role, including receptor-mediated as well as endocytic pathways [19].

While the exact mechanism underlying the uptake of rHSA-P53i and rHSA-PMI is not fully known, the results provided herein confirm that exemplary fusion polypeptides, such as rHSA fusion proteins, are in fact taken up by cells, a critical step to target intracellular proteins. To do this, confocal microscopy was employed to visualize the extent of internalization of FITC-labeled rHSA fusion proteins by SJSA-1 cells. Cells were treated with 5 μM FITC-rHSA, FITC-rHSA-P53i or FITC-rHSA-PMI in the presence of 1% FBS for 24 hours. Depicted in FIG. 2A-C, all three proteins (rHSA, rHSA-P53i, and rHSA-PMI) were taken up into SJSA-1 cells. In comparison to rHSA, treatment with rHSA-P53i and rHSA-PMI resulted in robust intracellular vesicle formation and distribution.

Example 4: Exemplary Fusion Polypeptides, rHSA-P53i and rHSA-PMI, Bind Both MDM2 and MDMX Exemplary fusion polypeptides, rHSA-P53i and rHSA-PMI, were designed to elicit inhibitory activity against MDM2 and its homolog, MDMX [8, 9, 10, 32], in order to disrupt p53-MDM2, and result in accumulation of p53 and restoration of its tumor-suppressive function. To confirm both exemplary fusion polypeptides possess MDM2/MDMX binding ability, SJSA-1 whole cell lysate was incubated in the presence of biotin-rHSA, biotin-rHSA-P53i or biotin-rHSA-PMI. Proteins were then pulled down using anti-MDM2 or anti-MDMX antibodies and followed by Western blotting using streptavidin-HRP to detect biotinylated rHSA bound to MDM2/MDMX. Reciprocal detection was performed using streptavidin resins to pull down biotinylated rHSA protein followed by Western blotting using anti-MDM2 or anti-MDMX antibodies (data not shown). As depicted in FIG. 3, both rHSA-P53i and rHSA-PMI co-immunoprecipitated with MDM2 and MDMX, thus confirming that target protein binding ability was retained following peptide fusion to HSA, and transport into the cell.

Figure 4A:
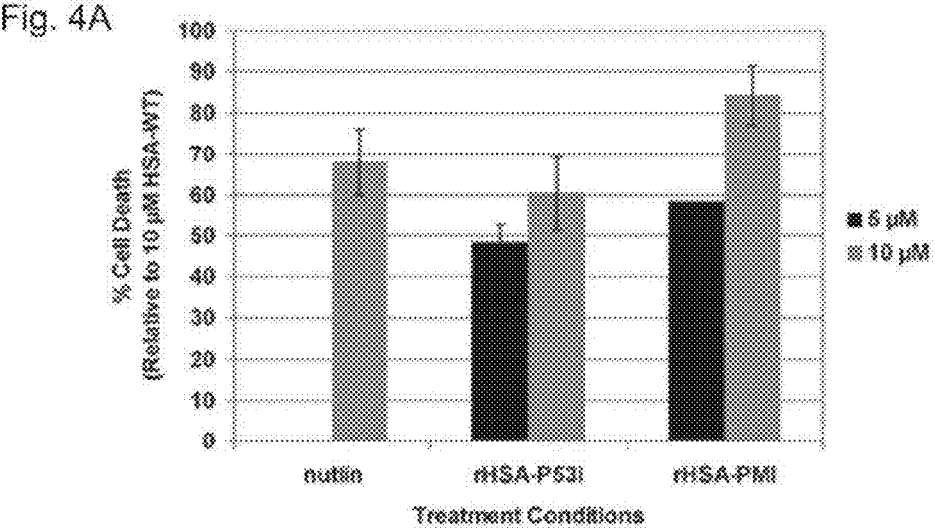
FIG. 4A and FIG. 4B show that rHSA-P53i and rHSA-PMI promote cytotoxicity in SJSA-1 cells via caspase activation. rHSA fusion proteins, as well as nutlin (to serve as a p53-MDM2 antagonist control) were added at the indicated concentrations and allowed to incubate for 24 hrs.

Example 5: Exemplary Fusion Polypeptides, rHSA-P53i and rHSA-PMI, Promote Cytotoxicity Via Caspase Activation Adequate levels of p53 are necessary to mediate the cytotoxic effects from chemotherapy or radiation treatment and restoration of its activity has been found to promote tumor regression in mice [4, 33]. A small molecule p53-MDM2 antagonists, nutlins, has previously been used to show that competition with endogenous p53 at the hydrophobic binding cavity of MDM2, can result in accumulation of p53 and initiation of apoptosis [9, 10]. To determine if exemplary polypeptides, such as the rHSA fusion proteins, are able to trigger apoptosis via p53 activation, the MDM2-overexpressing cell line, SJSA-1, was incubated with rHSA-P53i, rHSA-PMI or nutlin. Following a 24-hour treatment, cytotoxicity was assessed using the CyQuant Assay. Both rHSA-P53i and rHSA-PMI promoted cytotoxic responses in SJSA-1 cells (approximately 60% and 84% cell death, respectively) (FIG. 4A).

p53 functions as a tumor suppressor by promoting the expression of pro-apoptotic proteins capable of triggering apoptosis via caspase activation. To determine if the cytotoxic response observed was indeed occurring as a result of an apoptotic mechanism, SJSA-1 cells were treated as described above and analyzed for caspase activation. Results in FIG. 4B reveal an approximate 7-fold increase in caspase activation in rHSA-PMI-treated cells and up to 2-fold increase in all other treatments. These data confirm that both exemplary fusion polypeptides, rHSA-P53i and rHSA-PMI, promoted cytotoxicity in SJSA-1 cells and this response was driven by apoptotic mechanisms.

Example 6: Exemplary Fusion Polypeptides, rHSA-P53i and rHSA-PMI, Promote p53 Accumulation p53 functions as a transcription factor for genes involved in mediating key cellular processes such as, DNA repair, cell-cycle arrest, senescence, and apoptosis. In addition, p53 upregulates MDM2 protein expression, via an autoregulatory feedback loop [34-36]. The results in FIG. 3 illustrate that rHSA-P53i and rHSA-PMI are capable of disrupting native p53-MDM2 interaction. To extend these studies, the effect of exemplary fusion polypeptides, such as the rHSA fusion proteins, on p53 and MDM2 protein expression was determined. In FIG. 5A, Western blotting was performed to detect both MDM2 and p53 protein levels in SJSA-1 cells after incubation with rHSA-P53i, rHSA-PMI, nutlin, or media alone for 24 hours. As expected, both rHSA-P53i and rHSA-PMI promoted a mild increase in p53, 1.5- and 2.9-fold increases, respectively. Nutlin-treatment promoted robust p53 accumulation (11.5-fold average increase). However, while nutlin displayed a 5-fold average increase in MDM2 protein expression relative to untreated cells; the exemplary fusion polypeptides, rHSA-P53i and rHSA-PMI, did not promote any significant effects on MDM2, resulting in only 1.1- and 1.0-fold changes in protein levels, respectively. Thus, it was surprisingly found that maintenance of lower MDM2 levels following administration of exemplary fusion polypeptides, such as rHSA fusion protein treatment, may confer an advantage over nutlin, as upregulation of MDM2 may counterbalance increases in p53 protein and thus, compromise therapeutic efficacy [37].

Example 7: Fatty Acid (FA)-Modified FITC Forms a Stable Complex with Exemplary Fusion Polypeptides, rHSA-P53i and rHSA-PMI FA modification has previously been used to prolong the half-life of small compounds by facilitating non-specific association with serum albumin and lipoproteins [25]. Here, the potential of using rHSA fusion proteins to deliver a FA-Drug was examined. Unlike acylated drugs currently in use [22, 23], the inventors used an in vitro formulation strategy, whereby a FA-Drug is incorporated into rHSA prior to administration. This method ensures uniform and reproducible complex formation, and guarantees each rHSA protein administered will co-deliver both FA-Drugs and a therapeutic peptide.

Figure 6A:
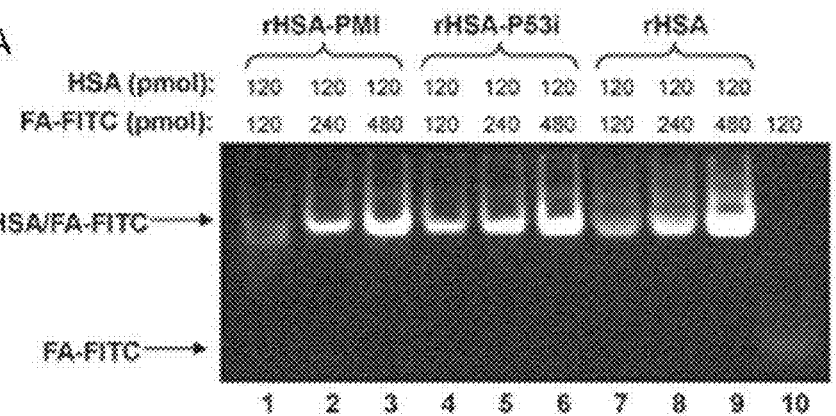
FIG. 6A and FIG. 6B show that rHSA fusion proteins are able to form stable complexes with FA-FITC.
Figure 6B:
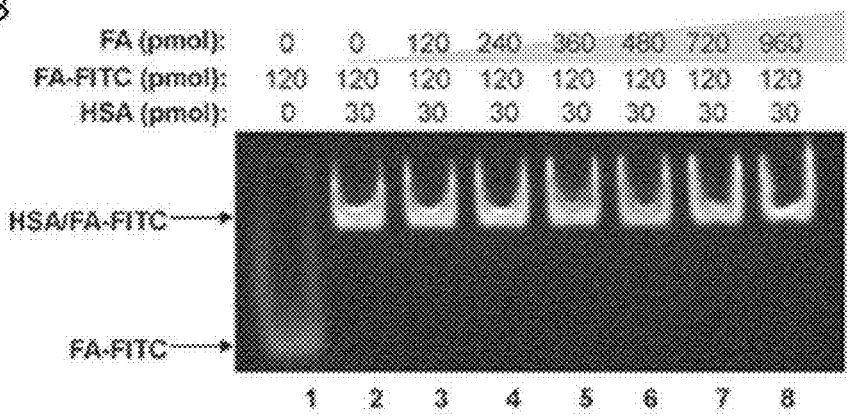
Figure 6C:
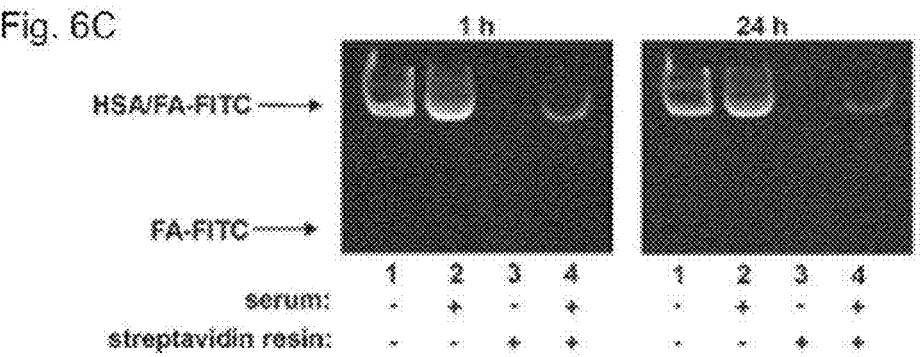
FIG. 6C). Preformed biotin-rHSA and FA-FITC complexes (biotin-rHSA:FA-FITC; 1:2) were incubated with PBS (Lane 1 and 3) and 10% serum (lane 2 and 4) for 1 and 24 hours. Lanes 1 and 2 represent total FA-FITC incorporation into rHSA without and with 10% FBS, respectively, prior to the addition of streptavidin resins. Lane 3 (with PBS only) and lane 4 (with 10% FBS) correspond to the supernatants of samples after incubation with streptavidin resins and pulling down rHSA/FA-FITC complexes. The absence of rHSA/FA-FITC complexes in lane 3 indicates that all biotin-rHSA/FA-FITC complexes (in PBS) were efficiently pulled down. Any FA-FITC present in lane 4 would imply the displacement of rHSA-bound FA-FITC by serum components. The presence of only a weak band in lane 4 indicates the majority of FA-FITC remained bound to rHSA (pulled down by streptavidin resins). Quantitation of the amount of FA-FITC in lane 4 (Image J, NIH) revealed approximately 15% and 17% of FA-FITC was removed from biotin-rHSA in the presence of serum following 1 and 24 hour incubations, respectively.

In this study, the extent of incorporation and stability of pre-loaded FA using FA-FITC was examined. Recombinant HSA/FA-FITC complex formation was detected using a gel shift assay as described in Methods. Complete incorporation of FA-FITC was achieved up to a 1:4 ratio of rHSA:FA-FITC. Notably, the degree of FA binding was similar among rHSA, rHSA-P53i, and rHSA-PMI (FIG. 6A). This implies rHSA fusion proteins folded properly and the C-terminal peptide fusion did not alter FA binding ability. As native albumin and free FA will be present under physiological conditions, we designed experiments to mimic an in vivo setting in order to assess the overall stability of rHSA/FA complexes. These FA competition assays included: 1) determination of the extent of exchange of HSA-bound FA with excess free FA and 2) assessment as to whether or not incubation in the presence of serum would displace FA from pre-formed rHSA/FA complexes. Our data indicate that rHSA/FA-FITC complexes (formed at 1:4 molar ratio; rHSA:FA-FITC) were stable in the presence of unlabeled FA, up to a 1:8 molar ratio (rHSA-associated FA-FITC: unlabeled FA) (FIG. 6B). Next, we examined the extent of exchange of rHSA-bound FA-FITC with lipoproteins and albumin present in serum. To do this, pre-formed biotinylated rHSA/FA-FITC complexes were divided into four separate reaction mixtures. Each reaction condition corresponds to the lane assignments (lanes 1-4), as depicted in FIG. 6C. Samples 2 and 4 received 10% serum, while samples 1 and 3 received the same volume of PBS. Each mixture was then allowed to incubate for up to 24 hours at 37° C. To determine the degree of dissociation of FA-FITC from pre-formed rHSA/FA-FITC complexes into serum proteins, streptavidin-conjugated resins were added to samples 3 and 4. This allowed biotin-rHSA/FA-FITC to be pulled down and the supernatants were analyzed for the presence of FA-FITC by gel shift assay. The same aliquots were taken from samples 1 and 2 to serve as positive controls for the determination of total HSA-bound FA-FITC present in each sample prior to the addition of streptavidin-conjugated resins. Any appearance of FA-FITC in lanes 3 and 4 represented the amount of FA-FITC that dissociated from pre-formed rHSA/FA-FITC complexes. A comparison between lane 1 (total rHSA-bound FA-FITC) and lane 4 (serum-associated FA-FITC) indicates the degree of FA-FITC displacement from rHSA into serum proteins. Approximately 86% of FA-FITC remained bound to rHSA following a 24-hour incubation, demonstrating only minimal exchange of FA-FITC occurred between pre-formed rHSA/FA-FITC and albumin or lipoproteins in serum.

Example 8: FA-FITC and Exemplary Fusion Polypeptide Complexes (Such as rHSA Fusion Protein Complexes) were Able to Transport FA-FITC and Promote Cytotoxicity Acylated drugs currently approved for clinical use rely on HSA to enhance solubility and mediate transport to locations within the vicinity of target tissue. Studies have shown that while no gross structural disorganization occurs upon FA incorporation into HSA, FAs have been observed to stabilize the protein against denaturation during clinical applications, indicating some subtle structural changes may occur [38]. It has been demonstrated that FA-FITC and HSA form a stable complex. However, it is uncertain whether the complex interferes with the cellular uptake of FA-FITC or the cytotoxic activity of rHSA fusion proteins.

Figure 7A:
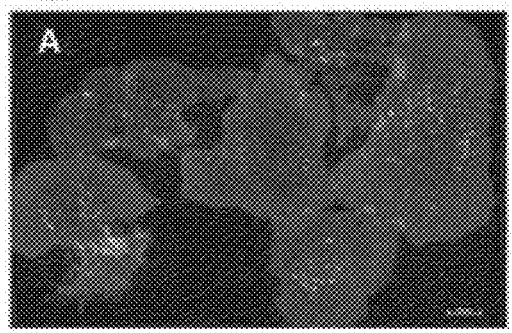
FIG. 7A, FIG. 7B and FIG. 7C show that rHSA/FA-FITC complexes retain internalization and cytotoxic activity.
Figure 7B:
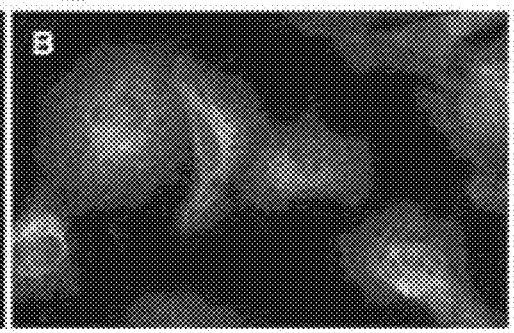
Figure 7C:
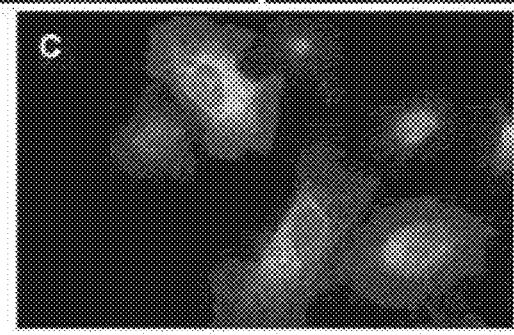

Confocal microscopy was employed to examine internalization of rHSA/FA-FITC complexes as described in Methods. Prior to imaging, SJSA-1 cells were incubated with FITC-labeled rHSA, pre-formed rHSA/FA-FITC complexes, or FA-FITC alone (FIG. 7A-C, respectively). As illustrated in FIG. 6, we have determined that rHSA/FA-FITC complexes are highly stable even in the presence of 10% serum. The results in FIG. 7 demonstrate uptake of FA-FITC, pre-formulated with rHSA (FIG. 7B), is similar to that of FA-FITC directly added to the culture medium (FIG. 7C). The diffuse FITC staining in FIG. 7B indicates HSA/FA-FITC complexes do not interfere with uptake of FA-FITC or affect intracellular distribution of FA-FITC. To assess the effect of FA-FITC on rHSA fusion proteins, rHSA/FA-FITC, rHSA-P53i/FA-FITC, and rHSA-PMI/FA- FITC complexes were formed at a molar ratio of 1:2 (rHSA:FA-FITC; 5 µM:10 µM). These complexes, as well as a positive control containing nutlin plus rHSA/FA-FITC, were added to SJSA-1 cells and allowed to incubate for 24 hours. The results in FIG. 7D reveal the cytotoxic effects of both of the exemplary fusion polypeptides, rHSA-P53i and rHSA-PMI, complexed with FA-FITC. The cytotoxicity associated with rHSA-P53i/FA-FITC and rHSA-PMI/FA-FITC was comparable to that of 5 µM rHSA-P53i and rHSA-PMI (FIG. 4A).

Example 9: Discussion

Figure 8A:
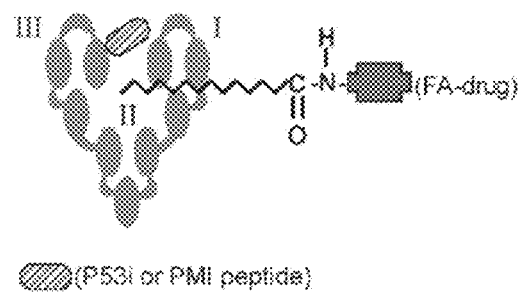
FIG. 8A and FIG. 8B show a schematic diagram of rHSA-mediated codelivery technology. Recombinant HSA-delivery complexes were conceived as a co-delivery technology in that 1) therapeutic peptides can be fused to the C-terminal of HSA for both extracellular (FIG. 8A) and intracellular (FIG. 8B) targeting and 2) FA-Drugs can form stable complexes with rHSA fusion proteins to promote synergistic therapeutic efficacy.
Figure 8B:
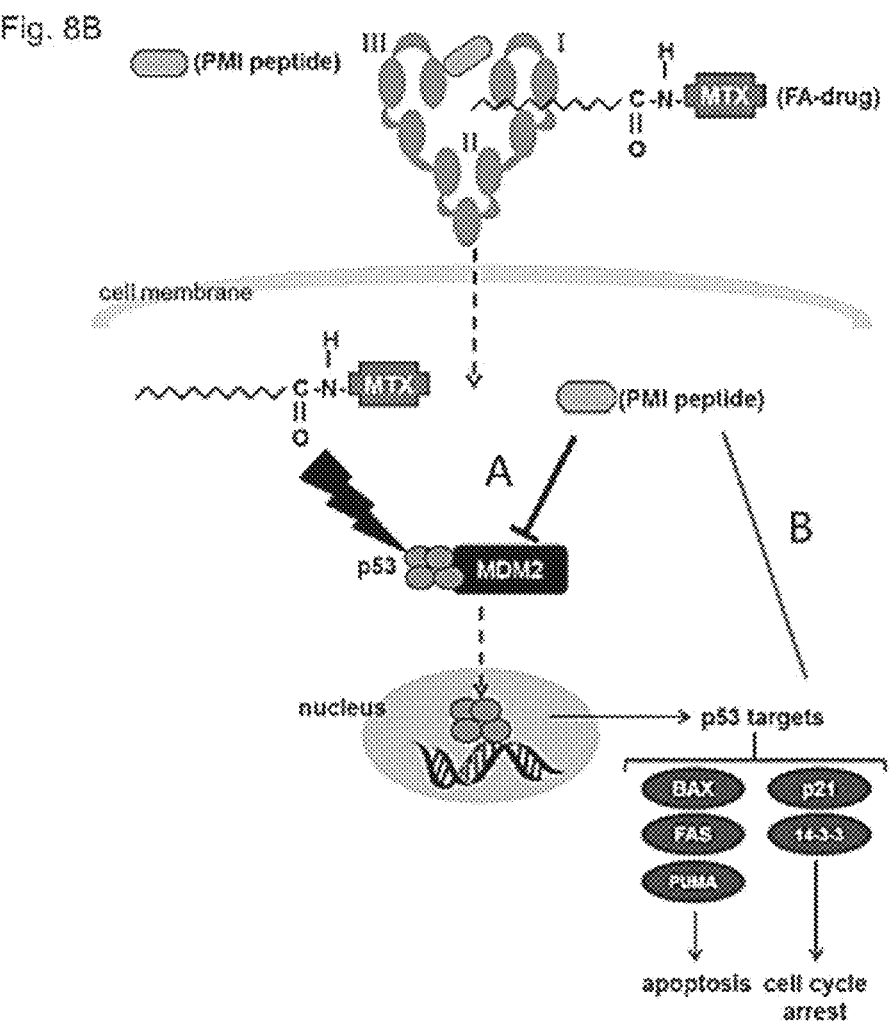

The advent of small peptide therapeutic agents has resulted in the ability to enhance target specificity and blunt toxicity compared to small molecule drugs. Despite these advantages, serum instability and rapid renal clearance have plagued their widespread usage. This example demonstrates the feasibility of using a therapeutic fusion polypeptide as an efficient peptide delivery method to target intracellular proteins, circumvent proteolytic degradation in vivo, and translate into enhanced serum stability and improved therapeutic efficacy. In addition, this delivery technology has been designed to exploit the intrinsic fatty acid transport properties of HSA to allow it to co-deliver both a FA-Drug and an intracellular-targeting p53 peptide (such as a p53 derived peptide or a p53 activating peptide, e.g. P53i or PMI) to elicit a synergistic therapeutic response (FIG. 8).

HSA possesses three homologous domains. Based on physicochemical studies, HSA is a highly flexible protein that is capable of changing its molecular shape under different conditions. The flexibility is partially due to the relative motions of its domain structures. In particular, the two alpha helices in the C-terminal of domain III have minimal interaction with other parts of the protein [16]. The C-terminal is thus the logical location for sequence fusion of therapeutic peptides. The data presented here, using a p53 reactivation model, support our hypothesis that rHSA can be genetically engineered to deliver a therapeutic peptide to an intracellular target and serve as a carrier for FA-modified small molecule drugs. Wild type p53 (P53i) and PMI peptides were fused into HSA by genetic cloning, expressed in a Pichia pastoris yeast system, and purified (FIG. 1). Intracellular uptake of rHSA-P53i and rHSA-PMI by MDM2-overexpressing SJSA-1 cells was confirmed by confocal microscopy (FIG. 2A-C). Furthermore, co-immunoprecipitation assays revealed rHSA fusion proteins were capable of occupying the hydrophobic binding pocket of both MDM2 and MDMX, thus preventing native p53 degradation (FIG. 3). These actions resulted in the accumulation of p53 and subsequently, apoptosis (FIGS. 4 and 5). Lastly, rHSA fusion proteins retained stable FA-binding ability, a critical factor for their eventual application as a carrier for FA-Drugs (FIG. 6A). Once forming a complex, rHSA and FA-modified molecules remained stable even in the presence of excess competing free FA (FIG. 6B), as well as serum (FIG. 6C).

Improving serum half-life and retaining target protein binding ability is only one of the hurdles that must be overcome for a carrier to successfully deliver functional peptides to a cancer cell. In addition, a drug complex must reach the tumor microenvironment and intracellular uptake must occur to allow for target protein interaction and subsequent therapeutic effect. An important feature of HSA is its ability to cross vascular endothelial cells through albumin-mediated transcytosis and accumulate in the interstitial space of tumor tissues, a process known as the enhanced permeability and retention (EPR) effect [39]. Intracellular uptake of HSA also occurs under conditions of cellular stress, where it serves as a vital source of amino acids. For instance, it has been reported that tumor cells often have an increased rate of HSA uptake [21]. While the precise mode of cellular entry is not entirely clear, studies performed to examine the cellular uptake of Abraxane have revealed that transcytosis is initiated upon binding of HSA to a cell surface glycoprotein (gp60) receptor (albondin), as well as binding of HSA to SPARC (secreted protein acid and rich in cysteine) [40]. Apart from receptor-mediated uptake, fluid phase endocytosis is also suggested to play a role [18]. While future studies will be needed to determine the precise mechanism of rHSA-P53i and rHSA-PMI intracellular uptake, the studies presented here were designed to confirm that rHSA fusion proteins can be efficiently taken up by cancer cells.

To examine cellular uptake, rHSA, rHSA-P53i and rHSA-PMI were fluorescently labeled with FITC. Studies were also performed using FA-FITC and rHSA complexes to examine whether or not this formulation interferes with FA-FITC internalization or rHSA fusion protein activity. Following 24-hour incubation with SJSA-1 cells, confocal microscopy was performed to determine the extent of rHSA fusion protein and rHSA/FA-FITC uptake. Abundant FITC-staining within intracellular vesicles, as depicted in FIG. 2, indicates FITC-labeled rHSA-P53i, rHSA-PMI, and rHSA were readily taken up into cells. Interestingly, the degree of internalization was most efficient in cells exposed to rHSA-P53i and rHSA-PMI. FIG. 7B confirms FA-FITC, of rHSA/FA-FITC complexes, are also effectively delivered intracellularly based on the extensive FITC staining pattern, which is similar to that of FA-FITC treatment alone.

Although the neonatal Fc receptor (FcRn) may contribute to albumin internalization, the exact mechanism underlying the increased uptake of rHSA fusion proteins relative to rHSA has yet to be determined. FcRn is a major histocompatibility class I (MHCI) molecule involved in the recycling of both IgG and HSA. It prevents intracellular degradation of protein and prolongs its serum half-life. Importantly, IgG and HSA proteins that do not bind FcRn are retained within the cell and eventually processed into lysosomes for proteolytic degradation. Work performed by Andersen et al. demonstrated that an intact domain III, which contains the C-terminal of HSA, is crucial for FcRn binding and subsequent exporting back to the cell surface [41]. Future studies will be necessary to determine if the C-terminal modification of HSA interferes with FcRn binding, thus promoting intracellular retention of rHSA fusion proteins.

Figure 4B:
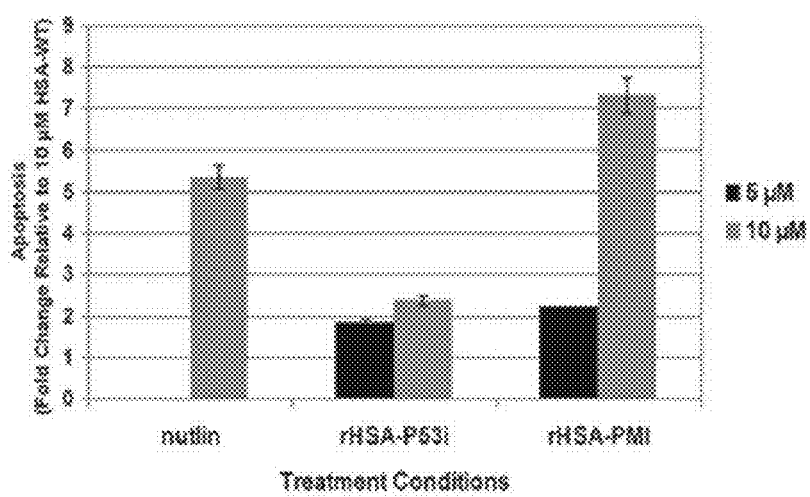
Figure 7D:
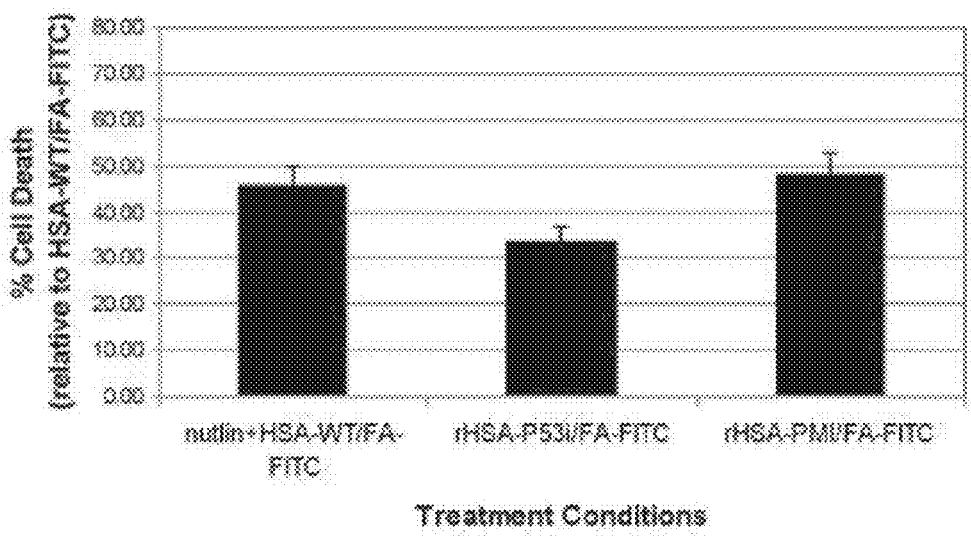
FIG. 7D). rHSA/FA-FITC or rHSA/FA-FITC fusion protein complexes were added at a 1:2 molar ratio (rHSA:FA-FITC; 5 µM:10 µM) to SJSA-1 cells and allowed to incubate for 24 hrs. Nutlin (5 µM) was added in the presence of rHSA/FA-FITC to serve as a positive control. Cytotoxicities were measured by CyQuant Assay as described in Methods. Results are displayed as percent cell death relative to 5 µM rHSA/FA-FITC-treated wells. Data are representative of an experiment performed in triplicate. Error bars indicate ±SD.

The overall goal of this technology is to efficiently deliver a therapeutic peptide and potentially, for co-delivery of FA-Drugs to induce a synergistic response. Thus, we next designed experiments to examine the cytotoxic effect of rHSA-P53i and rHSA-PMI. Our data reveal rHSA-P53i and rHSA-PMI, as well as rHSA-P53i/FA-FITC and rHSA-PMI/FA-FITC complexes, caused significant cytotoxicity in SJSA-1 cells (FIGS. 4A and 7D, respectively). In addition, robust caspase activation was triggered following rHSA fusion protein treatment. This implies toxicity was related to apoptotic mechanisms (FIG. 4B).

To further elucidate the mechanisms underlying the cytotoxic effects of rHSA-P53i and rHSA-PMI, Western blots were performed to examine changes in p53 and MDM2. It has been reported that disruption of p53-MDM2 binding can prevent the sequestration and subsequent ubiquitination of p53 by MDM2 and result in accumulation and reactivation of p53. In line with this mechanism, we observed an increase in p53 protein following a 24-hour incubation with rHSA- P53i, rHSA-PMI or nutlin. Unlike nutlin, treatment with rHSA-P53i or rHSA-PMI did not cause an increase in MDM2.

The consequences of p53 activation are highly complex and can be different depending on a number of factors, such as differences in stimuli, external environment or cellular milieu. p53-dependent cellular outcomes are dictated by a myriad of transcriptional targets. It has been shown that p53 transcription stimulates the synthesis of MDM2. However, MDM2 can inhibit the transcriptional activity of p53 by binding to its transactivation domain. Furthermore, MDM2 can regulate the degradation of p53 by acting as a shuttle to transport p53 out of the nucleus into the cytosol. Thus, p53 and MDM2 form an autoregulatory feedback loop [34-36]. The dynamic regulatory pathway of MDM2 makes it hard to predict the protein expression outcome caused by p53 activation. In a closed system, it could be assumed that p53 accumulation would lead to an increase in MDM2 protein expression. However, in a cellular context, one must consider that a number of other factors can affect MDM2 stability and activity. As depicted in FIG. 5, an increase in p53 protein expression following treatment with rHSA-P53i and rHSA-PMI was observed, while MDM2 remained at basal levels. These results are in contrast to previous studies of MDM2 small molecule antagonists, which observed a concomitant increase in MDM2 upon p53 accumulation [10]. This inconsistency poses an important question: what levels of MDM2 inhibition and p53 activity are required to invoke a beneficial therapeutic effect? To answer this question, work performed by Mendrysa et al. using mouse models with a hypomorphic allele of MDM2, found that even small reductions in MDM2 levels were sufficient to cause a mild p53 response [42]. Based on these studies, our data may suggest p53 activation was beneath the threshold required for promoting p53-mediated transcription of MDM2. A second scenario may also exist in which liberated p53, at different concentrations, triggers transcription of a different subset of genes involved in p53-mediated apoptosis that does not include MDM2. Lastly, we have considered a transcription-independent apoptotic mechanism mediated by cytoplasmic p53 [43]. It was shown that p53-dependent apoptosis still occurred in the presence of transcriptional or translational inhibitors. Furthermore, p53 mutants lacking transcriptional activity retained the ability to trigger apoptotic function. It is possible rHSA-P53i and rHSA-PMI interfere with the transportation of cytoplasmic p53 into the nucleus. Clearly, further studies will be needed to determine whether or not a transcriptional-independent or -dependent apoptotic pathway underlies rHSA fusion protein cytotoxicity, as well as the exact mechanisms underlying the maintenance of MDM2 levels following rHSA fusion protein treatment.

We further explored the potential of using rHSA-P53i or rHSA-PMI as a vehicle to co-deliver a FA-Drug as well as a therapeutic peptide. For ease of quantitation and detection, FITC was chosen as the model molecule to test the feasibility and stability of this co-delivery technology. Recombinant HSA-mediated delivery of FA-Drugs offers a number of advantages over traditional drug delivery methods. These include: 1) HSA association improves solubility of FA-Drugs as well as extremely hydrophobic drugs, 2) formation of FA-Drug and rHSA complex occurs naturally upon incubation and does not require an elaborate chemical reaction, 3) the non-covalent nature of FA-Drug and rHSA negates the need for protein degradation as in polymer/protein-drug conjugates, and 4) drug absorption could also be enhanced due to increased hydrophobicity of the fusion polypeptides and HSA-mediated uptake. Generally, LCFAs dissociate from HSA, translocate across the cell membrane, and then reach the mitochondrial membrane and other intracellular locations. The translocation of LCFA across the cell membrane may go through two co-existing mechanisms: simple diffusion and saturable receptor-mediated processes. If a FA-Drug follows the route of LCFA, it may reach the cytoplasmic target through 1) FA transporter-mediated translocation or 2) passive diffusion facilitated by the FA lipophilic alkyl chain. If HSA is involved in the transportation, FA-Drug may translocate across the cell membrane through 1) HSA binding protein-mediated endocytosis or 2) increased HSA uptake in tumor cells [21, 40]. Thus, multiple uptake pathways may lead to more efficient drug absorption.

As formulation of rHSA/FA-Drug will be performed in vitro, assessing the stability of this complex under simulated in vivo conditions was necessary to determine whether significant displacement of FA-Drug from rHSA complexes will occur in the presence of free fatty acids or serum. The work presented here reveals minimal exchange of FA-FITC took place even in the presence of 8 times excess of free FA (FIG. 6B). In addition, pre-formulated biotin-rHSA/FA-FITC complexes remained stable for up to 24 hours in the presence of 10% serum, a condition designed to mimic an in vivo setting (FIG. 6C).

In recent years, many studies have confirmed that blocking p53-MDM2 interaction holds promise in reestablishing the p53 tumor suppressor pathway when wild type p53 is present. This is particularly relevant in terms of treatment, given that certain cancer cells overexpress MDM2 or MDMX, an MDM2 homolog that also binds and sequesters p53. Structural studies of the p53-binding groove within MDM2 led to the development of both small molecule peptide mimetics (such as nutlins) and rationally designed peptide inhibitors. While nutlins have allowed the mechanistic proof-of-concept for disrupting p53-MDM2 binding for cancer therapy, their pharmacological properties have prevented translation into a clinical model. Peptide inhibitors have the advantage of offering a high degree of target specificity, as well as the ability in some cases to bind and inhibit both MDM2 and MDMX. Despite this potency, however, peptide inhibitors have demonstrated only modest effects in invitro cell models, presumably due to poor membrane permeability and structural stability. Here we present a method that may not only overcome the current obstacles associated with peptide drug delivery into cells, but also facilitates the co-transport of small molecule anti-cancer agents. Although fatty acid modification may enhance the cellular uptake of molecules, future studies may be needed to optimize the FA conjugation linker to promote maximum internalization and cytotoxic activity of small molecule drug candidates.

Example 10

The compositions of this invention are useful for enhancing cellular response to apoptosis, for use in cancer therapy, such as cancer combination therapy. p53 protein is a critical cancer suppressor that senses intrinsic cellular stresses and controls apoptosis. MDM2 is overexpressed in many cancer cells, and binds to p53, promoting the degradation of p53. Disruption of p53 and MDM2 interaction by peptides and small molecules can to stimulate the accumulation of cellular p53 and activate p53-mediated apoptosis, and subsequently sensitize cellular response to chemotherapeutics. There are two major biological functions of wild type p53, transcription-dependent and independent cellular regulations. In addition to the transcription functions of cellular p53, p53 can directly bind and inhibit two anti-apoptotic proteins, BCL-XL and MCL and induce apoptosis. No studies have shown that p53 can induce apoptosis in p53 mutant cancer cells such as p53 negative cells or cells underexpressing p53 (including cells expressing p53 with lower apoptotic mediating activity than wild-type p53. It has been demonstrated herein that p53-derived peptides (that do not include active p53) can surprisingly bind and interact with four targets, MDM2, MDMX, BCL-XL, and MCL and induce cytotoxicity independent on p53 genotype (wild type, or mutant, including p53 negative or p53 underexpressing cells). This finding expands the application of p53-derived peptides and analogues to most cancer cells, even p53 negative or p53 underexpressing cells. Previously, no small molecules targeting apoptosis mechanism have been shown can inhibit more than two targets involved in mediating apoptosis efficiently.

Example 11: Exemplary Fusion Polypeptide Binding to BCL-XL and MCL-1 (for Example, rHSA-P53i and rHSA-PMI)

As shown herein, rHSA-P53i and rHSA-PMI induce apoptosis in SJSA-1 cells (p53 positive cancer cell line). This is explained by the fact that p53 functions as a tumor suppressor by promoting the expression of pro-apoptotic proteins capable of triggering apoptosis via caspase activation. However, it has also been surprisingly found, that exemplary fusion polypeptides, rHSA-P53i and rHSA-PMI, induce apoptosis in other cell lines, including MDA-MB-231 (a p53 negative cancer cell line), or Hela (a p53 under-expressing cancer cell line).

Figure 9A:
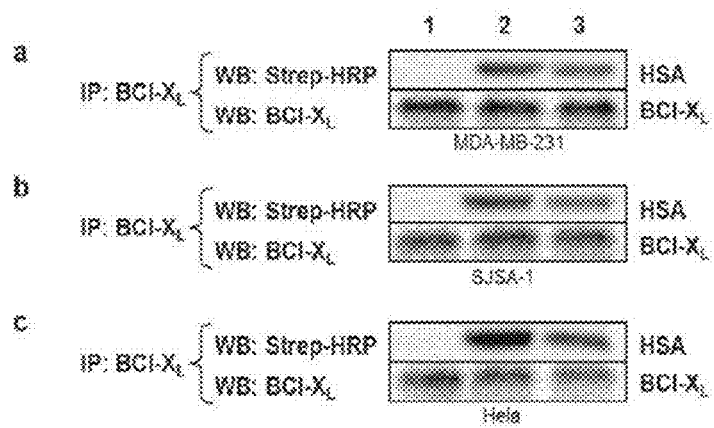
FIG. 9A shows that that rHSA-P53i and rHSA-PMI bind to Bcl-xL and Mcl-1. To detect the interaction between Bcl-xL/Mcl-1 and rHSA fusion proteins, 4 µg each of biotin-rHSA (lane 1), biotin-rHSA-P53i (lane 2), or biotin-rHSA-PMI (lane 3) were added to 200 µg of MDA-MB-231 (a) SJSA-1 (b) or Hela (c) whole cell lysates. Bcl-xL (FIG. 9A) or Mcl-1 (FIG. 9B) antibody was added to the lysate followed by pulling down Bcl-xL/Mcl-1 and rHSA complexes using Protein A/G (1:1) resins. Samples were then analyzed by SDS-PAGE and Western blotting using Bcl-xL, Mcl-1, and Streptavidin-HRP (Strep-HRP) antibodies. Biotin-labeled HSA and HSA-p53i were pulled down by streptavidin-conjugated agaroses (FIG. 9C). Proteins associated with HSA-p53i were blotted by BCL-XL and MCL-1 antibodies.
Figure 9B:
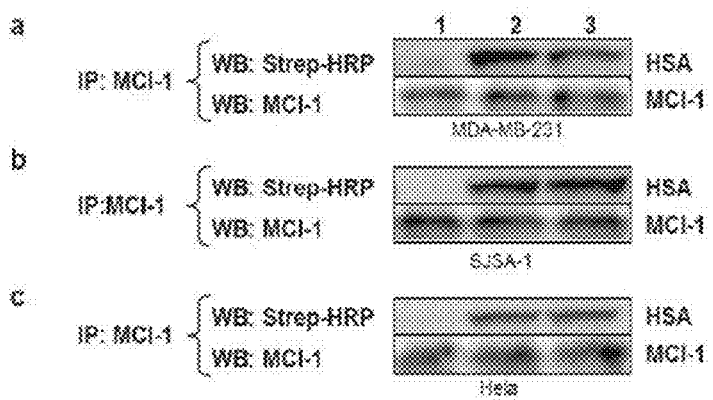
Figure 9C:
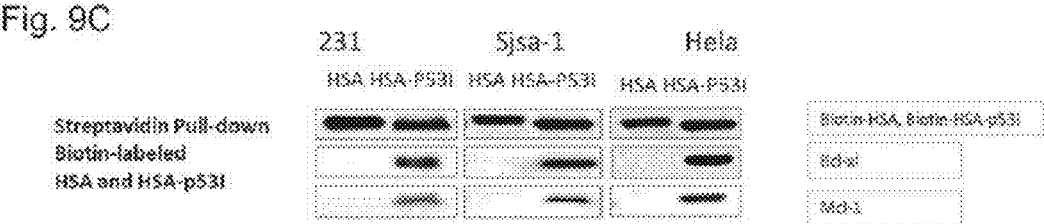

To elucidate the molecular basis for the above surprising observation, the inventors explored whether proteins like Bcl-xL/Mcl-1 interact with rHSA-P53i and rHSA-PMI. We added biotin-rHSA, biotin-rHSA-P53i, or biotin-rHSA-PMI to MDA-MB-231 (p53 negative cancer cell line), SJSA-1 (p53 positive cancer cell line) or Hela (p53 under-expressing cancer cell line) whole cell lysates. Proteins were then pulled down using anti-Bcl-xL antibody, anti-Mcl-1 antibody or streptavidin and followed by Western blotting using streptavidin-HRP (to detect biotinylated rHSA), anti-Bcl-xL or anti-Mcl-1 antibodies. The results are shown in FIG. 9. As depicted in FIG. 9A, anti-Bcl-xL antibody pulled down biotin-rHSA-P53i (lane 2) and biotin-rHSA-PMI (lane 3) but not biotin-rHSA (lane 1), from MDA-MB-231 (a), SJSA-1 (b) or Hela (c) whole cell lysates. Similarly, as shown in FIG. 9B, anti-Mcl-1 antibody pulled down biotin-rHSA-P53i (lane 2) and biotin-rHSA-PMI (lane 3) but not biotin-rHSA (lane 1), from MDA-MB-231 (a), SJSA-1 (b) or Hela (c) whole cell lysates. As illustrated in FIG. 9C, streptavidin pulled down Bcl-xL and Mcl-1, when biotin-rHSA-P53i or biotin-rHSA-PMI (lane 2) but not when HSA (lane 1) was added. Again these protein were pulled down from MDA-MB-231, SJSA-1 as well as Hela whole cell lysates. These data demonstrate that the exemplary fusion polypeptides, rHSA-P53i and rHSA-PMI, surprisingly bind to Bcl-xL and Mcl-1.

Figure 10A:
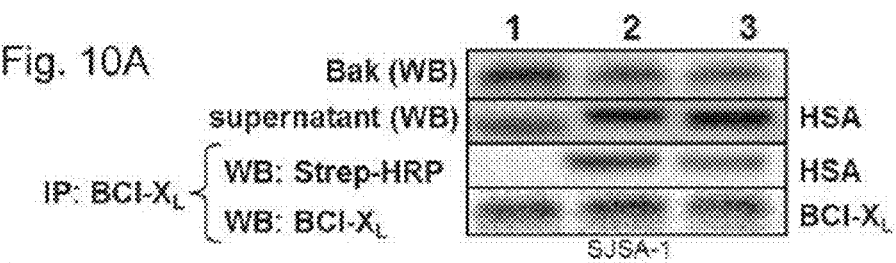
FIG. 10A, FIG. 10B, and FIG. 10C shows that rHSA-P53i reduces Bak-Bcl-xL and BAK-MCL-1. rHSA-P53i reduces Bak-Bcl-xL (FIG. 10A-10C) and BAK-MCL-1 (FIG. 10D) interactions in 3 cell lines. To determine whether rHSA fusion proteins were able to displace Bak from the BH3 binding groove of Bcl-xL, 4 µg each of biotin-rHSA (lane 1), biotin-rHSA-P53i (lane 2), or biotin-rHSA-PMI (lane 3) was added to 200 µg of SJSA-1 (FIG. 10A) or Hela (FIG. 10B) whole cell lysates. Bcl-xL or MCL-1 antibody was added to the lysate followed by pulling down Bcl-xL or MCL-1 and rHSA complexes using Protein A/G (1:1) resins. Samples were then analyzed by SDS-PAGE and Western blotting using Bcl-xL, Bak, and Streptavidin-HRP (Strep-HRP) antibodies. Protein band quantitation was determined using Image J software. HSA-p53i replaces BCL-XL or MCL-1-bound BAK. It is shown by decreased amount of BAK associated with BCL-XL or MCL.
Figure 10B:
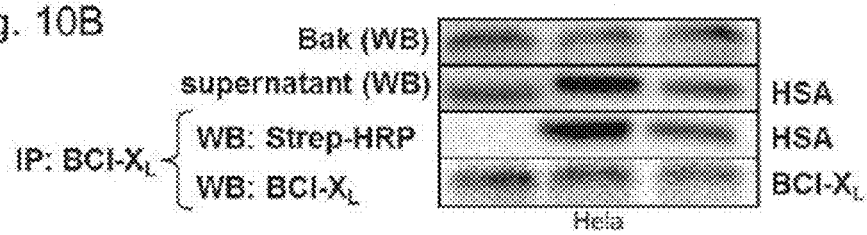
Figure 10C:
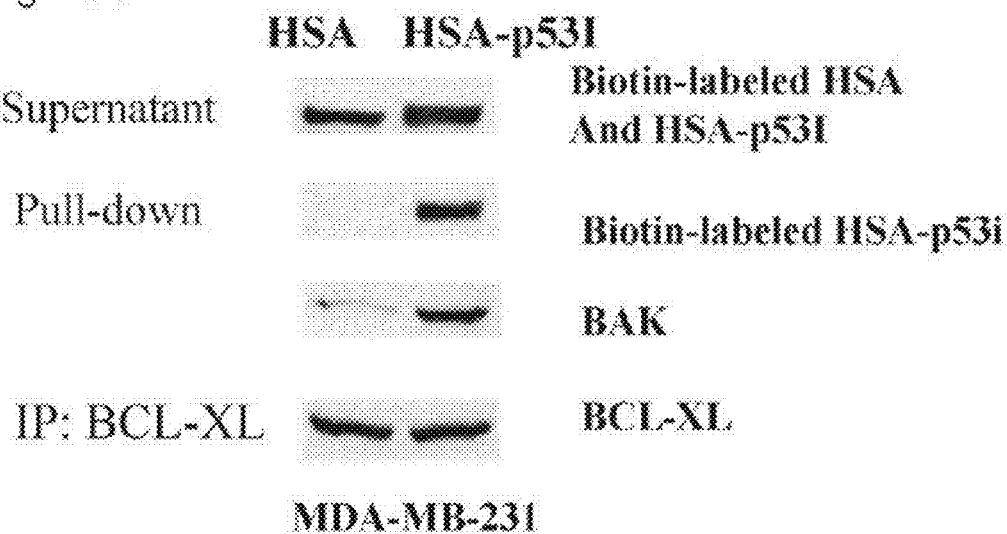

Example 12: Exemplary Fusion Polypeptide rHSA-P53i Reduces Bak-Bcl-xL and BAK-MCL-1 Interactions Having shown that rHSA-P53i and rHSA-PMI bind to Bcl-xL and Mcl-1, it was next determined whether rHSA fusion proteins were able to displace Bak from the BH3 binding groove of Bcl-xL. Towards that biotin-rHSA, biotin-rHSA-P53i, or biotin-rHSA-PMI was added to MDA-MB-231 (p53 negative cancer cell line), SJSA-1 (p53 positive cancer cell line) or Hela (p53 under-expressing cancer cell line) whole cell lysates. Proteins were then pulled down using anti-Bcl-xL antibody and samples were then analyzed by SDS-PAGE and Western blotting using Bcl-xL, Bak, and Streptavidin-HRP (Strep-HRP) antibodies. The data for SJSA-1, Hela and MDA-MB-231 are depicted in FIGS. 10A, 10B, and 10C, respectively. The amount of protein in each band was determined using Image J software (data not shown). Quantitation of band intensities showed that biotin-rHSA-P53i and biotin-rHSA-PMI reduced Bak-Bcl-xL interaction (data not shown).

In a separate experiment, biotin-rHSA or biotin-rHSA-P53i was added to MDA-MB-231, SJSA-1 or Hela whole cell lysates. Proteins were then pulled down using anti-MCL-1 antibody and samples were then analyzed by SDS-PAGE and Western blotting using MCL-1, BAK, and Streptavidin-HRP (Strep-HRP) antibodies. The data, exhibited in FIG. 10D, shows that the amount of BAK pulled down by anti-MCL-1 antibody was lesser when biotin-rHSA-P53i was added to cell lysate, compared to when biotin-rHSA was added. The amount of protein in each band was determined using Image J software (data not shown). Quantitation of band intensities showed that rHSA-P53i reduced MCL-1 interaction (data not shown). It is likely that biotin-rHSA-P53i and biotin-rHSA-PMI reduce interaction between other pro-apoptotic and anti-apoptotic Bcl-2 family members.

Example 13: Exemplary Fusion Polypeptide rHSA-P53i Promotes Release of Cytochrome C It is well known that Bcl-XL, MCL-1 and BAK are Bcl-2 family members. There are a total of 25 genes in the Bcl-2 family known to date, which are classified in to either pro-apoptotic (Bax, Diva, BCl-Xs, Bik, Bim, Bad, Bid, Bak, Bok, Egl-1, Bax, etc) or anti-apoptotic (including Bcl-2 proper, Bcl-xL, and Bcl-w, CED-9, A1, Bfl-1, among an assortment of others) members. These proteins govern mitochondrial outer membrane permeabilization. Disruption of mitochondrial outer membrane permeabilization leads to release of cytochrome C into the cytosol which, once there, activates caspase-9 and caspase-3, leading to apoptosis. It is thought action of the pro-apoptotic members of Bcl-2 family proteins induces, and anti-apoptotic members inhibits the mitochondrial outer membrane permeabilization.

Since the exemplary fusion polypeptide, rHSA-P53i, reduces Bak-Bcl-xL and BAK-MCL-1 interactions, it was next determined how the fusion polypeptide affects apoptosis in target cancer cells having different p53 genotypes. Towards that, increasing amounts of rHSA-P53i were added to Hela, SJSA-1 or MDA-MB-231 cells. Cytosolic and mitochondrial fractions were isolated and subjected to Western blotting using anti-Cytochrome C antibody. As shown in FIG. 11, the amount of cytochrome C increased in the cytoplasmic fraction in a dose dependent manner, in all three cell lines, irrespective of their p53 status. There was a corresponding decrease in the amount of cytochrome C in the mitochondrial fraction. The release cytochrome C is expected to once there, activates caspase-9 and caspase-3, leading to apoptosis. These data show that rHSA-P53i promotes release of cytochrome C, irrespective of p53 genotype, and phenotype of the cancer cells.

Figure 12A:
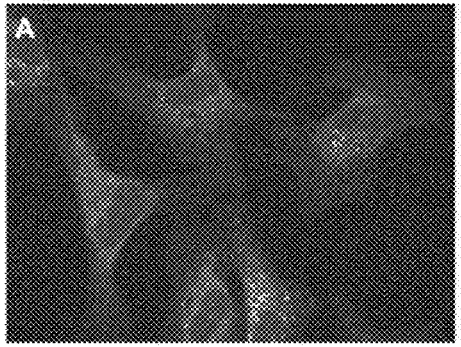
FIG. 12A, FIG. 12B, FIG. 12C, and FIG. 12D show that rHSA-P53i co-localizes with mitochondria in SJSA-1 and Hela cells. FITC-labeled rHSA (5 μM) and FITC-rHSA-P53i (5 μM), were added to SJSA-1 and Hela cells (green). Mitochondrial and nuclear staining was performed using MitoTracker Deep Red (red) and Hoechst 33342 (blue), respectively. Visualization at 60× magnification revealed abundant yellow staining in cells treated with rHSA-P53i (FIG. 12B and FIG. 12D), indicating rHSA-P53i efficiently co-localized with mitochondrial organelles. Despite efficient rHSA uptake in all conditions, mitochondrial co-localization was not observed in cells treated with rHSA (FIG. 12A and FIG. 12C).
Figure 12B:
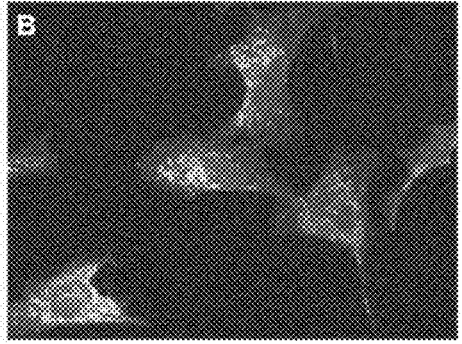
Figure 12C:
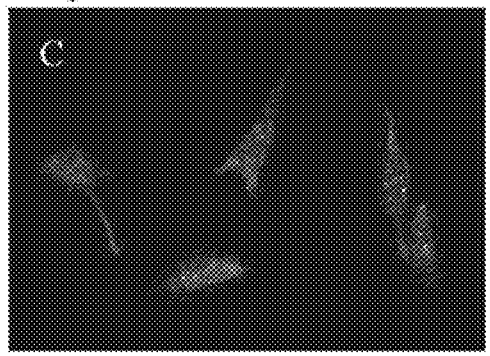
Figure 12D:

Example 14: Exemplary Fusion Polypeptide rHSA-P53i Co-Localizes with Mitochondria in SJSA-1 and Hela Cells In order to determine whether rHSA-P53i co-localizes with mitochondria, SJSA-1 and Hela cells were treated with FITC-labeled rHSA, FITC-rHSA-P53i, and FITC-rHSA-PMI. Mitochondrial and nuclear staining was performed using MitoTracker Deep Red (red) and Hoechst 33342 (blue), and the cells were then subjected to immunofluorescence microscopy. As shown in FIGS. 12A and C, HSA showed punctate localization. This may be consistent with localization of serum albumin with lysosomal system or secretory apparatus as has been previously seen (Yokota and Fahimi, Proceedings of National Academy of Sciences of the United States of America, 78: 4970-4974, 1981; Baghdiguian et al., Cancer Letters 101179-84, 1996). Despite efficient rHSA uptake in all conditions, mitochondrial co-localization was not observed in cells treated with rHSA (A and C). In contrast, visualization at 60× magnification revealed abundant yellow staining in cells treated with rHSA-P53i (B and D), and rHSA-PMI (data not shown) indicating the exemplary fusion polypeptide, rHSA-P53i, efficiently co-localized with mitochondrial organelles.

Figure 13A:
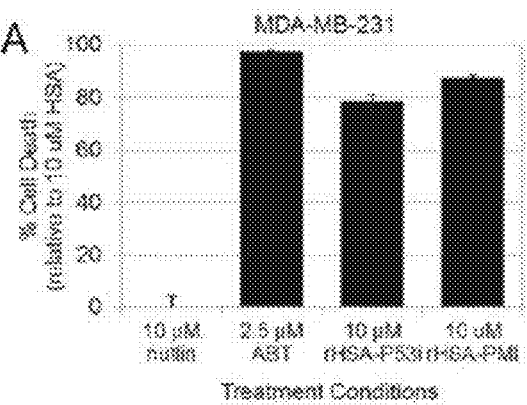
FIG. 13A, FIG. 13B, and FIG. 13C show that Cytotoxic activity of rHSA-P53i and rHSA-PMI is independent of p53 genotype. rHSA fusion proteins were added to MDA-MB-231 (FIG. 13A), SJSA-1 (FIG. 13B), or Hela (FIG. 13C) cells at the indicated concentrations and allowed to incubate for 24 hrs. Nutlin (10 μM) served as a negative control in MDA-MB-231 (p53-mutant) and Hela (unstable wild type p53) cells as it relies on a wild type p53-dependent cytotoxic mechanism, and ABT-263 (ABT, 2.5 μM), a BH3 mimetic (Bcl-xL inhibitor), was included as a positive control to confirm the presence of functional mitochondrial-mediated cytotoxic pathways. Cytotoxicities were measured by CyQuant Assay and normalized according to 10 μM rHSA-treated cells. Results are displayed as percent cell death relative to 10 μM rHSA-treated wells. Data are representative of 3 independent experiments performed in triplicate. Error bars indicate ±SD.
Figure 13B:
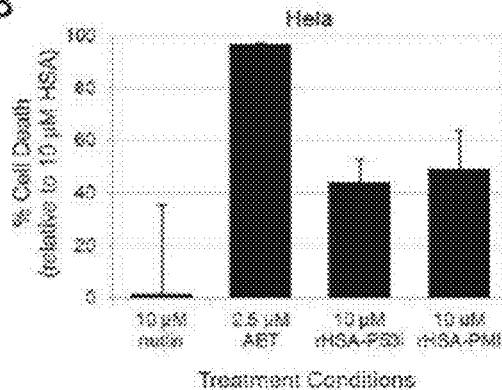
Figure 13C:
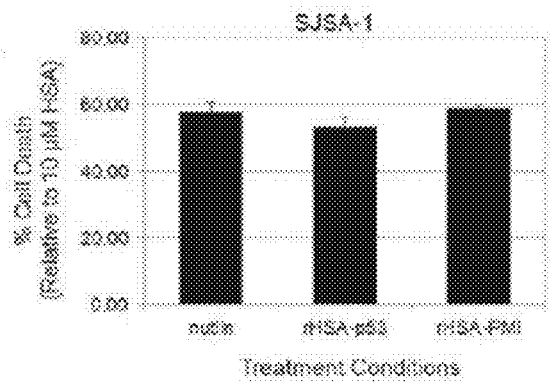

Example 15: Cytotoxic Activity of Exemplary Fusion Polypeptides, rHSA-P53i and rHSA-PMI, is Independent of p53 Status To determine whether rHSA-P53i and rHSA-PMI induce to cell death, HSA or the rHSA fusion proteins were added to MDA-MB-231, SJSA-1 or Hela cells and allowed to incubate for 24 hrs. Nutlin was used as a negative control in MDA-MB-231 (p53-mutant) and Hela (unstable wild type p53) cells as it relies on a wild type p53-dependent cytotoxic mechanism, and ABT-263, a BH3 mimetic (Bcl-xL inhibitor), was included as a positive control to confirm the presence of functional mitochondrial-mediated cytotoxic pathways. Cytotoxicities were measured by CyQuant Assay and normalized according to rHSA-treated cells. A bar graph showing cell death, relative to rHSA-treated cells, from representative of three independent experiments, performed in triplicate, are displayed in FIG. 13. As shown, nutlin killed p53-positive SJSA-1 cells, but not MDA-MB-231 or Hela cells, showing requirement for wild type levels of wild type p53 in the mechanism of cell death by nutlin. ABT-263 (ABT) killed MDA-MB-231 and Hela cells showing presence of mitochondrial-mediated cytotoxic pathways. Both rHSA-P53i and rHSA-PMI induced cell death in SJSA-1 cells (p53 positive cancer cell line) as well as MDA-MB-231 cells (p53 negative cancer cell line), or Hela cells (p53 under-expressing cancer cell line), illustrating cytotoxic activity of exemplary fusion polypeptides rHSA-P53i and rHSA-PMI is independent of p53 status.

Figure 14A:
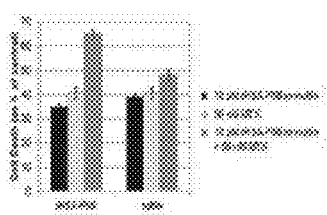
FIG. 14A, FIG. 14B, and FIG. 14C show that HSA-PMI has synergistic effect on SJSA-1 xenograft tumor model. HSA-PMI may induce apoptosis by 1) interrupting MDM2/MDMX and p53 interaction, 2) induce the releasing BAK from MCL-1 or BCL-Xl and result in apoptosis.

Example 16: Co-Administration of an Exemplary Fusion Polypeptide, rHSA-PMI, and an Exemplary Anticancer Agent, Methotrexate (MTX), Enhances Apoptotis Compared to the Agent Alone in SJSA-1 Cells As shown above, HSA-PMI may induce apoptosis by disrupting MDM2/MDMX-p53 interaction and/or by inducing the release of BAK from MCL-1 or BCL-Xl. This mechanism may suggest that the agent may show synergistic effect with many anticancer agents. To test this hypothesis, SJSA cells were treated with MTX alone, HSA-PMI/nutlin alone, or MTX and HSA-PMI/nutlin. Nutlin was used as an example of as shown in FIG. 14A, the amount of cell death induced by MTX was not additive with that induced by nutlin; however, the amount of cell death induced by MTX and HSA-PMI was enhanced by each other. This demonstrates that the fusion polypeptides of this invention provide surprisingly synergistic results when co-administered with an anti-cancer agent.

Figure 14B:
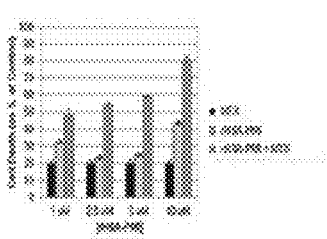
Figure 14C:
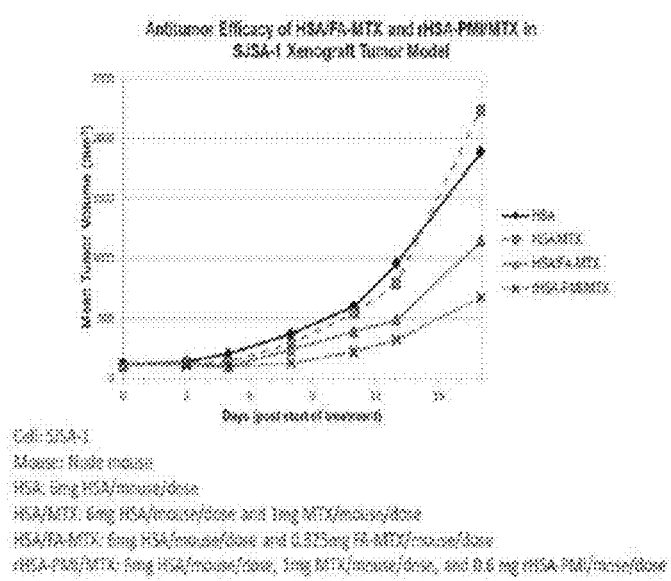

Example 17: Exemplary Fusion Polypeptide, HSA-PMI, has a Synergistic Effect on SJSA-1 Xenograft Tumor Model To extend the above findings to in vivo settings, SJSA-1 xenografts were treated with HSA, HSA/MTX, HSA/FA-MTX, and an exemplary fusion polypeptide, rHSA-PMI/MTX, as indicated in FIG. 14. These data show that efficacy of HSA/FA-MTX was enhanced by PMA as evidenced by rHSA-PMI/MTX treatment.

To determine whether exemplary fusion polypeptides, rHSA-P53i and rHSA-PMI, induce cell death, HSA or the rHSA fusion proteins were added to MDA-MB-231, SJSA-1 or Hela cells and allowed to incubate for 24 hrs. Nutlin was used as a negative control in MDA-MB-231 (p53-mutant) and Hela (unstable wild type p53) cells as it relies on a wild type p53-dependent cytotoxic mechanism, and ABT-263, a BH3 mimetic (Bcl-xL inhibitor), was included as a positive control to confirm the presence of functional mitochondrial-mediated cytotoxic Pathways. Cytotoxicities were measured by CyQuant Assay and normalized according to rHSA-treated cells. A bar graph showing cell death, relative to rHSA-treated cells, from representative of three independent experiments, performed in triplicate, are displayed in FIG. 13. As shown, nutlin killed p53-positive SJSA-1 cells, but not MDA-MB-231 or Hela cells, showing requirement for wild type levels of wild type p53 in the mechanism of cell death by nutlin. ABT-263 (ABT) killed MDA-MB-231 and Hela cells showing presence of mitochondrial-mediated cytotoxic pathways. Both rHSA-P53i and rHSA-PMI induced cell death in SJSA-1 cells (p53 positive cancer cell line) as well as MDA-MB-231 cells (p53 negative cancer cell line), or Hela cells (p53 under-expressing cancer cell line), illustrating that the cytotoxic activity of exemplary fusion polypeptides of this invention, rHSA-P53i and rHSA-PMI, is surprisingly independent of p53 status.

The methods and compositions of this invention are therefore useful in developing new therapeutic approaches to cancer. Restoring p53 function is a common approach used in cancer therapy, but that approach required either that the cancer cell has functional p53 or delivery of extrinsic functional p53 into cancer cells. These approaches were focused on the restoring of p53 function by blocking MDM2 and p53 interaction and accordingly, p53-derived peptides or analogues have not previously been tested for induction of apoptosis in p53 deletion or mutant cancers. As shown above, p53-derived peptide or p53-activating peptides provided in the fusion polypeptides of this invention can induce cytotoxicity regardless of functional p53 or p53 genotype. Previous studies have shown that p53 can interact with BCL-XL and MCL, but the relevance of those interactions was not clear since no studies previously demonstrated the cytotoxicity of p53-peptides such as a p53-derived peptide or p53-activating peptide in cells with p53 mutations, including p53 negative cells or cells expressing low activities of p53. The results of the study set forth herein proves that the fusion polypeptides of this invention can effectively kill cancer cells independent of the presence of functional p53 or p53 genotype or phenotype. The finding that p53-derived peptide or p53-activating peptides efficiently induce apoptosis in all cell lines tested indicates that the fusion polypeptides of this invention have broad application for delivery of p53 agonists, such as p53-peptides, for example, p53-derived peptides and p53-activating peptides or their analogs for treatment of most cancers.

This is the first demonstration of applying a therapy previously regarded as "p53-dependent" to cells, regardless of p53 genotype, and therefore, it surprisingly expands the therapeutic spectrum of p53-derived peptides, p53-activating peptides and/or their peptide or peptidomitice or small molecule analogs for use in any of the methods of this invention. There are other approaches to target either BCL-XL or MCL to induce apoptosis, but not both, and cancer cells have been shown to quickly develop resistance to approaches to target either BCL-XL or MCL. There are approaches to target MDM2 or MDMX, but these approaches do not tackle BCL-XL or MCL, or have never been tried in cells with p53 mutation or deletion. The proposed approach can achieve the goal: one stone, four birds for any direction (theoretically, most cancer cells).

The strategy of using p53-derived peptide or p53-activating peptides may be combined with an efficient peptide delivery strategy. Further, the p53-derived peptide or p53-activating peptides can be administered in combination with chemotherapeutics to boost synergistic efficacy. The power of human serum albumins to carry other drugs allows one to simultaneously administer molecule binds to multiple therapeutic agents, for example administering agents modulating four targets and affects two essential pathways. This approach will allow countering the ability of cancer cells to develop resistance.

A number of embodiments of the invention have been described. Nevertheless, it will be understood that various modifications may be made without departing from the spirit and scope of the invention. Accordingly, other embodiments are within the scope of the following claims. For example, any of the fusion polypeptides described herein may be used in any of the methods described herein, or as exemplified in any of the examples.

REFERENCES

1. Zhang X X, Eden H S, Chen X (2012) Peptides in cancer nanomedicine: drug carriers, targeting ligands and protease substrates. J Control Release 159: 2-13.
2. Hupp T R, Meek D W, Midgley C A, Lane D P (1992) Regulation of the specific DNA binding function of p53. Cell 71: 875-886.
3. el-Deiry W S (1998) Regulation of p53 downstream genes. Semin Cancer Biol 8: 345-357.
4. Ventura A, Kirsch D G, McLaughlin M E, Tuveson D A, Grimm J et al. (2007) Restoration of p53 function leads to tumour regression in vivo. Nature 445: 661-665.
5. Rinn J L, Huarte M. (2011) To repress or not to repress: this is the guardian's question. Trends Cell Biol 21: 344-353.
6. Bond G L, Hu W, Levine A J (2005) MDM2 is a central node in the p53 pathway: 12 years and counting. Curr Cancer Drug Targets 5: 3-8.
7. Freedman D A, Wu L, Levine A J (1999) Functions of the MDM2 oncoprotein. Cell Mol Life Sci 55: 96-107.
8. Böttger A, Böttger V, Garcia-Echeverria C, Chène P, Hochkeppel H K et al. (1997) Molecular characterization of the hdm2-p53 interaction. J Mol Biol 269: 744-756.
9. Yang Y, Ludwig R L, Jensen J P, Pierre S A, Medaglia M V et al. (2005) Small molecule inhibitors of HDM2 ubiquitin ligase activity stabilize and activate p53 in cells. Cancer Cell 7: 547-559.
10. Vassilev L T, Vu B T, Graves B, Carvajal D, Podlaski F et al. (2004) In vivo activation of the p53 pathway by small-molecule antagonists of MDM2. Science 303: 844-848.
11. Hu B, Gilkes D M, Farooqi B, Sebti S M, Chen J (2006) MDMX overexpression prevents p53 activation by the MDM2 inhibitor Nutlin. J Biol Chem 281: 33030-33035.
12. Wade M, Wong E T, Tang M, Stommel J M, Wahl G M (2006) Hdmx modulates the outcome of p53 activation in human tumor cells. J Biol Chem 281: 33036-33044.
13. Brown C J, Lain S, Verma C S, Fersht A R, Lane D P (2009) Awakening guardian angels: drugging the p53 pathway. Nat Rev Cancer 9: 862-873.
14. Li C, Pazgier M, Yuan W, Liu M, Wei G et al. (2010) Systematic mutational analysis of peptide inhibition of the p53-MDM2/1MDMX interactions. J Mol Biol 398: 200-213.
15. Pazgier M, Liu M, Zou G, Yuan W, Li C et al. (2009) Structural basis for high-affinity peptide inhibition of p53 interactions with MDM2 and MDMX. Proc Natl Acad Sci USA 106: 4665-4670.
16. Fasano M, Curry S, Terreno E, Galliano M, Fanali G et al. (2005) The extraordinary ligand binding properties of human serum albumin. IUBMB Life 57: 787-796.
17. Chuang V T, Kragh-Hansen U, Otagiri M (2002) Pharmaceutical strategies utilizing recombinant human serum albumin. Pharm Res 19: 569-577.
18. Kratz F (2008) Albumin as a drug carrier: design of prodrugs, drug conjugates and nanoparticles. J Control Release 132: 171-183.
19. Gradishar W J, Tjulandin S, Davidson N, Shaw H, Desai N et al. (2005) Phase III trial of nanoparticle albumin-bound paclitaxel compared with polyethylated castor oil-based paclitaxel in women with breast cancer. J Clin Oncol 23: 7794-7803.
20. Vousden K H, Prives C (2009) Blinded by the Light: The Growing Complexity of p53. Cell 137: 413-431.
21. Boratyński J, Opolski A, Wietrzyk J, Górski A, Radzikowski C (2000) Cytotoxic and antitumor effect of fibrinogen-methotrexate conjugate. Cancer Lett 148: 189-195.
22. Tzefos M, Olin J L Glucagon-like peptide-1 analog and insulin combination therapy in the management of adults with type 2 diabetes mellitus. Ann Pharmacother 44: 1294-1300.
23. Peterson G E (2006) Intermediate and long-acting insulins: a review of NPH insulin, insulin glargine and insulin detemir. Curr Med Res Opin 22: 2613-2619.
24. Rustgi V K (2009) Albinterferon alfa-2b, a novel fusion protein of human albumin and human interferon alfa-2b, for chronic hepatitis C. Curr Med Res Opin 25: 991-1002.
25. Pignatello R, Guccione S, Forte S, Di Giacomo C, Sorrenti V et al. (2004) Lipophilic conjugates of methotrexate with short-chain alkylamino acids as DHFR inhibitors. Synthesis, biological evaluation, and molecular modeling. Bioorg Med Chem 12: 2951-2964.
26. Singh Y, Palombo M, Sinko P J (2008) Recent trends in targeted anticancer prodrug and conjugate design. Curr Med Chem 15: 1802-1826.
27. Kratz F, Müller I A, Ryppa C, Warnecke A (2008) Prodrug strategies in anticancer chemotherapy. Chemmedchem 3: 20-53.

28. Cregg J M, Tolstorukov I, Kusari A, Sunga J, Madden K et al. (2009) Expression in the yeast Pichia pastoris. Methods Enzymol 463: 169-189.
29. Travis J, Bowen J, Tewksbury D, Johnson D, Pannell R (1976) Isolation of albumin from whole human plasma and fractionation of albumin-depleted plasma. Biochem J 157: 301-306.
30. Chen R F (1967) Removal of fatty acids from serum albumin by charcoal treatment. J Biol Chem 242: 173-181.
31. Kussie P H, Gorina S, Marechal V, Elenbaas B, Moreau J et al. (1996) Structure of the MDM2 oncoprotein bound to the p53 tumor suppressor transactivation domain. Science 274: 948-953.
32. Schon O, Friedler A, Bycroft M, Freund S M, Fersht A R (2002) Molecular mechanism of the interaction between MDM2 and p53. J Mol Biol 323: 491-501.
33. El-Deiry W S (2003) The role of p53 in chemosensitivity and radiosensitivity. Oncogene 22: 7486-7495.
34. Weber J D, Jeffers J R, Rehg J E, Randle D H, Lozano G et al. (2000) p53-independent functions of the p19 (ARF) tumor suppressor. Genes Dev 14: 2358-2365.
35. Tao W, Levine A J (1999) P19(ARF) stabilizes p53 by blocking nucleo-cytoplasmic shuttling of Mdm2. Proc Natl Acad Sci USA 96: 6937-6941.
36. Kuo M L, Duncavage E J, Mathew R, den Besten W, Pei D et al. (2003) Arf induces p53-dependent and -independent antiproliferative genes. Cancer Res 63: 1046-1053.
37. Barak Y, Juven T, Haffner R, Oren M (1993) Mdm2 expression is induced by wild type p53 activity. EMBO J 12: 461-468.
38. Spector A A (1975) Fatty acid binding to plasma albumin. J Lipid Res 16: 165-179.
39. John T A, Vogel S M, Tiruppathi C, Malik A B, Minshall R D (2003) Quantitative analysis of albumin uptake and transport in the rat microvessel endothelial monolayer. Am J Physiol Lung Cell Mol Physiol 284: L187-L196.
40. Desai N, Trieu V, Yao Z, Louie L, Ci S, et al. (2006) Increased antitumor activity, intratumor paclitaxel concentrations, and endothelial cell transport of cremophor-free, albumin-bound paclitaxel, ABI-007, compared with cremophor-based paclitaxel. Clin Cancer Res 12: 1317-1324.
41. Andersen J T, Dalhus B, Cameron J, Daba M B, Plumridge A et al. (2012) Structure-based mutagenesis reveals the albumin-binding site of the neonatal Fc receptor. Nat Commun 3: 610.
42. Mendrysa S M, McElwee M K, Michalowski J, O'Leary K A, Young K M et al. (2003) Mdm2 Is critical for inhibition of p53 during lymphopoiesis and the response to ionizing irradiation. Mol Cell Biol 23: 462-472.
43. Caelles C, Helmberg A, Karin M (1994) p53-dependent apoptosis in the absence of transcriptional activation of p53 target genes. Nature 370: 220-223.

What is claimed is:

1. A fusion polypeptide comprising a human serum albumin and a p53-peptide, further comprising one or more anticancer agent, wherein the one or more anticancer agent is bound to the human serum albumin via covalent interactions, or is chemically conjugated to a natural ligand of the human serum albumin, wherein the natural ligand is bound to the human serum albumin.

2. The fusion polypeptide of claim 1, wherein the p53-peptide is chemically linked to the human serum albumin or a fragment thereof.

3. The fusion polypeptide of claim 2, wherein the p53-peptide is covalently cross-linked to the human serum albumin or a fragment thereof via carboxyl groups, amino groups, amine-reactive groups, sulfhydryl-reactive groups, aldehyde-reactive groups, hydroxyl (nonaqueous)-reactive groups or a combination thereof.

4. The fusion polypeptide of claim 1, wherein the p53-peptide is a p53-derived peptide or a p53-activating peptide.

5. The fusion polypeptide of claim 1, wherein the fusion polypeptide is a chemically cross-linked conjugate comprising:
(a) a p53-derived peptide and a human serum albumin polypeptide, or
(b) a p53-activating peptide and a human serum albumin polypeptide.

6. The fusion polypeptide of claim 5, wherein one or more anticancer agent is selected from the group consisting of 2,3,4,5,6-pentafluoro-N-(3-fluoro-4-methoxyphenyl)benzene sulfonamide, abiraterone acetate, afatinib, aldesleukin, alemtuzumab, alitretinoin, altretamine, amifostine, aminoglutethimide, anagrelide, anastrozole, anhydrovinblastine, arsenic trioxide, asparaginase, auristatin, azacitidine, azathioprine, bendamustine, bevacizumab, bexarotine, bicalutamide, bleomycin, BMS 184476, bortezomib, busulfan, cachectin, capecitabine, carboplatin, carmustine, cemadotin, cetuximab, chlorambucil, cisplatin, cladribine, crizotinib, cyclophosphamide, cytarabine, dacarbazine, dactinomycin, dasatinib, daunorubicin, denileukin diftitox, decitabine, 3',4'-didehydro-4'-deoxy-8'-norvin-caleukoblastine, N,N-dimethyl-L-valyl-L-valyl-N-methyl-L-valyl-L-proly-1-Lproline-t-butylamide, docetaxel, dexamethasone, doxifluridine, doxorubicin, epirubicin, epoetin alpha, epothilone, erlotinib, estramustine, etinostat, etoposide, everolimus, exemestane, filgrastim, floxuridine, fludarabine, fluorouracil, fluoxymesterone, flutamide, folate linked alkaloids, gefitinib, gemcitabine, gemtuzumab ozogamicin, GM-CT-01, goserelin, hexamethylmelamine, hydroxyureas, ibritumomab, idarubicin, ifosfamide, imatinib, interferon alpha, interferon beta, irinotecan, ixabepilone, lapatinib, leucovorin, leuprolide, lenalidomide, letrozole, lomustine, mechlorethamine, megestrol, melphalan, mercaptopurine, methotrexate, mitomycin, mitoxantrone, nelarabine, nilotinib, nilutamide, octreotide, ofatumumab, oprelvekin, oxaliplatin, paclitaxel, panitumumab, pemetrexed, pentostatin, polysaccharide galectin inhibitors, procarbazine, raloxifene, retinoic acids, rituximab, romiplostim, sargramostim, sorafenib, streptozocin, sunitinib, tamoxifen, temsirolimus, temozolamide, teniposide, thalidomide, thioguanine, thiotepa, tioguanine, topotecan, toremifene, tositumomab, trametinib, trastuzumab, tretinoin, valrubicin, vegf inhibitors and traps, vinblastine, vincristine, vindesine, vinorelbine, vintafolide, vorinostat, and a combination thereof.

7. A fusion polypeptide comprising a human serum albumin and a p53-peptide, further comprising one or more anticancer agent, wherein the anticancer agent is covalently bound to the human serum albumin polypeptide.

8. The fusion polypeptide of claim 1, wherein the one or more anticancer agent is chemically conjugated to a natural ligand of the human serum albumin.

9. The fusion polypeptide of claim 8, wherein the natural ligand of the human serum albumin is a fatty acid, an amino acid, a nutrient, a vitamin, a metabolite, an hormone, or a drug.

10. The fusion polypeptide of claim 9, wherein the natural ligand of human serum albumin is a fatty acid.

11. A pharmaceutical composition comprising a fusion polypeptide of claim 1.

12. The pharmaceutical composition of claim 11, further comprising a pharmaceutically acceptable excipient, wherein the fusion polypeptide is lyophilized.

13. The pharmaceutical composition of claim 11, further comprising a pharmaceutically acceptable excipient.

14. The pharmaceutical composition of claim 13, where the pharmaceutically acceptable excipient is selected from the group consisting of a solvent, solubilizer, stabilizer, buffer, pH adjuster, tonicity modifier, bulking agent, filler, binder, viscosity enhancer, viscosity reducer, emulsifier, surfactant, chelating agent, disintegrant, glidant, lubricant and adjuvant.

15. The pharmaceutical composition of claim 11, wherein the pharmaceutical composition is formulated as a lyophilisate, powder, injection, solution, suspension, emulsion, powder, granule, capsule, tablet, pellet, dragee, semi-solid, suppositorie, ointment, cream, lotion, inhalant, cataplasm, gel, tape, eye drop, syrup, or an aerosol.

16. A fusion polypeptide comprising a human serum albumin and a p53-peptide, wherein the p53-peptide is selected from the group consisting of SEQ ID NO: 1, SEQ ID NO: 2, SEQ ID NO: 3, and SEQ ID NO:7.

17. A fusion polypeptide comprising a serum albumin, or a fragment thereof retaining its cell transport and/or ligand binding properties, and a p53-peptide further comprising a small molecule drug, wherein the small molecule drug is bound to the serum albumin via covalent interactions, or is chemically conjugated to a natural ligand of the serum albumin, wherein the natural ligand is bound to the serum albumin.

18. The fusion polypeptide of claim 17, wherein the serum albumin is an animal serum albumin.

19. The fusion polypeptide of claim 17, wherein the serum albumin is selected from an avian, bovine, canine, *cervine*, equine, ichthyic, feline, ovine, piscine and porcine albumin.

20. The fusion polypeptide of claim 17, wherein the serum albumin is a recombinant protein.

21. The fusion polypeptide of claim 17, wherein the small molecule drug is an extremely hydrophobic drug.

22. The fusion polypeptide of claim 17, wherein the anticancer agent is bound to a ligand of the serum albumin.

23. The fusion polypeptide of claim 22, wherein the ligand of the serum albumin is selected from the group consisting of a fatty acid, an amino acid, a nutrient, a vitamin, a metabolite, an hormone and a drug.

* * * * *

```
SEQUENCE LISTING

<160> NUMBER OF SEQ ID NOS: 34

<210> SEQ ID NO 1
<211> LENGTH: 12
<212> TYPE: PRT
<213> ORGANISM: Homo sapiens

<400> SEQUENCE: 1

Glu Thr Phe Ser Asp Leu Trp Lys Leu Leu Pro Glu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ser Phe Ala Glu Tyr Trp Ala Leu Leu Ser Pro
1               5                   10

<210> SEQ ID NO 3
<211> LENGTH: 8
<212> TYPE: PRT
<213> ORGANISM: Homo sapiens

<400> SEQUENCE: 3

Phe Ser Asp Leu Trp Lys Leu Leu
1               5

<210> SEQ ID NO 4
<211> LENGTH: 12
<212> TYPE: PRT
<213> ORGANISM: Homo sapiens
```

-continued

```
<400> SEQUENCE: 4

Glu Thr Phe Ser Asp Leu Trp Lys Leu Leu Pro Glu
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Val Val Pro Pro
1               5

<210> SEQ ID NO 6
<211> LENGTH: 5
<212> TYPE: PRT
<213> ORGANISM: Unknown
<220> FEATURE:
<223> OTHER INFORMATION: Description of Unknown:
      caspase cleavage site peptide

<400> SEQUENCE: 6

Asp Glu Val Asp Gly
1               5

<210> SEQ ID NO 7
<211> LENGTH: 12
<212> TYPE: PRT
<213> ORGANISM: Homo sapiens

<400> SEQUENCE: 7

Thr Ser Phe Ala Glu Tyr Trp Asn Leu Leu Ser Pro
1               5                   10

<210> SEQ ID NO 8
<211> LENGTH: 393
<212> TYPE: PRT
<213> ORGANISM: Homo sapiens

<400> SEQUENCE: 8

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140
```

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Lys Glu Asn
            275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 9
<211> LENGTH: 609
<212> TYPE: PRT
<213> ORGANISM: Homo sapiens

<400> SEQUENCE: 9

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
            85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

-continued

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu

<210> SEQ ID NO 10
<211> LENGTH: 585
<212> TYPE: PRT
<213> ORGANISM: Homo sapiens

<400> SEQUENCE: 10

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Arg Ala Asp Leu Pro Ser
290                 295                 300

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
                580                 585

<210> SEQ ID NO 11
<211> LENGTH: 11
<212> TYPE: PRT
<213> ORGANISM: Human immunodeficiency virus

<400> SEQUENCE: 11

Tyr Gly Arg Lys Lys Arg Arg Gln Arg Arg Arg
1               5                   10

<210> SEQ ID NO 12
<211> LENGTH: 18
<212> TYPE: PRT
<213> ORGANISM: Unknown
<220> FEATURE:
<223> OTHER INFORMATION: Description of Unknown:
      SynB1 peptide

<400> SEQUENCE: 12

Arg Gly Gly Arg Leu Ser Tyr Ser Arg Arg Arg Phe Ser Thr Ser Thr
1               5                   10                  15
```

Gly Arg

<210> SEQ ID NO 13
<211> LENGTH: 10
<212> TYPE: PRT
<213> ORGANISM: Unknown
<220> FEATURE:
<223> OTHER INFORMATION: Description of Unknown:
      SynB3 peptide

<400> SEQUENCE: 13

Arg Arg Leu Ser Tyr Ser Arg Arg Arg Phe
1               5                   10

<210> SEQ ID NO 14
<211> LENGTH: 12
<212> TYPE: PRT
<213> ORGANISM: Unknown
<220> FEATURE:
<223> OTHER INFORMATION: Description of Unknown:
      PTD-4 peptide

<400> SEQUENCE: 14

Pro Ile Arg Arg Arg Lys Lys Leu Arg Arg Leu Lys
1               5                   10

<210> SEQ ID NO 15
<211> LENGTH: 12
<212> TYPE: PRT
<213> ORGANISM: Unknown
<220> FEATURE:
<223> OTHER INFORMATION: Description of Unknown:
      PTD-5 peptide

<400> SEQUENCE: 15

Arg Arg Gln Arg Arg Thr Ser Lys Leu Met Lys Arg
1               5                   10

<210> SEQ ID NO 16
<211> LENGTH: 15
<212> TYPE: PRT
<213> ORGANISM: Flock house virus

<400> SEQUENCE: 16

Arg Arg Arg Arg Asn Arg Thr Arg Arg Asn Arg Arg Arg Val Arg
1               5                   10                  15

<210> SEQ ID NO 17
<211> LENGTH: 19
<212> TYPE: PRT
<213> ORGANISM: Brome Mosaic virus

<400> SEQUENCE: 17

Lys Met Thr Arg Ala Gln Arg Arg Ala Ala Ala Arg Arg Asn Arg Trp
1               5                   10                  15

Thr Ala Arg

<210> SEQ ID NO 18
<211> LENGTH: 13
<212> TYPE: PRT
<213> ORGANISM: Unknown
<220> FEATURE:
<223> OTHER INFORMATION: Description of Unknown:
      HTLV-II Rex-(4-16) peptide

<400> SEQUENCE: 18

Thr Arg Arg Gln Arg Thr Arg Arg Ala Arg Arg Asn Arg
1               5                   10

<210> SEQ ID NO 19
<211> LENGTH: 13
<212> TYPE: PRT
<213> ORGANISM: Unknown
<220> FEATURE:
<223> OTHER INFORMATION: Description of Unknown:
      D-Tat peptide

<400> SEQUENCE: 19

Gly Arg Lys Lys Arg Arg Gln Arg Arg Arg Pro Pro Gln
1               5                   10

<210> SEQ ID NO 20
<211> LENGTH: 13
<212> TYPE: PRT
<213> ORGANISM: Unknown
<220> FEATURE:
<223> OTHER INFORMATION: Description of Unknown:
      R9-Tat peptide

<400> SEQUENCE: 20

Gly Arg Arg Arg Arg Arg Arg Arg Arg Arg Pro Pro Gln
1               5                   10

<210> SEQ ID NO 21
<211> LENGTH: 27
<212> TYPE: PRT
<213> ORGANISM: Unknown
<220> FEATURE:
<223> OTHER INFORMATION: Description of Unknown:
      Transportan chimera peptide

<400> SEQUENCE: 21

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 22
<211> LENGTH: 17
<212> TYPE: PRT
<213> ORGANISM: Unknown
<220> FEATURE:
<223> OTHER INFORMATION: Description of Unknown:
      MAP peptide

<400> SEQUENCE: 22

Lys Leu Ala Leu Lys Leu Ala Leu Lys Leu Ala Leu Ala Leu Lys Leu
1               5                   10                  15

Ala

<210> SEQ ID NO 23
<211> LENGTH: 27
<212> TYPE: PRT
<213> ORGANISM: Unknown
<220> FEATURE:
<223> OTHER INFORMATION: Description of Unknown:
      SBP peptide

<400> SEQUENCE: 23

Met Gly Leu Gly Leu His Leu Leu Val Leu Ala Ala Ala Leu Gln Gly
1               5                   10                  15

Ala Trp Ser Gln Pro Lys Lys Lys Arg Lys Val

```
            20                  25

<210> SEQ ID NO 24
<211> LENGTH: 27
<212> TYPE: PRT
<213> ORGANISM: Unknown
<220> FEATURE:
<223> OTHER INFORMATION: Description of Unknown:
      FBP peptide

<400> SEQUENCE: 24

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 25
<211> LENGTH: 27
<212> TYPE: PRT
<213> ORGANISM: Unknown
<220> FEATURE:
<223> OTHER INFORMATION: Description of Unknown:
      MPG peptide

<400> SEQUENCE: 25

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 26
<211> LENGTH: 27
<212> TYPE: PRT
<213> ORGANISM: Unknown
<220> FEATURE:
<223> OTHER INFORMATION: Description of Unknown:
      MPG(deltaNLS) peptide

<400> SEQUENCE: 26

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 27
<211> LENGTH: 21
<212> TYPE: PRT
<213> ORGANISM: Unknown
<220> FEATURE:
<223> OTHER INFORMATION: Description of Unknown:
      Pep-1 peptide

<400> SEQUENCE: 27

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 28
<211> LENGTH: 21
<212> TYPE: PRT
<213> ORGANISM: Unknown
<220> FEATURE:
<223> OTHER INFORMATION: Description of Unknown:
      Pep-2 peptide
```

<400> SEQUENCE: 28

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 29
<211> LENGTH: 27
<212> TYPE: PRT
<213> ORGANISM: Artificial Sequence
<220> FEATURE:
<223> OTHER INFORMATION: Description of Artificial Sequence: Synthetic
      polyarginine peptide
<220> FEATURE:
<221> NAME/KEY: MOD_RES
<222> LOCATION: (3)..(27)
<223> OTHER INFORMATION: May or may not be present

<400> SEQUENCE: 29

Arg Arg Arg Arg Arg Arg Arg Arg Arg Arg Arg Arg Arg Arg Arg
1               5                   10                  15

Arg Arg Arg Arg Arg Arg Arg Arg Arg Arg Arg
            20                  25

<210> SEQ ID NO 30
<211> LENGTH: 27
<212> TYPE: PRT
<213> ORGANISM: Artificial Sequence
<220> FEATURE:
<223> OTHER INFORMATION: Description of Artificial Sequence: Synthetic
      polylysine peptide
<220> FEATURE:
<221> NAME/KEY: MOD_RES
<222> LOCATION: (3)..(27)
<223> OTHER INFORMATION: May or may not be present

<400> SEQUENCE: 30

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys
            20                  25

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
atcgctcgag aaaagagagg ctaagcgacg cacacaagag tgaggttgct           50

<210> SEQ ID NO 32
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccataggtct gaaaacgttt cacctcaact tcgtcggcgc ctaaggcagc ttgacttgca    60
gc                                                                  62

```
<210> SEQ ID NO 33
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgatgctagc actagtttat tcaggaagta gtttccatag gtctgaaaac gtttcacc        58

<210> SEQ ID NO 34
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgatgctagc ccgcggttat ggactaagaa gagcccagta ctcagcaaaa cttgtaccgt        60
caacttcgtc ggcgcc                                                       76
```